(12) United States Patent
Peng et al.

(10) Patent No.: US 8,530,456 B2
(45) Date of Patent: Sep. 10, 2013

(54) SONIC HEDGEHOG MODULATORS

(75) Inventors: Lee F. Peng, Somerville, MA (US);
Julia Lamenzo, Arlington, MA (US);
Nicole Maloof, Brookline, MA (US);
Kazuo Nakai, Itami (JP); Benjamin Stanton, Menlo Park, CA (US); Sara Jean Buhrlage, Somerville, MA (US);
Lawrence MacPherson, Marlborough, MA (US); Michel Weiwer, Cambridge, MA (US); Stuart L. Schreiber, Boston, MA (US)

(73) Assignees: President and Fellows of Harvard College, Cambridge, MA (US);
Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 117 days.

(21) Appl. No.: 12/988,755

(22) PCT Filed: Apr. 21, 2009

(86) PCT No.: PCT/US2009/041295
§ 371 (c)(1),
(2), (4) Date: Jan. 10, 2011

(87) PCT Pub. No.: WO2009/132032
PCT Pub. Date: Oct. 29, 2009

(65) Prior Publication Data
US 2011/0172233 A1 Jul. 14, 2011

Related U.S. Application Data

(60) Provisional application No. 61/046,710, filed on Apr. 21, 2008, provisional application No. 61/097,770, filed on Sep. 17, 2008.

(51) Int. Cl.
C07D 495/06 (2006.01)
C07D 493/06 (2006.01)
C07D 495/16 (2006.01)
C07D 493/16 (2006.01)
A61K 31/395 (2006.01)
A61P 35/00 (2006.01)

(52) U.S. Cl.
USPC .......................................... 514/183; 540/454

(58) Field of Classification Search
USPC ......................................... 540/454; 514/183
See application file for complete search history.

(56) References Cited

U.S. PATENT DOCUMENTS
2012/0020876 A1* 1/2012 Olive et al. .................. 424/1.11

FOREIGN PATENT DOCUMENTS
WO WO 00/74706 A1 12/2000
WO WO 2004/026304 A1 4/2004

OTHER PUBLICATIONS

International Search Report and Written Opinion for PCT/US2009/041295 mailed Dec. 28, 2009.
International Preliminary Report on Patentability for PCT/US2009/041295 mailed Nov. 4, 2010.
Barnes-Seeman et al., Expanding the functional group compatibility of small-molecule microarrays: discovery of novel calmodulin ligands. Angew Chem Int Ed Engl. May 30, 2003;42(21):2376-9.
Berge et al., Pharmaceutical salts. J Pharm Sci. Jan. 1977;66(1):1-19.
Blackwell et al., A one-bead, one-stock solution approach to chemical genetics: part 1. Chem Biol. Dec. 2001;8(12):1167-82.
Borycki et al., Control of somite patterning by Sonic hedgehog and its downstream signal response genes. Development. Feb. 1998;125(4):777-90.
Bradner et al., A robust small-molecule microarray platform for screening cell lysates. Chem Biol. May 2006;13(5):493-504.
Burke et al., A synthesis strategy yielding skeletally diverse small molecules combinatorially. J Am Chem Soc. Nov. 3, 2004;126(43):14095-104.
Burke et al., Generating diverse skeletons of small molecules combinatorially. Science. Oct. 24, 2003;302(5645):613-8.
Chen et al., Convergent diversity-oriented synthesis of small-molecule hybrids. Angew Chem Int Ed Engl. Apr. 8, 2005;44(15):2249-52.
Chen et al., Inhibition of Hedgehog signaling by direct binding of cyclopamine to Smoothened. Genes Dev. Nov. 1, 2002;16(21):2743-8.
Chen et al., Small molecule modulation of Smoothened activity. Proc Natl Acad Sci U S A. Oct. 29, 2002;99(22):14071-6. Epub Oct. 21, 2002.
Chiang et al., Cyclopia and defective axial patterning in mice lacking Sonic hedgehog gene function. Nature. Oct. 3, 1996;383(6599):407-13.
Clemons et al., A one-bead, one-stock solution approach to chemical genetics: part 2. Chem Biol. Dec. 2001;8(12):1183-95.
Coon et al., Differential epithelial expression of SHH and FOXF1 in usual and nonspecific interstitial pneumonia. Exp Mol Pathol. Apr. 2006;80(2):119-23. Epub Jan. 30, 2006.

(Continued)

*Primary Examiner* — Bruck Kifle
(74) *Attorney, Agent, or Firm* — Wolf, Greenfield & Sacks, P.C.; C. Hunter Baker

(57) ABSTRACT

The present invention relates to macrocyclic small molecule inhibitors of the Sonic Hedgehog signaling pathway, syntheses thereof, and intermediates thereto. Such small molecule modulators of the Sonic Hedgehog signaling pathway are useful in the treatment of proliferative diseases (e.g., basal cell carcinoma, Gorlin syndrome, medulloblastoma, or pancreatic cancer), pulmonary diseases (e.g., interstitial pnuemonitis or interstitial pulmonary fibrosis), and developmental disorders (e.g., phocomelia or cyclopia). Novel non-natural macrocycles are provided that inhibit Sonic Hedgehog induced-protein transcription.

30 Claims, 10 Drawing Sheets

(56) References Cited

OTHER PUBLICATIONS

Cooper et al., Teratogen-mediated inhibition of target tissue response to Shh signaling. Science. Jun. 5, 1998;280(5369):1603-7.
Ding et al., A role for chemistry in stem cell biology. Nat Biotechnol. Jul. 2004;22(7):833-40.
Evans et al., The Total Syntheses of the Isodityrosine-Derived Cyclic Tripeptides OF4949-III and K-13. Determination of the Absolute Configuration of K-13. J Am Chem Soc. 1989;111:1063-72.
Frank-Kamenetsky et al., Small-molecule modulators of Hedgehog signaling: identification and characterization of Smoothened agonists and antagonists. J Biol. Nov. 6, 2002;1(2):10.1-10.19.
Furukawa et al., Molecular mechanisms of pancreatic carcinogenesis. Cancer Sci. Jan. 2006;97(1):1-7.
Goetz et al., A highly conserved amino-terminal region of sonic hedgehog is required for the formation of its freely diffusible multimeric form. J Biol Chem. Feb. 17, 2006;281(7):4087-93. Epub Dec. 9, 2005.
Gokhale et al., Mechanism and specificity of the terminal thioesterase domain from the erythromycin polyketide synthase. Chem Biol. Feb. 1999;6(2):117-25.
Grubbs, Olefin metathesis. Tetrahedron. 2004:7117-40.
Grubbs et al., Recent Advances in Olefin Metathesis and Its Application in Organic Synthesis. Tetrahedron. 1998;54:4413-50.
Han et al., Recent development of peptide coupling reagents in organic synthesis. Tetrahedron. 2004;60:2447-67.
Harding et al., A receptor for the immunosuppressant FK506 is a cis-trans peptidyl-prolyl isomerase. Nature. Oct. 26, 1989;341(6244):758-60.
Hughes, Inhibiting Hedgehog. Nat Rev Drug Discov. Mar. 2009;8. Published online Feb. 20, 2009; doi:10.1038/nrd2835.
Ingham et al., Hedgehog signaling in animal development: paradigms and principles. Genes Dev. Dec. 1, 2001;15(23):3059-87.
Karlsson et al., Biosensor analysis of drug-target interactions: direct and competitive binding assays for investigation of interactions between thrombin and thrombin inhibitors. Anal Biochem. Feb. 1, 2000;278(1):1-13.
Kayed et al., Hedgehog signaling in the normal and diseased pancreas. Pancreas. Mar. 2006;32(2):119-29.
Kim et al., Relationship of stereochemical and skeletal diversity of small molecules to cellular measurement space. J Am Chem Soc. Nov. 17, 2004;126(45):14740-5.
Kittendorf et al., Interrogating the molecular basis for multiple macrolactone ring formation by the pikromycin polyketide synthase. Chem Biol. Aug. 2007;14(8):944-54.
Koehler et al., Discovery of an inhibitor of a transcription factor using small molecule microarrays and diversity-oriented synthesis. J Am Chem Soc. Jul. 16, 2003;125(28):8420-1.
Kumar et al., Small-molecule diversity using a skeletal transformation strategy. Org Lett. Jun. 23, 2005;7(13):2535-8.
Lee et al., A Strategy for Macrocyclic Ring Closure and Functionalization Aimed toward Split Pool Syntheses. J Am Chem Soc. 1999;121:10648-49.
Lo et al., A library of spirooxindoles based on a stereoselective three-component coupling reaction. J Am Chem Soc. Dec. 15, 2004;126(49):16077-86.
Macbeath et al., Printing Small Molecules as Microarrays and Detecting Protein-Ligand Interactions en Masse. J Am Chem Soc. 1999;121:7967-8.
Maity et al., Molecular mechanisms of Sonic hedgehog mutant effects in holoprosencephaly. Proc Natl Acad Sci U S A. Nov. 22, 2005;102(47):17026-31. Epub Nov. 10, 2005.
Matsumori et al., Mycosamine orientation of amphotericin B controlling interaction with ergosterol: sterol-dependent activity of conformation-restricted derivatives with an amino-carbonyl bridge. J Am Chem Soc. Aug. 3, 2005;127(30):10667-75.
Maynard et al., Purification Technique for the Removal of Ruthenium from Olefin Metathesis Reaction Products. Tetrahedron Lett. 1999;40:4137-40.
Myszka, Improving biosensor analysis. J Mol Recognit. Sep.-Oct. 1999;12(5):279-84.
Myszka, Survey of the 1998 optical biosensor literature. J Mol Recognit. Nov.-Dec. 1999; 12(6): 390-408.
Nakatsuka et al., Total Synthesis of FK506 and an FKBP Probe Reagent, $(C_8,C_9-{}^{13}C_2)$-FK506. J Am Chem Soc. 1990;112:5583-601.
Nguyen et al., Cross-regulation between Notch and p63 in keratinocyte commitment to differentiation. Genes Dev. Apr. 15, 2006;20(8):1028-42.
Nüsslein-Volhard et al., Mutations affecting segment number and polarity in *Drosophila*. Nature. Oct. 30, 1980;287(5785):795-801.
Paus et al., Telogen skin contains an inhibitor of hair growth. Br J Dermatol. Jun. 1990;122(6):777-84.
Pepinsky et al., Mapping sonic hedgehog-receptor interactions by steric interference. J Biol Chem. Apr. 14, 2000;275(15):10995-1001.
Romer et al., Targeting medulloblastoma: small-molecule inhibitors of the Sonic Hedgehog pathway as potential cancer therapeutics. Cancer Res. Jun. 15, 2005;65(12):4975-8.
Rosen et al., Inhibition of FKBP rotamase activity by immunosuppressant FK506: twisted amide surrogate. Science. May 18, 1990;248(4957):863-6.
Rubin et al., Targeting the Hedgehog pathway in cancer. Nat Rev Drug Discov. Dec. 2006;5(12):1026-33.
Sinha et al., Purmorphamine activates the Hedgehog pathway by targeting Smoothened. Nat Chem Biol. Jan. 2006;2(1):29-30. Epub Nov. 20, 2005.
Stanton et al., A small molecule that binds Hedgehog and blocks its signaling in human cells. Nat Chem Biol. Mar. 2009;5(3):154-6. Epub Jan. 18, 2009.
Stavenger et al., Asymmetric Catalysis in Diversity-Oriented Organic Synthesis: Enantioselective Synthesis of 4320 Encoded and Spatially Segregated Dihydropyrancarboxamides. Angew Chem Int Ed Engl. Sep. 17, 2001;40(18):3417-3421.
Stecca et al., The therapeutic potential of modulators of the Hedgehog-Gli signaling pathway. J Biol. Nov. 6, 2002;1(2):9.1-9.4.
Stewart et al., Expression of the developmental Sonic hedgehog (Shh) signalling pathway is up-regulated in chronic lung fibrosis and the Shh receptor patched 1 is present in circulating T lymphocytes. J Pathol. Apr. 2003;199(4):488-95.
Tapaile et al., Effects of oncogenic mutations in Smoothened and Patched can be reversed by cyclopamine. Nature. Aug. 31, 2000;406(6799):1005-9.
Tenzen et al., The cell surface membrane proteins Cdo and Boc are components and targets of the Hedgehog signaling pathway and feedback network in mice. Dev Cell. May 2006;10(5):647-56. Epub Apr. 27, 2006.
Thayer et al., Hedgehog is an early and late mediator of pancreatic cancer tumorigenesis. Nature. Oct. 23, 2003;425(6960):851-6. Epub Sep. 14, 2003.
Wang et al., Hedgehog-regulated processing of Gli3 produces an anterior/posterior repressor gradient in the developing vertebrate limb. Cell. Feb. 18, 2000;100(4):423-34.
Weitzman, Agonizing hedgehog. J Biol. Nov. 6, 2002;1(2):7.1-7.5.
Wender et al., Total synthesis and initial biological evaluation of new B-ring-modified bryostatin analogs. Org Lett. Nov. 9, 2006;8(23):5299-302.
Wilson et al., New "hogs" in Hedgehog transport and signal reception. Cell. May 5, 2006;125(3):435-8.
Wong et al., Modular Synthesis and Preliminary Biological Evaluation of Stereochemically Diverse 1,3-Dioxanes. Chem Biol. 2004;11:1279-91.
Wu et al., Purmorphamine induces osteogenesis by activation of the hedgehog signaling pathway. Chem Biol. Sep. 2004;11(9):1229-38.
Yao et al., The ihog cell-surface proteins bind Hedgehog and mediate pathway activation. Cell. Apr. 21, 2006;125(2):343-57.
Zhang et al., Kinetic and structural studies on interactions between heparin or heparan sulfate and proteins of the hedgehog signaling pathway. Biochemistry. Apr. 3, 2007;46(13):3933-41. Epub Mar. 10, 2007.

* cited by examiner

SONIC HEDGEHOG MODULATORS

CROSS REFERENCE TO RELATED APPLICATIONS

The present application is a national stage filing under 35 U.S.C. §371 of international PCT application, PCT/US2009/041295, filed Apr. 21, 2009, which claims priority under 35 U.S.C. §119(e) to U.S. provisional applications, U.S. Ser. No. 61/097,770, filed Sep. 17, 2008, and U.S. Ser. No. 61/046,710, filed Apr. 21, 2008, each of which is incorporated herein by reference.

This invention was made with Government support under GM038627, CO012400, and HG005032 awarded by the National Institutes of Health. The Government has certain rights in the invention.

FIELD OF THE INVENTION

The present invention relates to macrocyclic small molecule modulators of the Sonic Hedgehog signaling pathway, syntheses thereof, and intermediates thereto. The invention also provides pharmaceutical compositions comprising compounds of the present invention and methods of using said compounds in the treatment of proliferative diseases (e.g., benign neoplams, cancers, inflammatory diseases, autoimmune diseases, diabetic retinopathy), pulmonary diseases, and developmental disorders.

BACKGROUND OF THE INVENTION

The Hedgehog (Hh) pathway has been implicated in many developmental processes, including organogenesis in most animals (Ingham, P. W., McMahon, A. P. *Genes and Dev.* 15, 3059-3087, 2001; Frank-Kamenetsky, M., et al. *J. Biol.* 10, 1-19, 2002). First identified in *Drosophila* in 1980, three mammalian homologues of Hh proteins, Sonic Hedgehog (Shh), Desert Hedgehog, (Dhh), and Indian Hedgehog (Ihh), are all key regulators of anterior/posterior patterning in limb development, the induction of polarity in the central nervous system, and the differentiation of numerous cell types (Nusslein-Volhard, C., Wieschaus, E. *Nature* 287, 795-801, 1980); Weitzman, J. B. *J. Biol.* 7, 1-5, 2002; Pepinsky, R. B. et al. *J. Biol. Chem.* 275, 10995-11001, 2000; Stecca, B., Altaba, A. R. *J. Biol.* 9, 1-4, 2002). Shh is the most widely characterized of the Hh homologues and is essential for proper embryonic development. The Shh pathway involves the auto-cleavage of full length Shh into an active 20 kD N-terminal fragment (ShhN), which binds to its 7-pass transmembrane receptor, Patched (Ptc1), reversing its inhibitory effect on Smoothened (Smo) (Goetz, J. A., Singh, S., Suber, L. M., Robbins, D. J. *J. Biol. Chem.* 281, 4087-4093, 2006). One effect of this de-repression is the activation of Gli transcription factors, which regulate the transcription of target genes that include Gli1 and Ptc1.

There have been several reports of both synthetic and natural small-molecule modulators of the Shh signaling pathway, discovered through cell-based phenotypic screens (Rubin, L., de Sauvage, F. J. *Nature* 5, 1026-1033, 2006; Chen, J. K., Tapaile, J., Young, K. E., Maiti, T., Beachy, P. A. *PNAS* 99, 14071-14076, 2002). Reported Shh signaling antagonists include teratogenic natural products such as cyclopamine, jervine, AY9944, and tripanol, as well as synthetic molecules such as SANT1 and Cur-6141 (Cooper, M. K., Porter, J. A., Young, K. E., Beachy, P. A. *Science* 280, 1603-1607, 1998; Tapaile, J., et al. *Nature* 406, 1005-1009, 2000). There have also been reports of synthetic small-molecule agonists of the Shh pathway, including purmorphamine and Hh-Ag1.2 (Ding, S., Schultz, P. G. *Nat. Biotechnol.* 7, 833-840, 2004; Wu, X. et al. *Chem. Biol.* 11, 1229-1238, 2004). The discovery of chemical modulators of Shh signaling provides a potential means to regulate the activity of a pathway that can result in proliferative diseases (e.g., medulloblastoma, basal cell carcinomas, or pancreatic cancer), pulmonary diseases (Coon, D. R. et al. *Exp. Mol. Pathol.* 80, 119-123, 2006; Stewart, G. A. et al. *J. Pathol.* 199, 488-495, 2003) and developmental disorders (Wang, B., Fallon, J. F., Beachy, P. A. *Cell* 100, 423-434, 2000; Borycki, A. G., Mendham, L., Emerson, C. P., Jr. *Development* 125, 777-790, 1998; Chiang, C. et al. *Nature* 383, 407-413, 1996; Kayed, H. et al. *Pancreas* 32, 119-129, 2006; Furukawa, T., Sunumura, M., Hori, A. *Cancer Sci.*, 97, 1-7, 2006; Thayer, S. P. et al. *Nature* 425, 851-856, 2003).

SUMMARY OF THE INVENTION

The present invention encompasses the recognition that small molecule modulators of the Shh signaling pathway are useful in the treatment of proliferative diseases, pulmonary diseases, and developmental disorders. Novel macrocylic compounds are provided that inhibit Sonic Hedgehog induced-protein transcription.

In one aspect, the invention provides compounds of formula I:

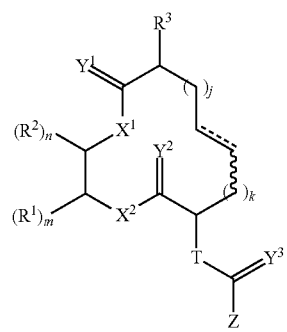

or a pharmaceutically acceptable salt thereof, wherein:
≡ designates a single or double bond;
$X^1$ and $X^2$ are each independently —$CR_2$—, —O—, —S—, or —NR—;
$Y^1$, $Y^2$, and $Y^3$ are each independently =O, =NR, or =S;
Z is —$NR^4R^5$, —$OR^5$, or —$SR^5$;
T is a covalent bond or a bivalent $C_{1-12}$ saturated or unsaturated, straight or branched, aliphatic or heteroaliphatic chain;
j is an integer from 0 to 4, inclusive;
k is an integer from 0 to 4, inclusive;
the sum of j and k is an integer from 0 to 5, inclusive;
m is an integer from 0 to 2, inclusive;
n is an integer from 0 to 2, inclusive;
each occurrence of $R^1$ is independently hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two $R^1$ groups may be taken together with their intervening atoms to form a 3-8-membered ring; or when $X^2$ is —NR—, $R^1$ and the R of —NR— may be taken together with their intervening atoms to form a 3-8-membered ring;

each occurrence of $R^2$ is independently hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; or 4-7-membered heterocyclyl having 1-2 heteroatoms independently selected from nitrogen, oxygen, or sulfur; or two $R^2$ groups may be taken together with their intervening atoms to form a 3-8-membered ring;

$R^3$ is hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;

$R^4$ is hydrogen, —OR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;

$R^5$ is hydrogen or —$C(R^6)_3$; or, when $R^5$ is —$C(R^6)_3$, $R^4$ and $R^5$ may be taken together with their intervening atoms to form a 3-8-membered ring;

each occurrence of $R^6$ is independently hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two occurrences of $R^6$ may be taken together with their intervening atoms to form a 3-8-membered ring; and each R is independently hydrogen, a protecting group, an acyl moiety, arylalkyl moiety, aliphatic moiety, aryl moiety, heteroaryl moiety, or heteroaliphatic moiety; or:

two R on the same nitrogen atom may be taken with the nitrogen to form a 4-7-membered heterocyclic ring having 1-2 heteroatoms independently selected from nitrogen, oxygen, or sulfur.

The invention also provides pharmaceutical compositions comprising a compound of the invention and a pharmaceutically acceptable carrier. In certain embodiments, the pharmaceutical composition comprises a therapeutically effective amount of the compound to treat a proliferative disease, pulmonary disease, or a developmental disorder.

According to another aspect, the invention provides a method for the inhibition of Sonic Hedgehog protein-induced transcription in a cell, the method comprising contacting the cell with an effective amount of a compound of formula I to inhibit the Shh pathway. In certain embodiments, a compound of formula I inhibits the Shh pathway upstream of Ptc1. In certain embodiments, a compound of formula I destabilizes a dimeric Shh complex.

According to one aspect, the present invention provides a method of treating a proliferative disease in a subject suffering therefrom, the method comprising administering to the subject a therapeutically effective amount of a compound of formula I. In some embodiments, the proliferative disease is cancer. In some embodiments, the cancer is a benign neoplasm. In certain embodiments, the cancer is basal cell carcinoma, Gorlin syndrome, medulloblastoma, or pancreatic cancer. In some embodiments, the proliferative disease is an inflammatory disease.

According to one aspect, the present invention provides a method of treating a developmental disorder in a subject suffering therefrom, the method comprising administering to the subject a therapeutically effective amount of a compound of formula I. In certain embodiments, the developmental disorder is phocomelia or cyclopia.

According to one aspect, the present invention provides a method of treating a pulmonary disease in a subject suffering therefrom, the method comprising administering to the subject a therapeutically effective amount of a compound of formula I. In certain embodiments, the pulmonary disease is interstitial pnuemonitis or interstitial pulmonary fibrosis.

According to one aspect, the present invention provides a method of controlling stem cell differentiation, wherein the method comprises contacting one or more stem cells with a compound of formula I.

According to one aspect, the present invention provides a method of synthesizing an inventive compound comprising the steps of:

(a) providing a compound of formula i:

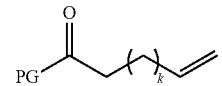

wherein k is an integer from 0 to 4, inclusive; and PG is a suitable protecting group;

(b) reacting the compound of formula i with an ester of formula ii:

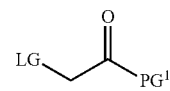

wherein $PG^1$ is a suitable protecting group and LG is a suitable leaving group;

under suitable conditions to yield a compound of formula iii:

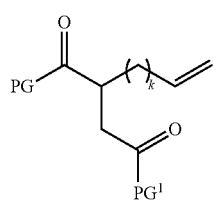

(c) deprotecting the compound of formula iii under suitable conditions to remove PG¹ to form a carboxylic acid of formula iv:

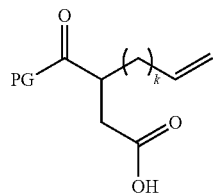

iv (d) reacting the compound of formula iv under suitable coupling conditions with a nucleophile to form a compound of formula v:

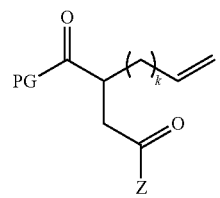

v wherein,
Z is —NR⁴R⁵, —OR⁵, or —SR⁵;
R⁴ is hydrogen, —OR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;
R⁵ is hydrogen or —C(R⁶)₃; or, when R⁵ is —C(R⁶)₃, R⁴ and R⁵ may be taken together with their intervening atoms to form a 3-8-membered ring;
each occurrence of R⁶ is independently hydrogen, halogen, —CN, —SCN, —NO₂, —CO₂R, —SOR, —SO₂R, —NR₂, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or
two occurrences of R⁶ may be taken together with their intervening atoms to form a 3-8-membered ring; and
each R is independently hydrogen, a protecting group, an acyl moiety, arylalkyl moiety, aliphatic moiety, aryl moiety, heteroaryl moiety, or heteroaliphatic moiety; or:
two R on the same nitrogen atom may be taken with the nitrogen to form a 4-7-membered heterocyclic ring having 1-2 heteroatoms independently selected from nitrogen, oxygen, or sulfur;
(e) deprotecting the compound of formula v under suitable conditions to remove PG to form a carboxylic acid of formula vi:

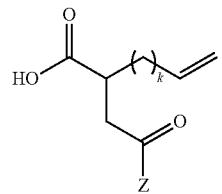

vi (f) conjugating a carboxylic acid of formula vi under suitable conditions with an amino alcohol of formula vii:

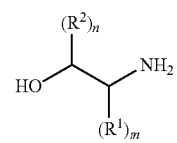

vii wherein m is an integer from 0 to 2, inclusive;

n is an integer from 0 to 2, inclusive;

each occurrence of R¹ is independently hydrogen, halogen, —CN, —SCN, —NO₂, —CO₂R, —SOR, —SO₂R, —NR₂, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two R¹ groups may be taken together with their intervening atoms to form a 3-8-membered ring; or when X² is —NR—, R¹ and the R of —NR— may be taken together with their intervening atoms to form a 3-8-membered ring;

each occurrence of R² is independently hydrogen, halogen, —CN, —SCN, —NO₂, —CO₂R, —SOR, —SO₂R, —NR₂, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two R² groups may be taken together with their intervening atoms to form a 3-8-membered ring; and each R is independently hydrogen, a protecting group, an acyl moiety, arylalkyl moiety, aliphatic moiety, aryl moiety, heteroaryl moiety, or heteroaliphatic moiety; or:
two R on the same nitrogen atom may be taken with the nitrogen to form a 4-7-membered heterocyclic ring having 1-2 heteroatoms independently selected from nitrogen, oxygen, or sulfur;

to form an alcohol of formula viii:

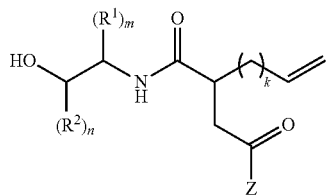

(g) reacting the alcohol of formula viii under suitable conditions with a carboxylic acid of formula ix:

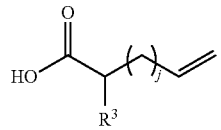

wherein, j is an integer from 0 to 4, inclusive;

$R^3$ is hydrogen, halogen, —CN, —SCN, —NO$_2$, —CO$_2$R, —SOR, —SO$_2$R, —NR$_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; and each R is independently hydrogen, a protecting group, an acyl moiety, arylalkyl moiety, aliphatic moiety, aryl moiety, heteroaryl moiety, or heteroaliphatic moiety; or:

two R on the same nitrogen atom may be taken with the nitrogen to form a 4-7-membered heterocyclic ring having 1-2 heteroatoms independently selected from nitrogen, oxygen, or sulfur;

to form an ester of formula x:

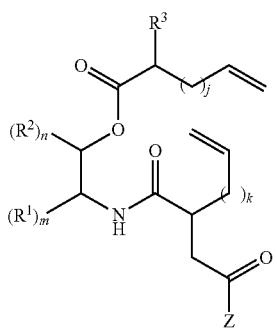

and (h) reacting ester of formula x under suitable conditions in the presence of a suitable ring closing metathesis catalyst to form a macrocycle of formula xi:

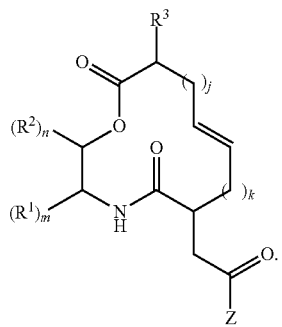

The entire contents of all references cited above and herein are hereby incorporated by reference.

BRIEF DESCRIPTION OF THE DRAWINGS

FIG. 7 shows that the treated tissue displayed reduced levels of Gli1 and Gli2 mRNA (left and center panels) while remaining histologically normal (right panel).

FIG. 8b shows the results of RT-PCR analysis of Gli1 and Gli2 expression levels from harvested skin in treated and untreated mice.

DETAILED DESCRIPTION OF CERTAIN EMBODIMENTS

Figure 1:
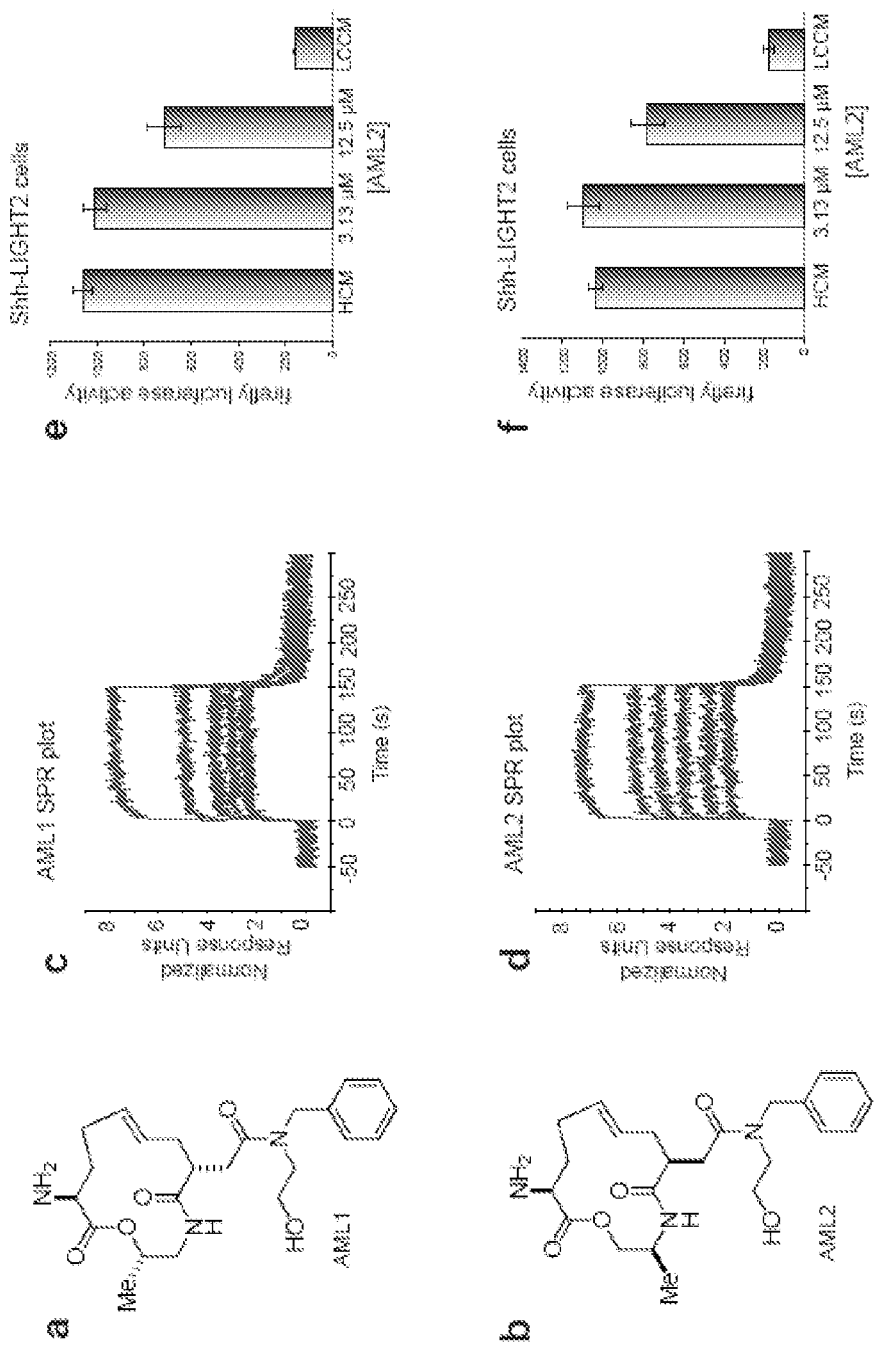
FIG. 1 depicts the characterization of two small molecules (AML1 and AML2) found to bind to purified ShhN (a and b); surface plasmon resonance (SPR) plots of AML1 and AML2, respectively, binding to purified ShhN (c and d); and luminescence plots for a Gli-dependent firefly luciferase reporter gene assay (e and f).

Nature has evolved many macrolactone natural products with unique activities and specificities, many of which are naturally prepared by the polyketide synthase family of enzymes (Kittendorf, J. D.; Beck, B. J.; Buchholz, T. J.; Seufert, W.; Sherman, D. H. *Cell* 2007, 14, 944-954; Gokhale, R. S.; Hunziker, D.; Cane, D. E.; Khosla, C. Chem. And Biol. 1999, 6, 117-125). Pertinent examples include erythromycin (antibiotic), amphotericin B (anti-fungal) (Matsumori, N.; Sawada, Y.; Murata, M. *J. Am. Chem. Soc.* 2005, 127, 10667-10675), bryostatin-1 (anti-cancer) (Wender, P. A.; Horan, J. C.; Verma, V. A. *Org. Lett.* 2006, 8, 5299-5302), and FK506 (immunosuppressant) (Harding, M. W.; Galat, A.; Uehling, D. E.; Schreiber, S. L. *Nature*, 1989, 341, 758-760; Nakatsuka, M.; Ragan, J. A.; Sammakia, T.; Smith, D. B.; Uehling, D. E.; Schreiber, S. L. *J. Am. Chem. Soc.*, 1990, 112, 5583-5601; Rosen, M. K.; Standaert, R. F.; Galat, A.; Nakatsuka, M.; Schreiber, S. L. *Science*, 1990, 248, 863-866). The present invention provides a new class of non-naturally occurring macrocycles capable of binding to purified Sonic Hedgehog (Shh) protein and repressing target gene expression associated with the Shh pathway in cells. As disclosed herein, subtle patterns exist in the relationship between ring size, stereochemistry, and the biological activities of the inventive compounds. In certain embodiments, provided compounds are useful to treat proliferative diseases, pulmonary diseases, and developmental disorders.

Compounds

Compounds of this invention include those described generally above and are further illustrated by the classes, subclasses, and species disclosed herein. In some embodiments, provided compounds are macrocyclic small molecule modulators of the Sonic Hedgehog signaling pathway. For the purposes of this invention, the chemical elements are identified in accordance with the Periodic Table of the Elements, CAS version, *Handbook of Chemistry and Physics*, 75th Ed. Additionally, general principles of organic chemistry are described in *Organic Chemistry*, Thomas Sorrell, University Science Books, Sausalito: 1999, and *March's Advanced Organic Chemistry*, 5th Ed, Ed.: Smith, M. B. and March, J., John Wiley & Sons, New York: 2001, the entire contents of which are hereby incorporated by reference.

Description of Exemplary Compounds

In certain embodiments, the present invention provides compounds of formula I:

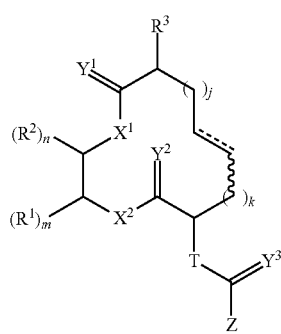

I or a pharmaceutically acceptable salt thereof, wherein:

⹀ designates a single or double bond;

$X^1$ and $X^2$ are each independently —$CR_2$—, —O—, —S—, or —NR—;

$Y^1$, $Y^2$, and $Y^3$ are each independently =O, =NR, or =S;

Z is —$NR^4R^5$, —$OR^5$, or —$SR^5$;

T is a covalent bond or a bivalent $C_{1-12}$ saturated or unsaturated, straight or branched, aliphatic or heteroaliphatic chain;

j is an integer from 0 to 4, inclusive;

k is an integer from 0 to 4, inclusive;

the sum of j and k is an integer from 0 to 5, inclusive;

m is an integer from 0 to 2, inclusive;

n is an integer from 0 to 2, inclusive;

each occurrence of $R^1$ is independently hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two $R^1$ groups may be taken together with their intervening atoms to form a 3-8-membered ring; or when $X^2$ is —NR—, $R^1$ and the R of —NR— may be taken together with their intervening atoms to form a 3-8-membered ring;

each occurrence of $R^2$ is independently hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two $R^2$ groups may be taken together with their intervening atoms to form a 3-8-membered ring;

$R^3$ is hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;

$R^4$ is hydrogen, —OR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;

$R^5$ is hydrogen or —$C(R^6)_3$; or, when $R^5$ is —$C(R^6)_3$, $R^4$ and $R^5$ may be taken together with their intervening atoms to form a 3-8-membered ring;

each occurrence of $R^6$ is independently hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two occurrences of $R^6$ may be taken together with their intervening atoms to form a 3-8-membered ring; and each R is independently hydrogen, a protecting group, an acyl moiety, arylalkyl moiety, aliphatic moiety, aryl moiety, heteroaryl moiety, or heteroaliphatic moiety; or:

two R on the same nitrogen atom may be taken with the nitrogen to form a 4-7-membered heterocyclic ring having 1-2 heteroatoms independently selected from nitrogen, oxygen, or sulfur.

As defined above, ≡ represents a single or double bond. It will be appreciated that compounds of formula I can be subjected to hydrogenation conditions that reduce a double bond to a single bond. In some embodiments, ≡ represents a single bond. In other embodiments, ≡ represents a double bond. In some embodiments, ≡ represents a trans double bond. In some embodiments, ≡ represents a cis double bond.

As defined above, $X^1$ and $X^2$ are each independently —$CR_2$—, —O—, —S—, or —NR—. In some embodiments, $X^1$ is —O—. In some embodiments, $X^2$ is —O—. In some embodiments, $X^1$ is —NR—. In some embodiments, $X^2$ is —NR—. In some embodiments, $X^1$ is —$CR_2$—. In some embodiments, $X^2$ is —$CR_2$—. In some embodiments, $X^1$ is —S—. In some embodiments, $X^2$ is —S—. In some embodiments, one of $X^1$ and $X^2$ is —O— while the other is —NH—. In some embodiments, $X^1$ and $X^2$ are not —$CR_2$—. In some embodiments, $X^1$ is —O— and $X^2$ is —NR—. In some embodiments, $X^1$ is —NR— and $X^2$ is —O—.

In certain embodiments, $Y^1$, $Y^2$, and $Y^3$ are each independently =, =NR, or =S. In some embodiments, $Y^1$, $Y^2$, and $Y^3$ are =O. In some embodiments, $Y^1$ and $Y^2$ are =O. In certain embodiments, both $Y^1$ and $Y^2$ are =O, $X^1$ is —NH—, and $X^2$ is —O—. In certain embodiments, both $Y^1$ and $Y^2$ are =O, $X^1$ is —O—, and $X^2$ is —NH—.

In certain embodiments, T is a covalent bond or a bivalent $C_{1-12}$ saturated or unsaturated, straight or branched, aliphatic or heteroaliphatic chain. In some embodiments, T is a covalent bond. In other embodiments, T is a bivalent $C_{1-12}$ saturated or unsaturated, straight or branched, aliphatic chain. In some embodiments, T is a bivalent $C_{1-12}$ saturated or unsaturated, straight or branched, heteroaliphatic chain. In other embodiments, T is a bivalent $C_{1-6}$ saturated or unsaturated, straight or branched, aliphatic chain. In some embodiments, T is a bivalent $C_{1-6}$ saturated or unsaturated, straight or branched, heteroaliphatic chain. In certain embodiments, T is —$CH_2$—, —$(CH_2)_2$—, or —$(CH_2)_3$—. In some embodiments, T is —$CH_2$—.

As defined above, j is an integer from 0 to 4, inclusive. In some embodiments, j is an integer from 1 to 3, inclusive. In some embodiments, j is 0. In some embodiments, j is 1. In some embodiments, j is 2. In some embodiments, j is 3. In some embodiments, j is 4.

As defined above, k is an integer from 0 to 4, inclusive. In some embodiments, k is an integer from 1 to 3, inclusive. In some embodiments, k is 0. In some embodiments, k is 1. In some embodiments, k is 2. In some embodiments, k is 3. In some embodiments, k is 4.

In certain embodiments, the sum of j and k is an integer from 0 to 5, inclusive. In some embodiments, the sum of j and k is 0. In some embodiments, the sum of j and k is 1. In some embodiments, the sum of j and k is 2. In some embodiments, the sum of j and k is 3. In some embodiments, the sum of j and k is 4. In some embodiments, the sum of j and k is 5.

In some embodiments, j is 1 and k is 1. In some embodiments, j is 0 and k is 1. In some embodiments, j is 2 and k is 1. In some embodiments, j is 1 and k is 0. In some embodiments, j is 0 and k is 0. In some embodiments, j is 2 and k is 0. In some embodiments, j is 1 and k is 2. In some embodiments, j is 0 and k is 2. In some embodiments, j is 2 and k is 2.

In certain embodiments, each occurrence of $R^1$ is independently hydrogen, halogen, —$NR_2$, —OR, or —SR. In certain embodiments, each occurrence of $R^1$ is independently an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur.

In some embodiments, $R^1$ is hydrogen. In some embodiments, $R^1$ is optionally substituted $C_{1-12}$ aliphatic. In some embodiments, $R^1$ is optionally substituted $C_{1-6}$ aliphatic. In some embodiments, $R^1$ is optionally substituted $C_{1-6}$ alkyl. In some embodiments, $R^1$ is optionally substituted $C_{1-12}$ heteroaliphatic. In some embodiments, $R^1$ is optionally substituted $C_{7-15}$ arylalkyl. In some embodiments, $R^1$ is benzyl. In some embodiments, $R^1$ is optionally substituted $C_{3-15}$ heteroarylalkyl. In some embodiments, $R^1$ is optionally substituted 6-10-membered aryl. In some embodiments, $R^1$ is substituted or unsubstituted phenyl. In some embodiments, $R^1$ is unsubstituted phenyl. In some embodiments, $R^1$ is optionally substituted 5-10-membered heteroaryl having 1-4 heteroatoms independently selected from nitrogen, oxygen, or sulfur; or 4-7-membered heterocyclyl having 1-2 heteroatoms independently selected from nitrogen, oxygen, or sulfur. In some embodiments, $R^1$ is optionally substituted acyl.

In some embodiments, m is 0. In some embodiments, m is 1. In other embodiments, m is 2. In certain embodiments, two $R^1$ groups may be taken together with their intervening atoms to form a 3-8-membered ring. In some embodiments, two $R^1$ groups may be taken together with their intervening atoms to form a 4-6-membered ring. In some embodiments, two $R^1$ groups may be taken together with their intervening atoms to form a 5-membered ring. In some embodiments, two $R^1$ groups may be taken together with their intervening atoms to form a 6-membered ring.

In some embodiments, when $X^2$ is —NR—, $R^1$ and the R of —NR— may be taken together with their intervening atoms to form a 3-8-membered ring. In some embodiments, $R^1$ and the R of —NR— may be taken together with their intervening atoms to form a 5-membered ring. In some embodiments, $R^1$ and the R of —NR— may be taken together with their intervening atoms to form a 6-membered ring.

Exemplary $R^1$ groups of compounds of formula I are set forth in Table 1, below.

TABLE 1

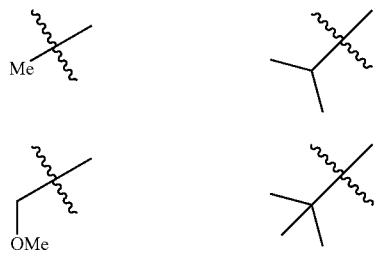

TABLE 1-continued

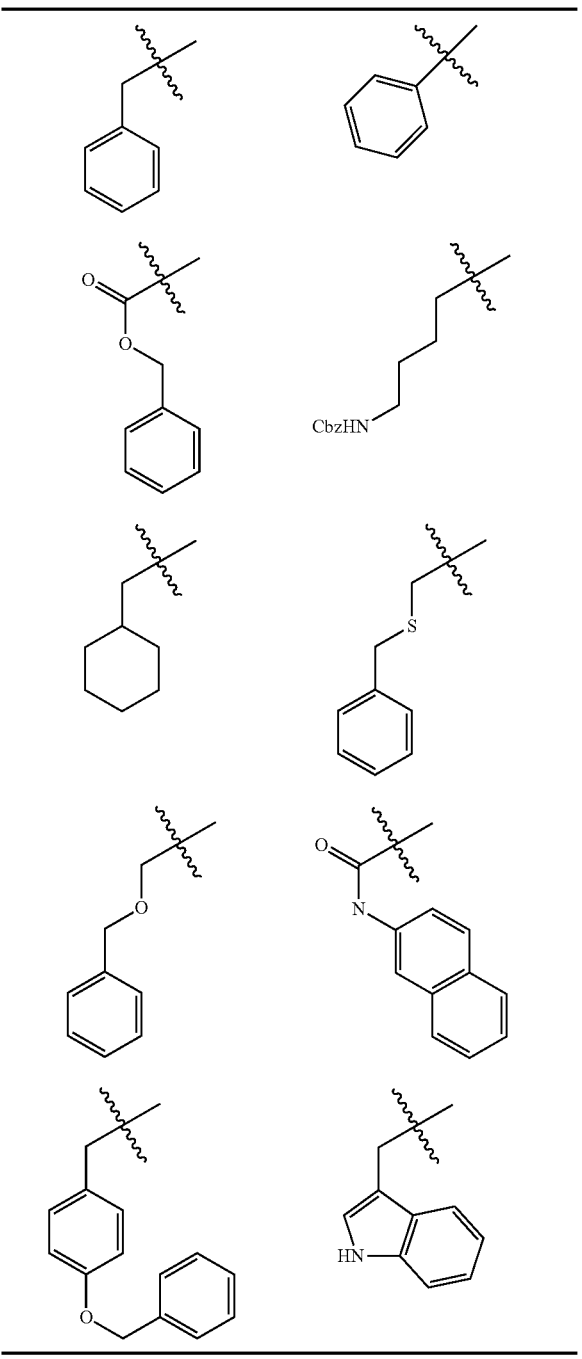

In certain embodiments, each occurrence of $R^2$ is independently hydrogen, halogen, —$NR_2$, —OR, or —SR. In certain embodiments, each occurrence of $R^2$ is independently an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur.

In some embodiments, $R^2$ is hydrogen. In some embodiments, $R^2$ is optionally substituted $C_{1-12}$ aliphatic. In some embodiments, $R^2$ is optionally substituted $C_{1-12}$ heteroaliphatic. In some embodiments, $R^2$ is optionally substituted $C_{7-15}$ arylalkyl. In some embodiments, $R^2$ is benzyl. In some embodiments, $R^2$ is optionally substituted $C_{3-15}$ heteroarylalkyl. In some embodiments, $R^2$ is optionally substituted 6-10-membered aryl. In some embodiments, $R^2$ is substituted or unsubstituted phenyl. In some embodiments, $R^2$ is unsubstituted phenyl. In some embodiments, $R^2$ is optionally substituted 5-10-membered heteroaryl having 1-4 heteroatoms independently selected from nitrogen, oxygen, or sulfur; or 4-7-membered heterocyclyl having 1-2 heteroatoms independently selected from nitrogen, oxygen, or sulfur. In some embodiments, $R^2$ is methyl. In some embodiments, $R^2$ is phenyl.

In some embodiments, n is 0. In some embodiments, n is 1. In other embodiments, n is 2. In certain embodiments, two $R^2$ groups may be taken together with their intervening atoms to form a 3-8-membered ring. In some embodiments, two $R^2$ groups may be taken together with their intervening atoms to form a 4-6-membered ring. In some embodiments, two $R^2$ groups may be taken together with their intervening atoms to form a 5-membered ring. In some embodiments, two $R^2$ groups may be taken together with their intervening atoms to form a 6-membered ring.

In some embodiments, at least one of $R^1$ and $R^2$ is hydrogen. In some embodiments, both $R^1$ and $R^2$ are not hydrogen.

In certain embodiments, $R^3$ is hydrogen, halogen, —$NR_2$, —OR, or —SR. In certain embodiments, $R^3$ is an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur.

In some embodiments, $R^3$ is hydrogen. In some embodiments, $R^3$ is halogen. In some embodiments, $R^3$ is —$NR_2$. In some embodiments, $R^3$ is —$NH_2$. In some embodiments, $R^3$ is —OR. In some embodiments, $R^3$ is optionally substituted $C_{1-12}$ aliphatic. In some embodiments, $R^3$ is optionally substituted $C_{1-12}$ heteroaliphatic. In some embodiments, $R^3$ is optionally substituted $C_{7-15}$ arylalkyl. In some embodiments, $R^3$ is optionally substituted $C_{3-15}$ heteroarylalkyl. In some embodiments, $R^3$ is optionally substituted 6-10-membered aryl. In some embodiments, $R^3$ is optionally substituted 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur.

In certain embodiments, $R^3$ is

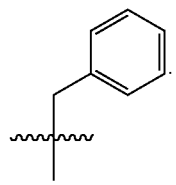 [SMILES: *Cc1ccccc1]

In certain embodiments, $R^3$ is

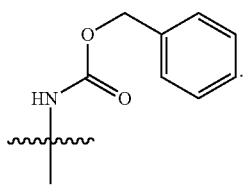 [SMILES: *NC(=O)OCc1ccccc1]

In certain embodiments, $R^3$ is

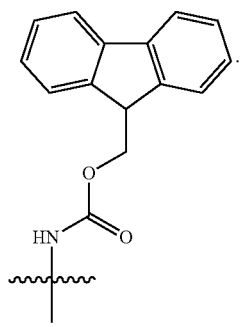 [SMILES: *NC(=O)OCC1c2ccccc2-c2ccccc21]

In certain embodiments, Z is —$OR^5$. In certain embodiments, Z is —$SR^5$. In certain embodiments, Z is —$NR^4R^5$. In certain embodiments, Z is —$NHR^5$.

In certain embodiments, $R^4$ is hydrogen or —OR. In certain embodiments, $R^4$ is an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur.

In some embodiments, $R^4$ is hydrogen. In some embodiments, $R^4$ is —OR. In some embodiments, $R^4$ is optionally substituted $C_{1-12}$ aliphatic. In some embodiments, $R^4$ is optionally substituted $C_{1-12}$ heteroaliphatic. In some embodiments, $R^4$ is optionally substituted $C_{7-15}$ arylalkyl. In some embodiments, $R^4$ is optionally substituted $C_{3-15}$ heteroarylalkyl. In some embodiments, $R^4$ is optionally substituted 6-10-membered aryl. In some embodiments, $R^4$ is optionally substituted 5-10-membered heteroaryl having 1-4 heteroatoms independently selected from nitrogen, oxygen, or sulfur; or 4-7-membered heterocyclyl having 1-2 heteroatoms independently selected from nitrogen, oxygen, or sulfur.

In certain embodiments, $R^4$ is —$CH_2CH_2OH$. In certain embodiments, $R^4$ is other than —$CH_2CH_2OH$.

In certain embodiments, $R^5$ is hydrogen. In other embodiments, $R^5$ is —$C(R^6)_3$. In some embodiments, $R^5$ is —$CH_2R^6$. In some embodiments, when $R^5$ is —$C(R^6)_3$, $R^4$ and $R^5$ may be taken together with their intervening atoms to form a 3-8-membered ring. In some embodiments, when $R^5$ is —$C(R^6)_3$, $R^4$ and $R^5$ may be taken together with their intervening atoms to form a 4-6-membered ring. In some embodiments, when $R^5$ is —$C(R^6)_3$, $R^4$ and $R^5$ may be taken together with their intervening atoms to form a 5-membered ring. In some embodiments, when $R^5$ is —$C(R^6)_3$, $R^4$ and $R^5$ may be taken together with their intervening atoms to form a 6-membered ring.

In some embodiments, each occurrence of $R^6$ is independently hydrogen or halogen. In some embodiments, each occurrence of $R^6$ is an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur.

In certain embodiments, $R^6$ is optionally substituted acyl. In certain embodiments, $R^6$ is optionally substituted $C_{1-12}$ aliphatic. In certain embodiments, $R^6$ is optionally substituted $C_{1-12}$ heteroaliphatic. In certain embodiments, $R^6$ is optionally substituted $C_{7-15}$ arylalkyl. In certain embodiments, $R^6$ is optionally substituted $C_{3-15}$ heteroarylalkyl. In certain embodiments, $R^6$ is optionally substituted 6-10-membered aryl. In certain embodiments, $R^6$ is optionally substituted 5-10-membered heteroaryl having 1-4 heteroatoms independently selected from nitrogen, oxygen, or sulfur; or 4-7-membered heterocyclyl having 1-2 heteroatoms independently selected from nitrogen, oxygen, or sulfur.

In some embodiments, one occurrence of $R^6$ is an optionally substituted $C_{1-6}$ aliphatic group. In some embodiments, one occurrence of $R^6$ is an optionally substituted $C_{1-6}$ alkyl group. In some embodiments, two occurrences of $R^6$ are optionally substituted $C_{1-6}$ aliphatic groups. In certain embodiments, two occurrences of $R^6$ may be taken together with their intervening atoms to form a 3-8-membered ring. In certain embodiments, two occurrences of $R^6$ may be taken together with their intervening atoms to form a 4-6-membered ring. In certain embodiments, two occurrences of $R^6$ may be taken together with their intervening atoms to form a 5-membered ring. In certain embodiments, two occurrences of $R^6$ may be taken together with their intervening atoms to form a 6-membered ring.

In certain embodiments, three occurrences of $R^6$ are independently optionally substituted $C_{1-6}$ aliphatic groups. In some embodiments, three occurrences of $R^6$ are methyl.

In some embodiments, two occurrences of $R^6$ are hydrogen. In some embodiments, one occurrence of $R^6$ is optionally substituted 6-10-membered aryl. In certain embodiments, one occurrence of $R^6$ is 4-chlorophenyl. In certain embodiments, one occurrence of $R^6$ is biphenyl-4-yl.

In some embodiments, one occurrence of $R^6$ is optionally substituted 5-10-membered heteroaryl having 1-4 heteroatoms independently selected from nitrogen, oxygen, or sulfur. In some embodiments, one occurrence of $R^6$ is optionally substituted 5-6-membered heteroaryl having 1-2 heteroatoms independently selected from nitrogen or sulfur. In some embodiments, one occurrence of $R^6$ is optionally substituted pyridyl. In some embodiments, one occurrence of $R^6$ is optionally substituted furanyl. In some embodiments, one occurrence of $R^6$ is optionally substituted imidazolyl. In some embodiments, one occurrence of $R^6$ is optionally substituted thiazolyl. In some embodiments, one occurrence of $R^6$ is optionally substituted oxazolyl. In some embodiments, one occurrence of $R^6$ is

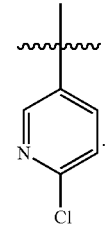

In some embodiments, one occurrence of $R^6$ is

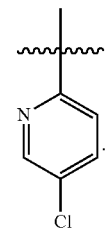

In some embodiments, one occurrence of $R^6$ is

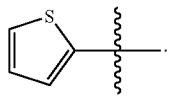 [SMILES: *c1cccs1]

In some embodiments, one occurrence of $R^6$ methyl. In some embodiments, one occurrence of $R^6$ is —$CH_2OH$. In some embodiments, one occurrence of $R^6$ is —$CH_2OCH_2CH_2OH$. In some embodiments, one occurrence of $R^6$ is phenyl. In some embodiments, one occurrence of $R^6$ is

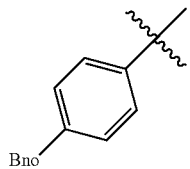

In some embodiments, $R^6$ is other than —$CH_2OH$. In some embodiments, $R^6$ is other than —$CH_2OCH_2CH_2OH$.

In some embodiments, R is hydrogen. In some embodiments, R is a protecting group. In some embodiments R is an acyl moiety. In some embodiments, R is an arylalkyl moiety. In some embodiments, R is an aryl moiety. In some embodiments, R is a heteroaryl moiety. In some embodiments, R is an aliphatic moiety. In some embodiments, R is a heteroaliphatic moiety. In some embodiments, R is an optionally substituted $C_{1-6}$ alkyl group. In some embodiments R is methyl. In some embodiments R is ethyl. In some embodiments R is propyl. In some embodiments R is butyl.

As described above, in certain embodiments, $Y^1$, $Y^2$, and $Y^3$ are =O, $X^1$ is —O—, and $X^2$ is —NR—. In certain embodiments, provided compounds are of formula II-a:

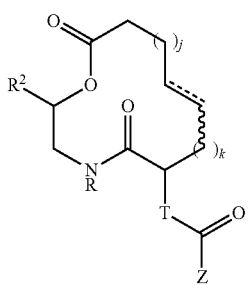

II-a wherein each of j, k, T, Z, R, and $R^2$ is as defined above and described in classes and subclasses herein.

As described above, in certain embodiments, $Y^1$, $Y^2$, and $Y^3$ are =O, $X^1$ is —NR—, and $X^2$ is —O—. In certain embodiments, provided compounds are of formula II-b:

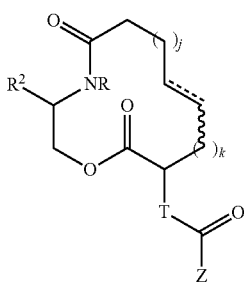

II-b wherein each of j, k, T, Z, R, and $R^2$ is as defined above and described in classes and subclasses herein.

As described above, in certain embodiments, === designates a double bond and k is 1. In some embodiments, such compounds are of formula III-a or III-b:

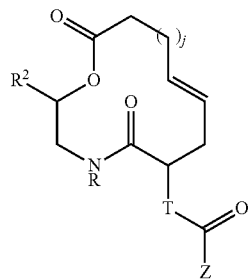

III-a

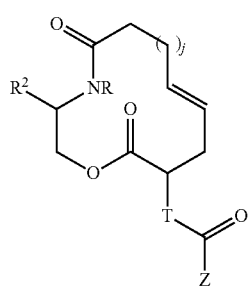

III-b wherein j is an integer from 1 to 3, inclusive; and each of T, Z, R, and $R^2$ is as defined above and described in classes and subclasses herein.

In certain embodiments, such compound are of formula III-c, III-d, III-e, or III-f:

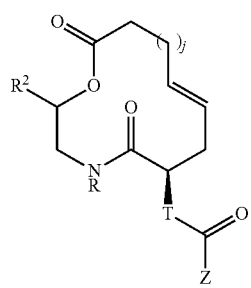

III-c

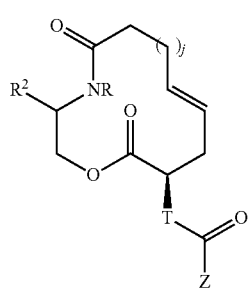

III-d

III-e

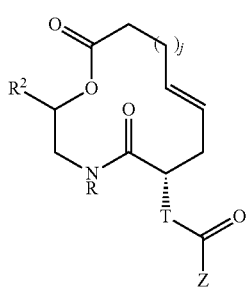

III-f

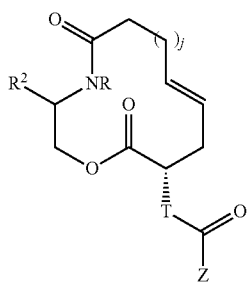

In certain embodiments, j is an integer from 1 to 3, inclusive. In certain embodiments, j is 1. In certain embodiments, j is 2. In certain embodiments, j is 3.

In some embodiments, T is a bivalent $C_{1-12}$ saturated or unsaturated, straight or branched, aliphatic or heteroaliphatic chain. In some embodiments, T is methylene.

In some embodiments, $R^2$ is optionally substituted $C_{1-12}$ aliphatic. In some embodiments, $R^2$ is optionally substituted 6-10-membered aryl. In some embodiments, $R^2$ is methyl. In some embodiments, $R^2$ is phenyl.

In certain embodiments, Z is —$NR^4R^5$, and $R^4$ is hydrogen. In some embodiments, $R^5$ is —$C(R^6)_3$ and each occurrence of $R^6$ is independently hydrogen or an optionally substituted selected from the group consisting of $C_{7-15}$ arylalkyl; $C_{3-15}$ heteroarylalkyl; 6-10-membered aryl; 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur. In some embodiments, $R^6$ is hydrogen. In some embodiments, $R^6$ is 4-chlorophenyl.

In some embodiments, R is hydrogen. In some embodiments, R is $C_{1-6}$ alkyl. In some embodiments, R is methyl. In some embodiments R is ethyl. In some embodiments R is propyl. In some embodiments R is butyl.

In certain embodiments of compounds of formulae III-a and III-b, T is —$CH_2$—. In some embodiments, such compounds are of formula IV-i or IV-ii:

IV-i

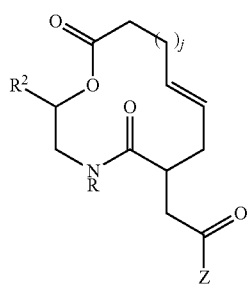

IV-ii

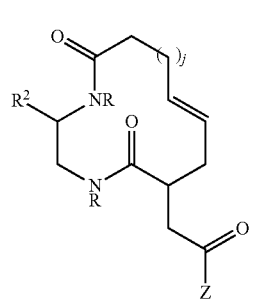

wherein j is an integer from 1 to 3, inclusive; and each of Z, R, and $R^2$ is as defined above and described in classes and subclasses herein.

In certain embodiments of compounds of formulae III-a and III-b, T is —$CH_2$—. In some embodiments, such compounds are of formula IV-iii or IV-iv:

IV-iii

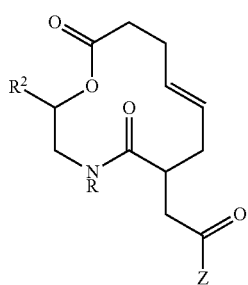

IV-iv

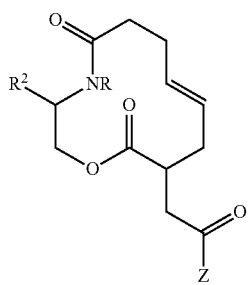

wherein each of Z, R, and $R^2$ is as defined above and described in classes and subclasses herein.

In certain embodiments, the Z group of formulae IV-i and IV-ii is $NR^4R^5$, providing compounds of formula IV-a, IV-b, IV-c, IV-d, IV-e, or IV-f:

IV-a

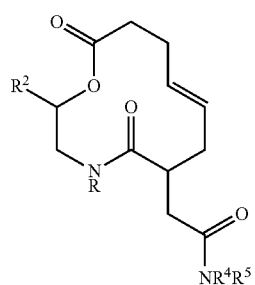

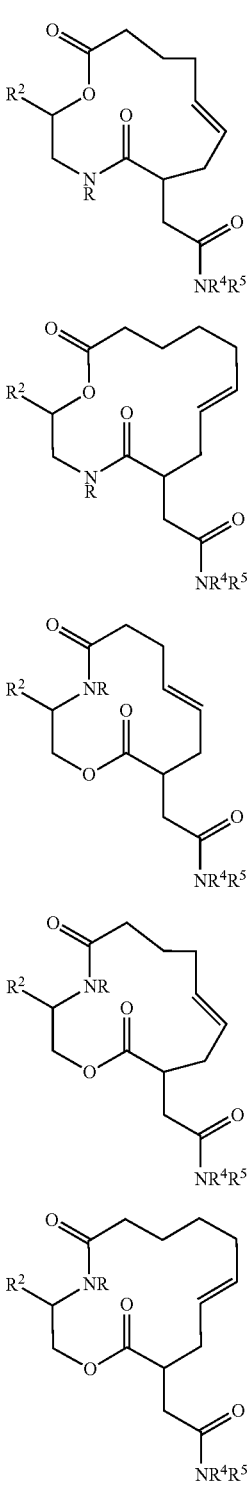

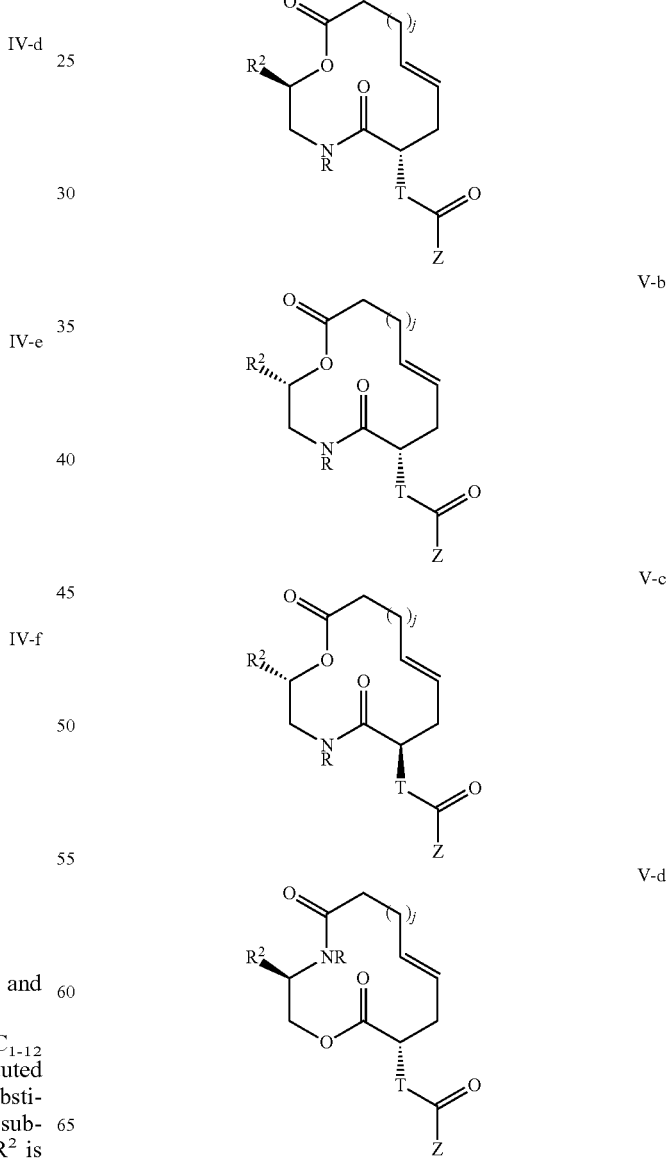

wherein each of R, $R^2$, $R^4$, and $R^5$ is as defined above and described in classes and subclasses herein.

In some embodiments, $R^2$ is optionally substituted $C_{1-12}$ aliphatic. In some embodiments, $R^2$ is optionally substituted $C_{1-6}$ aliphatic. In some embodiments, $R^2$ is optionally substituted $C_{1-6}$ alkyl. In some embodiments, $R^2$ is optionally substituted 6-10-membered aryl. In some embodiments, $R^2$ is methyl. In some embodiments, $R^2$ is substituted or unsubstituted phenyl. In some embodiments, $R^2$ is substituted phenyl. In some embodiments, $R^2$ is unsubstituted phenyl.

In certain embodiments, $R^4$ is hydrogen.

In some embodiments, $R^5$ is —$C(R^6)_3$ and each occurrence of $R^6$ is independently hydrogen or an optionally substituted moiety selected from the group consisting of $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur. In some embodiments, $R^6$ is hydrogen. In some embodiments, $R^6$ is 4-chlorophenyl.

In some embodiments, R is hydrogen. In some embodiments, R is $C_{1-6}$ alkyl. In some embodiments, R is methyl. In some embodiments R is ethyl. In some embodiments R is propyl. In some embodiments R is butyl.

The invention further provides compounds of formulae V-a, V-b, V-c, V-d, V-e, and V-f:

-continued

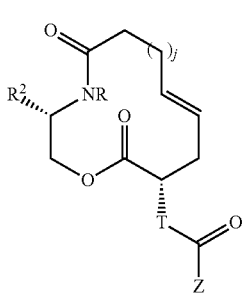
V-e

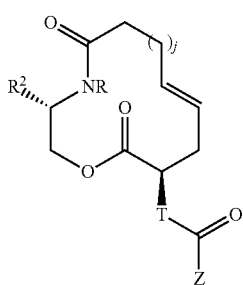
V-f wherein j is an integer from 1 to 3, inclusive; and each of T, Z, R, and $R^2$ is as defined above and described in classes and subclasses herein.

In some embodiments, the invention provides compounds of formula V-g or V-h:

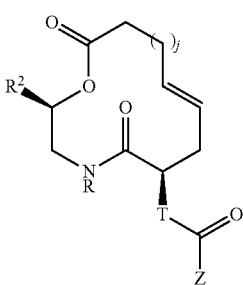
V-g

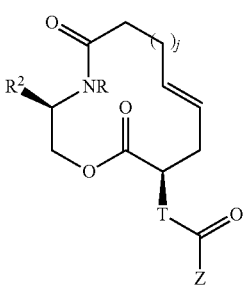
V-h wherein j is an integer from 1 to 3, inclusive; and each of T, Z, R, and $R^2$ is as defined above and described in classes and subclasses herein.

In some embodiments, $R^2$ is substituted phenyl, providing a compound of formula VI-a or VI-b:

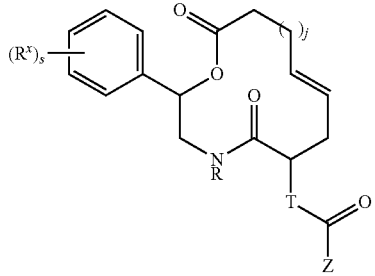
VI-a

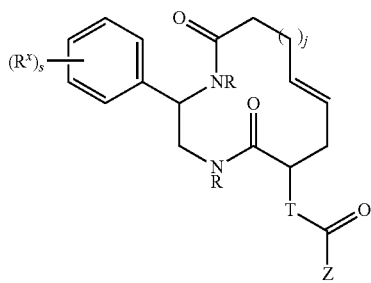
VI-b wherein, s is an integer from 1 to 5, inclusive;

each $R^x$ is independently selected from hydrogen, halogen, —CN, —SCN, —$NO_2$, —$CO_2R$, —SOR, —$SO_2R$, —$NR_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;

j is an integer from 1 to 3, inclusive;

each R is independently hydrogen, a protecting group, an acyl moiety, arylalkyl moiety, aliphatic moiety, aryl moiety, heteroaryl moiety, or heteroaliphatic moiety; or:

two R on the same nitrogen atom may be taken with the nitrogen to form a 4-7-membered heterocyclic ring having 1-2 heteroatoms independently selected from nitrogen, oxygen, or sulfur; and each of T and Z is as defined above and described in classes and subclasses herein.

In certain embodiments, s is 1. In certain embodiments, s is 2. In certain embodiments, s is 3.

In some embodiments, R is hydrogen. In some embodiments, R is $C_{1-6}$ alkyl. In some embodiments, R is methyl. In some embodiments, R is ethyl. In some embodiments, R is propyl. In some embodiments, R is butyl.

In certain embodiments, Z is —$NR^4R^5$, $R^5$ is —$C(R^6)_3$, and each occurrence of $R^6$ is independently hydrogen or an optionally substituted moiety selected from the group consisting of $C_{7-15}$ arylalkyl and 6-10-membered aryl. In some embodiments, such compounds are of formula VII-a or VII-b:

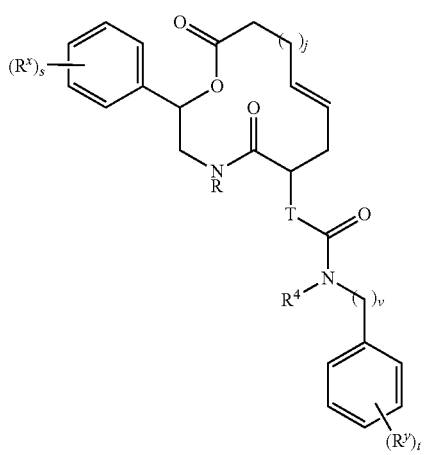

VII-a

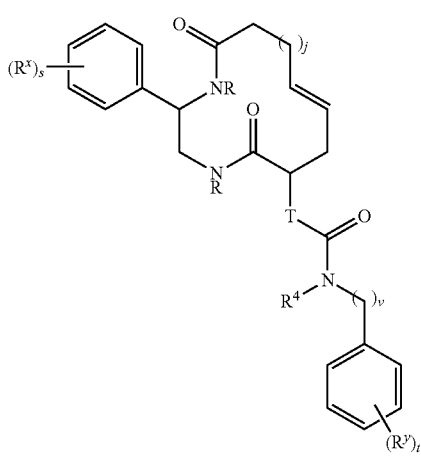

VII-b v is an integer from 1 to 10, inclusive;
t is an integer from 1 to 5, inclusive;
each $R^y$ is independently selected from hydrogen, halogen, —CN, —SCN, —NO$_2$, —CO$_2$R, —SOR, —SO$_2$R, —NR$_2$, —OR, —SR, or an optionally substituted group selected from the group consisting of acyl, C$_{1-12}$ aliphatic, C$_{1-12}$ heteroaliphatic, C$_{7-15}$ arylalkyl, C$_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;
j is an integer from 1 to 3, inclusive;
  each R is independently hydrogen, a protecting group, an acyl moiety, arylalkyl moiety, aliphatic moiety, aryl moiety, heteroaryl moiety, or heteroaliphatic moiety; or:
    two R on the same nitrogen atom may be taken with the nitrogen to form a 4-7-membered heterocyclic ring having 1-2 heteroatoms independently selected from nitrogen, oxygen, or sulfur; and
each of T, Z, $R^x$, $R^4$, and s is as defined above and described in classes and subclasses herein.
In some embodiments, t is 1. In some embodiments, t is 2. In some embodiments, t is 3.

In some embodiments, v is an integer from 1 to 8, inclusive. In some embodiments, v is an integer from 2 to 10, inclusive. In some embodiments, v is an integer from 1 to 6, inclusive. In some embodiments, v is an integer from 1 to 4, inclusive. In some embodiments, a hydrocarbon chain formed by methylene moieties is optionally substituted.

In some embodiments, R is hydrogen. In some embodiments, R is C$_{1-6}$ alkyl. In some embodiments, R is methyl. In some embodiments, R is ethyl. In some embodiments, R is propyl. In some embodiments, R is butyl.

Exemplary compounds of formula I are set forth in Table 2, below.

TABLE 2

Exemplary compounds of formula I

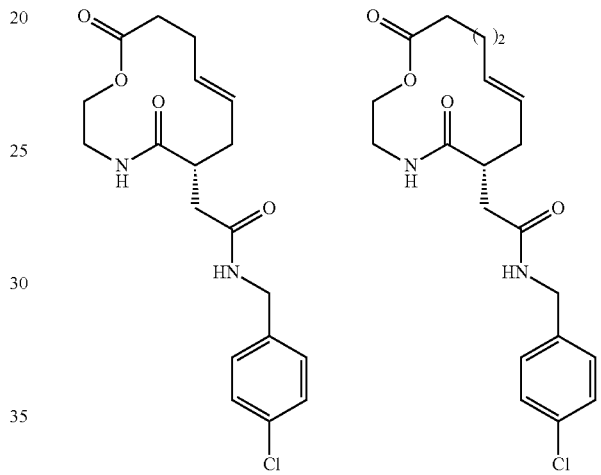

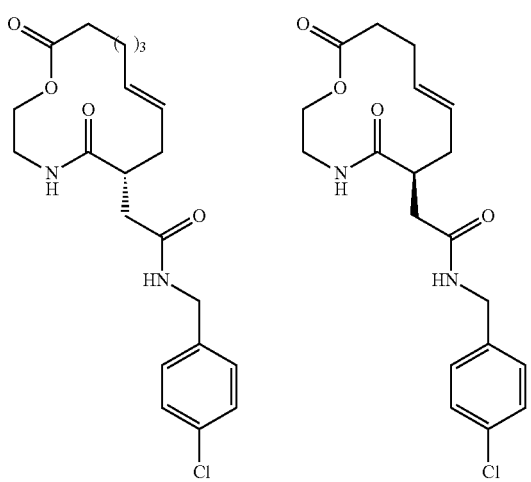

TABLE 2-continued
Exemplary compounds of formula I
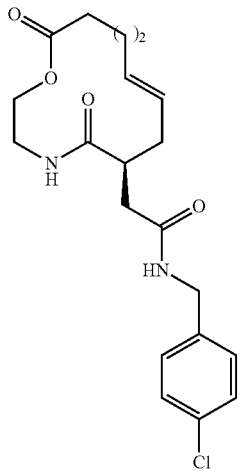 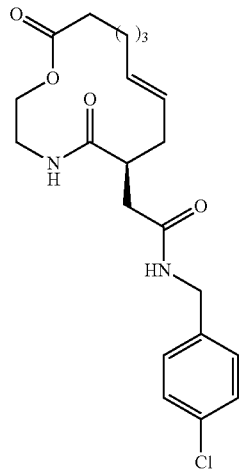 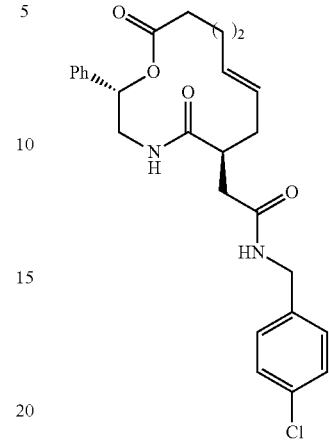 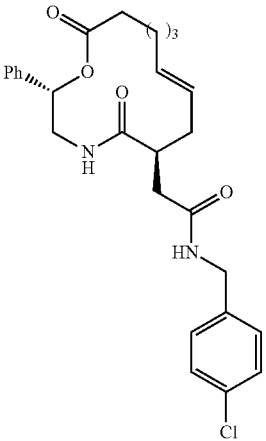
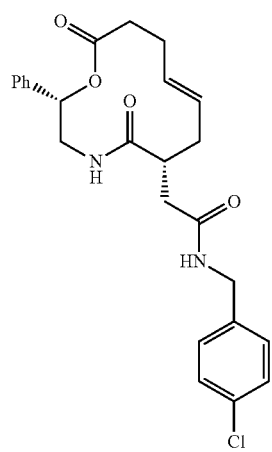 [SMILES: O=C(C[C@H]1C/C=C/CCC(=O)O[C@@H](c2ccccc2)CNC1=O)NCc1ccc(Cl)cc1] 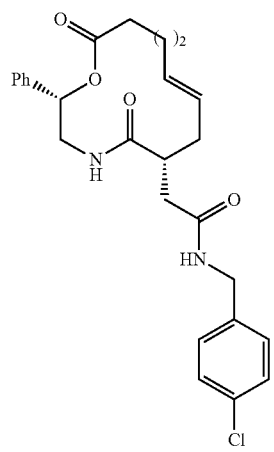 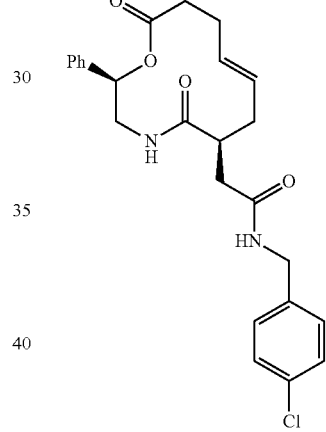 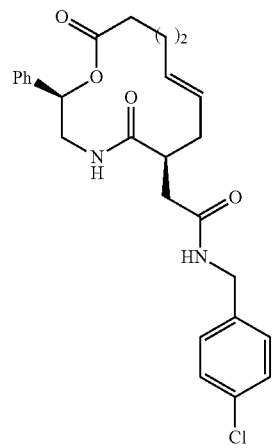
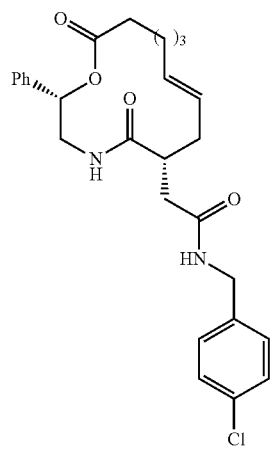 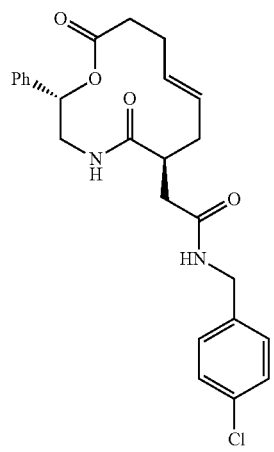 [SMILES: O=C(C[C@@H]1C/C=C/CCC(=O)O[C@@H](c2ccccc2)CNC1=O)NCc1ccc(Cl)cc1] 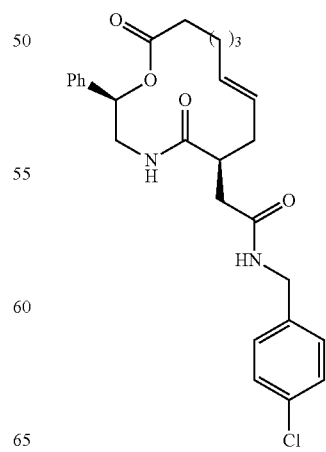 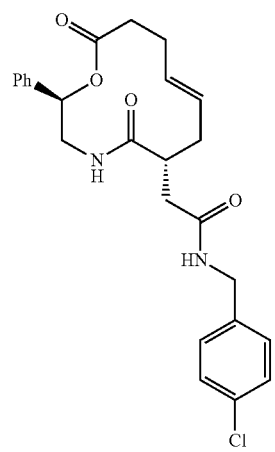 [SMILES: O=C(C[C@H]1C/C=C/CCC(=O)O[C@H](c2ccccc2)CNC1=O)NCc1ccc(Cl)cc1]

TABLE 2-continued
Exemplary compounds of formula I
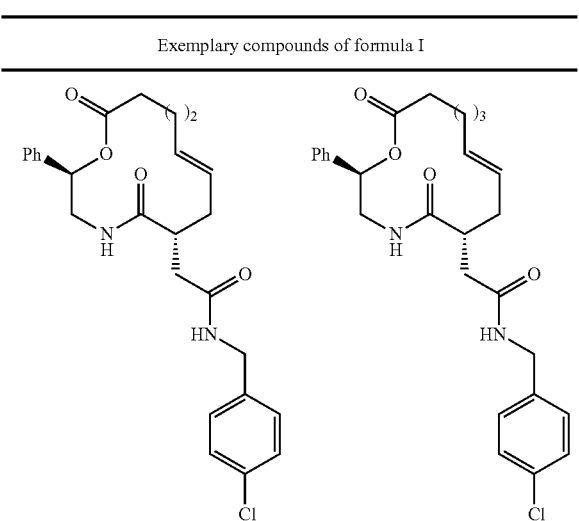
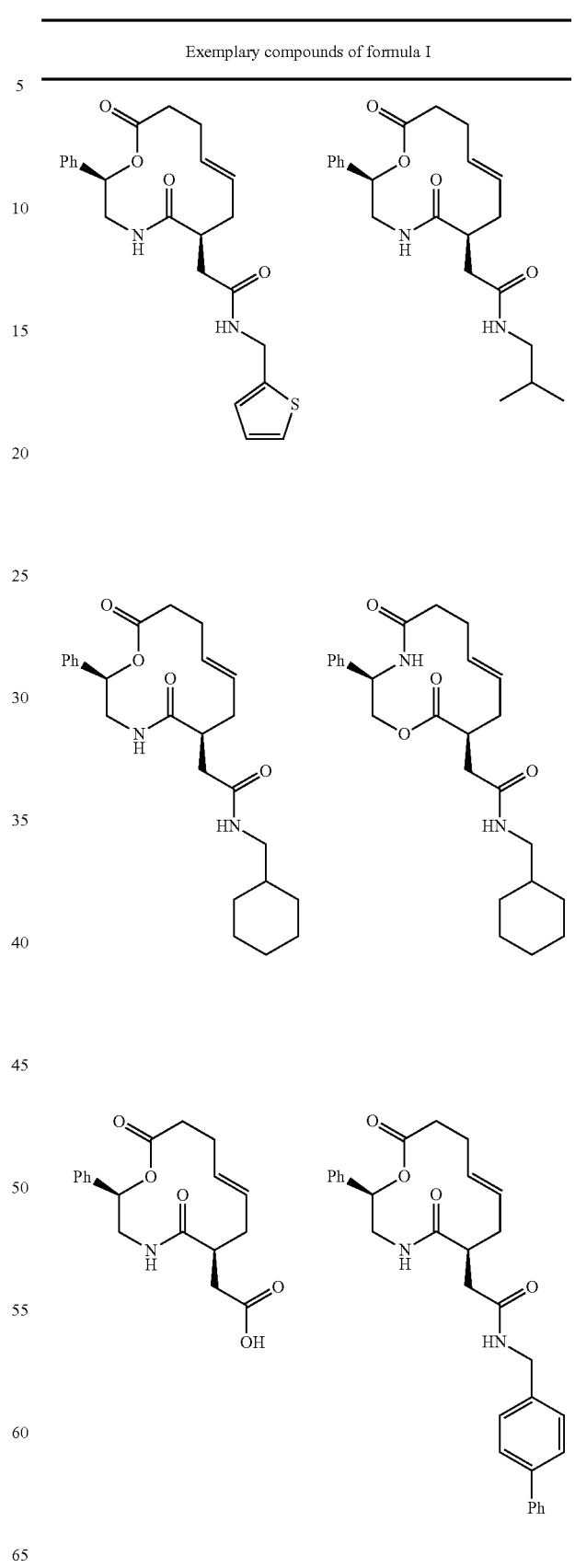

TABLE 2-continued
Exemplary compounds of formula I
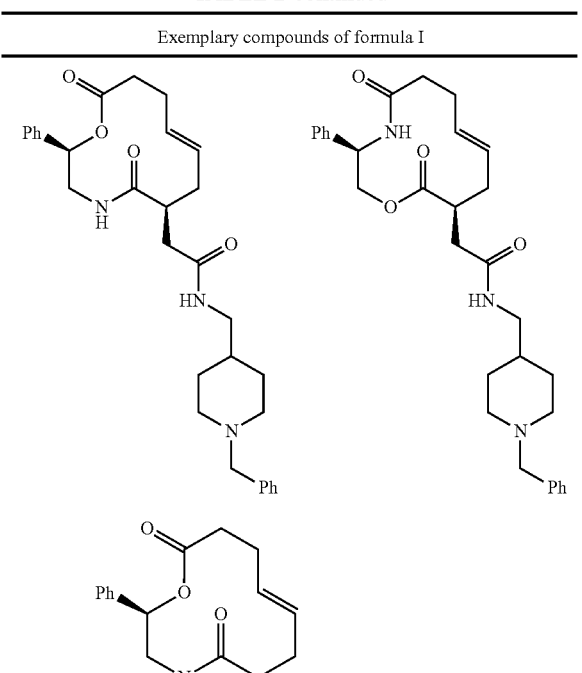
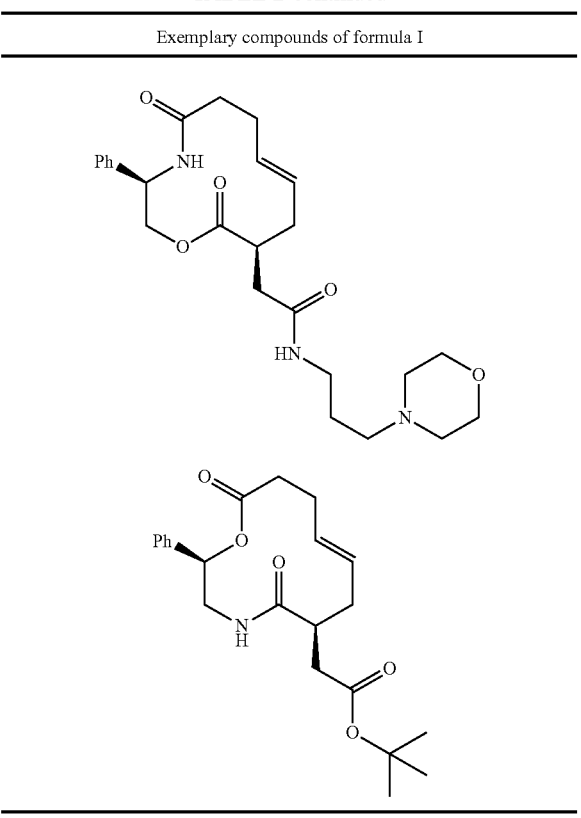
Additional exemplary compounds of formula I are set forth in Table 2a, below.
TABLE 2a
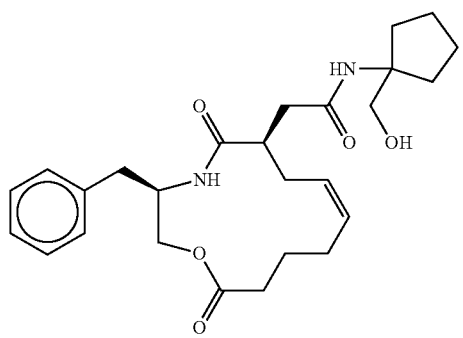
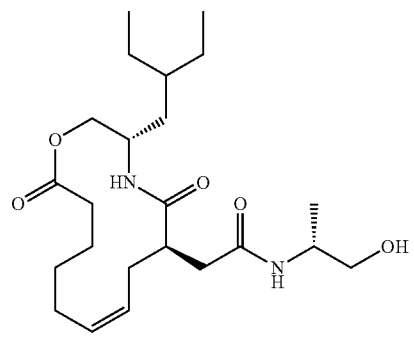 [SMILES: CCC(CC)C[C@H]1COC(=O)CCCC/C=C\C[C@H](CC(=O)N[C@H](C)CO)C(=O)N1]

TABLE 2a-continued
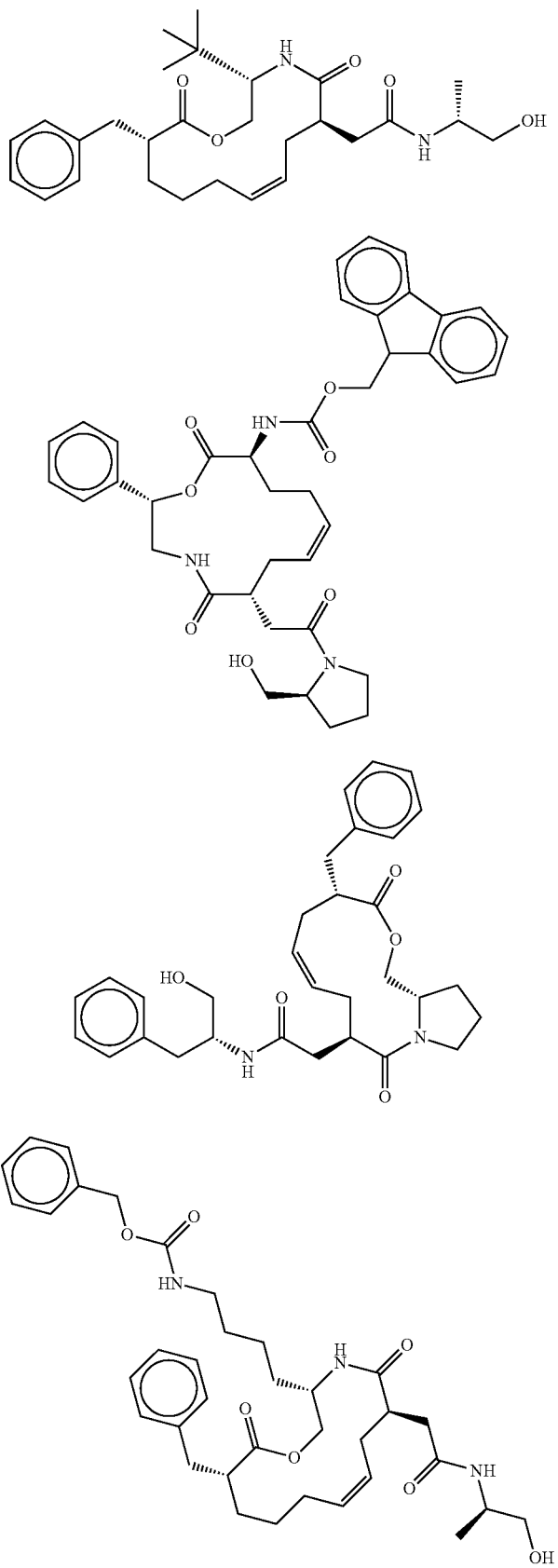

TABLE 2a-continued
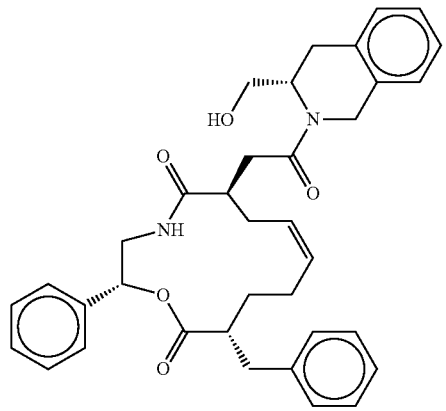
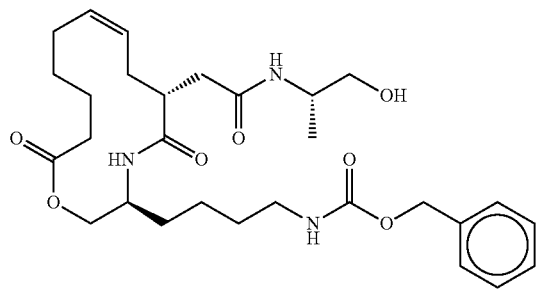
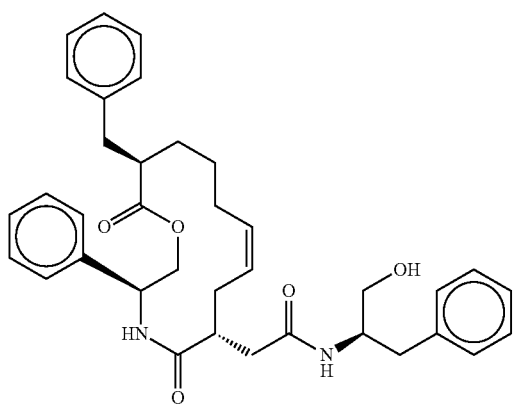
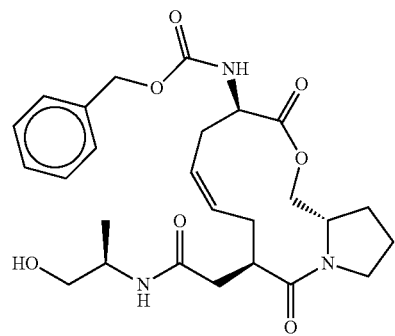

TABLE 2a-continued
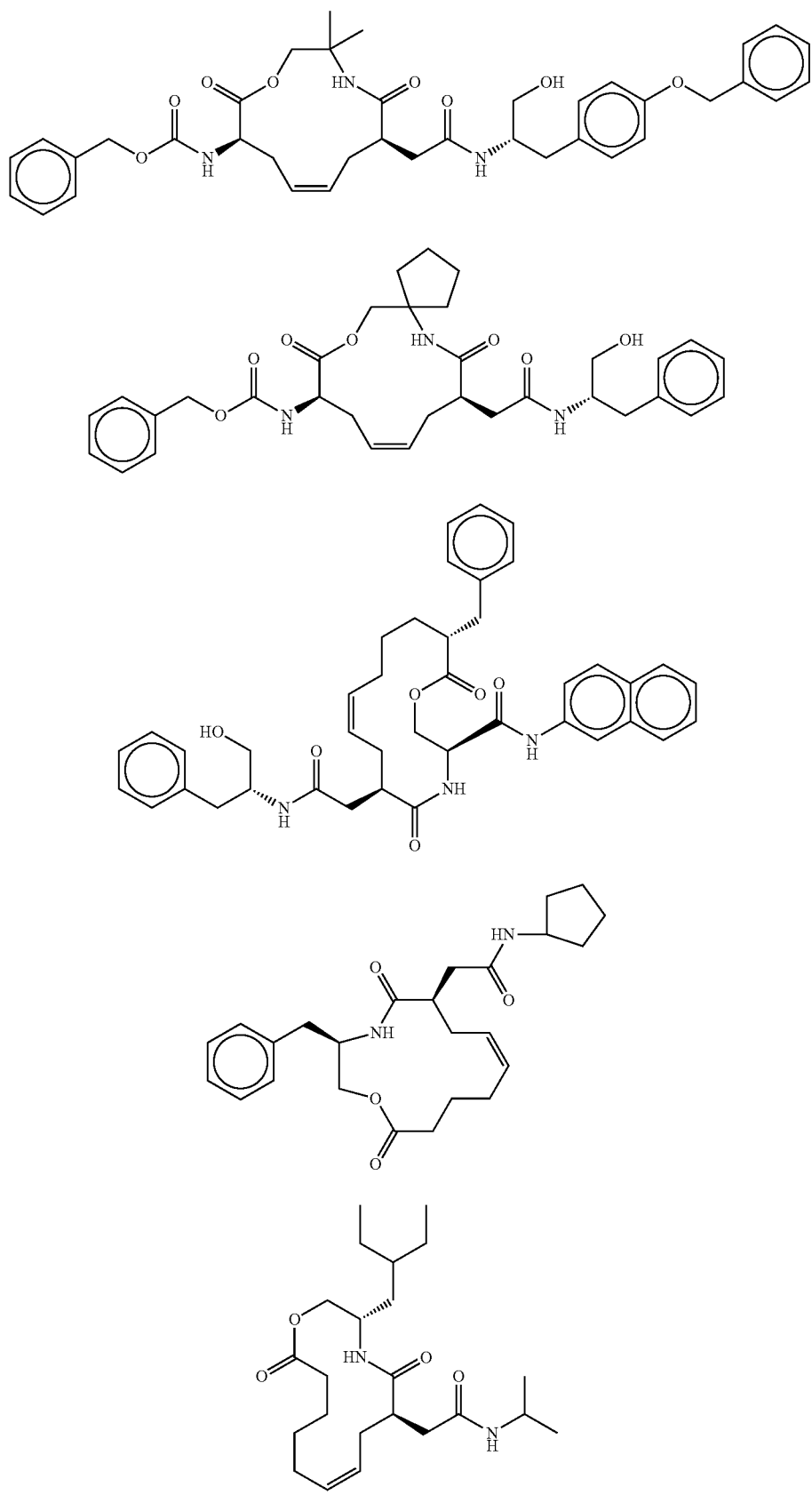

TABLE 2a-continued
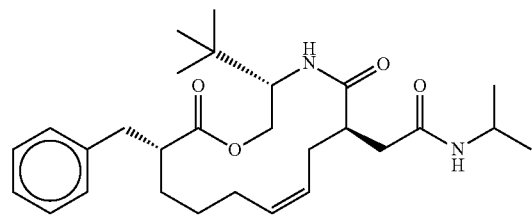
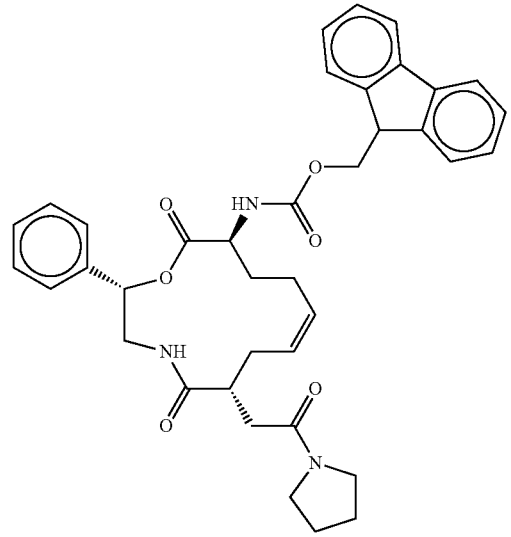
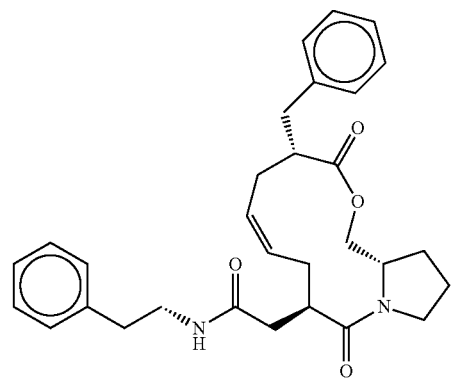
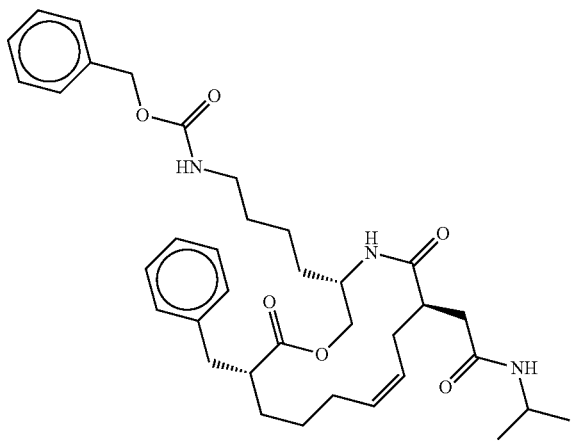

TABLE 2a-continued
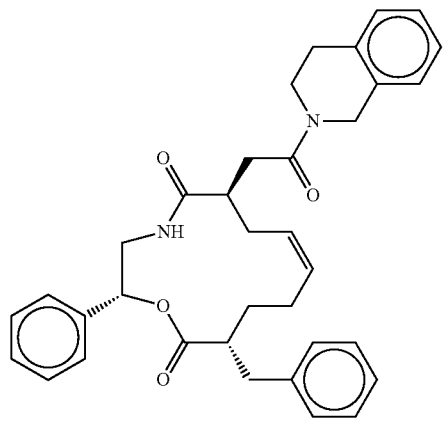
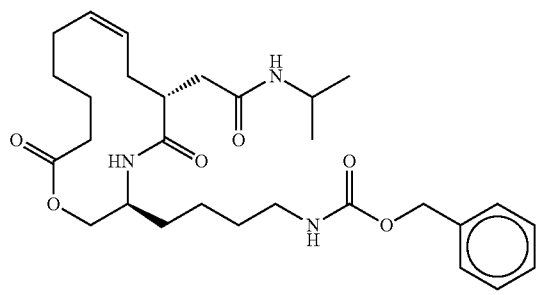
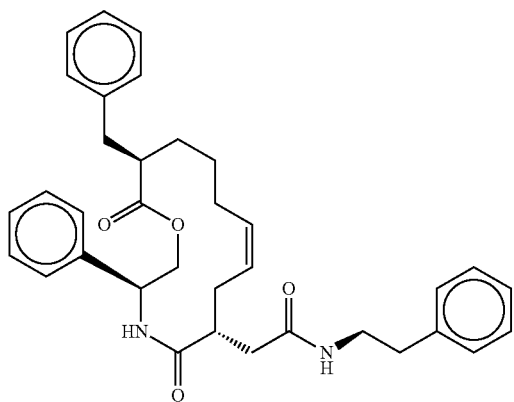
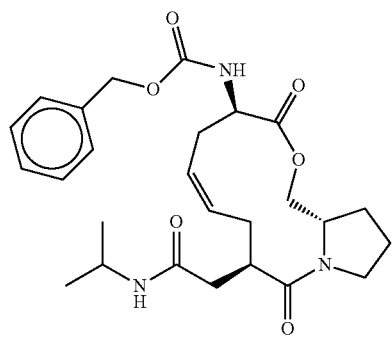

TABLE 2a-continued

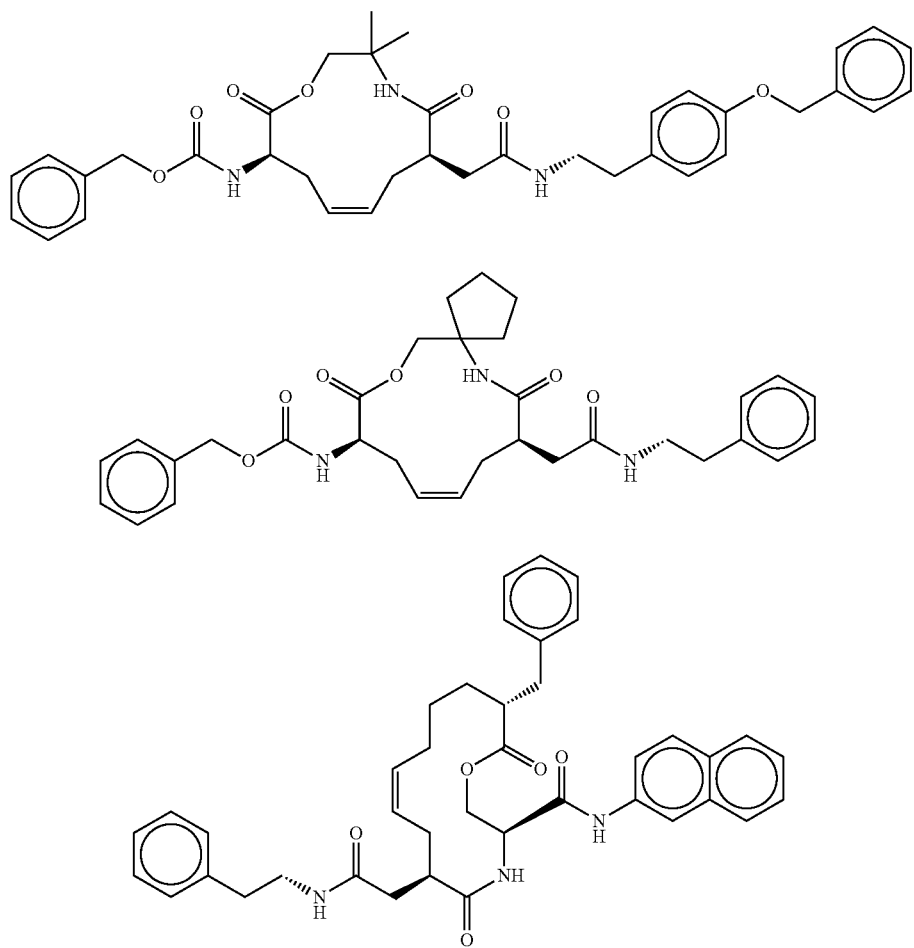

Synthesis of Compounds

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.)

In one aspect, the present invention provides methods for the synthesis of compounds of formula I and intermediates thereto. In some embodiments, such methods are as shown in Scheme 1, below, wherein LG and $LG^1$ are suitable leaving groups, PG and $PG^1$ are suitable protecting groups, and Z, $R^1$, $R^2$, $R^3$, n, m, j, and k are as defined above and described in classes and subclasses herein.

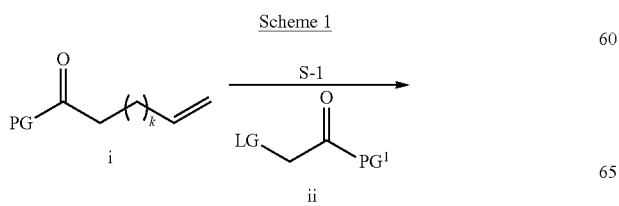

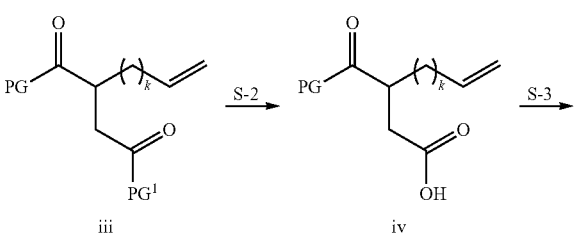

-continued

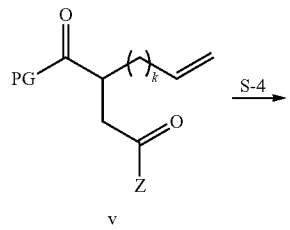

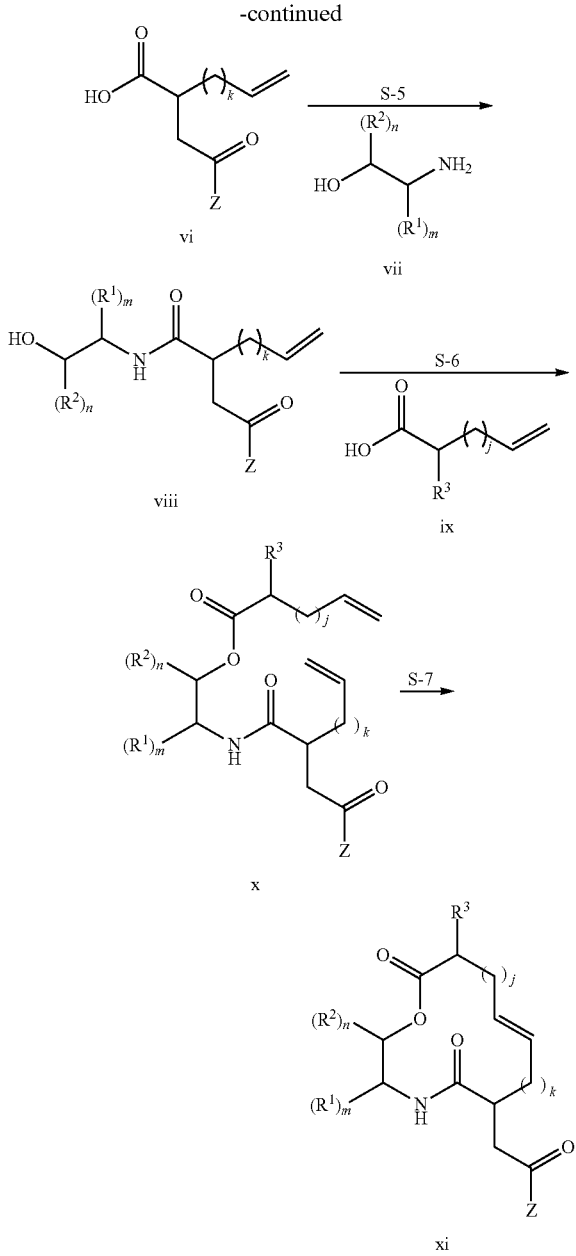

As depicted in Scheme 1, a compound of formula i is reacted with ester ii to form a compound of formula iii. A compound of formula iii is treated under suitable conditions to remove a protecting group, thereby forming a carboxylic acid of formula iv. Carboxylic acid of formula iv is then coupled with a nucleophile to form a compound of formula v, which is then deprotected under suitable conditions to form a carboxylic acid of formula vi. Carboxylic acid of formula vi is treated with an amino alcohol of formula vii to form an alcohol of formula viii, which is then coupled to a carboxylic acid of formula ix. The resulting ester of formula x is then treated under suitable conditions to form a macrocycle of formula xi.

The PG and PG$^1$ groups of formulae i, ii, iii, iv and v are suitable protecting groups. Suitable protecting groups are well known in the art and include those described by Greene (infra). Additional suitable protecting groups are described above and herein. In certain embodiments, the PG group is a carboxylate protecting group. In some embodiments, the PG group also serves as a chiral auxiliary to afford a stereoselective carbon-carbon bond formation at step S-1. The use of chiral auxiliaries is well-known in the art (see, for example, Evans et al., infra). In certain embodiments, the PG group is an oxazolidinone.

The LG group of formula II is a suitable leaving group. One of ordinary skill in the art will appreciate that a variety of suitable leaving groups LG can be used to facilitate the reaction described in step S-1, and all such suitable leaving groups are contemplated by the present invention. A suitable leaving group is a chemical group that is readily displaced by a desired incoming chemical moiety. Suitable leaving groups are well known in the art, e.g., see, March, supra. Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of some suitable leaving groups include chloro, iodo, bromo, fluoro, methanesulfonyl (mesyl), tosyl, triflate, nitro-phenylsulfonyl (nosyl), and bromo-phenylsulfonyl (brosyl).

Step S-1

At step S-1, a compound of formula i is reacted with an ester of formula II to form a compound of formula iii. Step S-1 may optionally employ a suitable base. Such suitable bases include strong inorganic bases, i.e., those that completely dissociate in water with formation of hydroxide anion. In some embodiments, the base is a strong organic base. In certain embodiments, the base is added in an amount of at least about 1 mol. eq. and, in other embodiments, in an amount of at least about 1 mol. eq. to about 10 mol. eq. relative to an ester of formula II. Examples of such bases include alkaline metals, alkaline earth metal hydroxides, bis (silyl) amides, and combinations thereof. In some embodiments, the suitable base is NaHMDS. In other embodiments, the base is sodium hydride. In yet other embodiments, the base is an amine base.

Step S-1 typically employs a suitable solvent. Examples of solvents suitable for use at step S-1 include polar solvents such as alkyl alcohols, for example $C_1$ to $C_4$ alcohols (e.g., ethanol, methanol, 2-propanol), water, dioxane, ethyl acetate, acetonitrile, THF (tetrahydrofuran), or combinations thereof. In certain embodiments, the solvent is THF.

In some embodiments, step S-1 is carried out at temperatures of about −78° C. In some embodiments, step S-1 is carried out at temperatures of about −78 to −48° C. In some embodiments, step S-1 is carried out at temperatures of about 0° C.

In certain embodiments, the present invention provides a compound of formula iii:

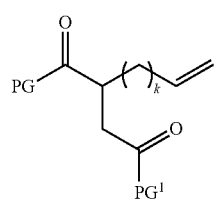

iii wherein k is an integer from 0 to 4, inclusive; and PG and PG$^1$ are suitable protecting groups;

comprising the steps of:
(a) providing a compound of formula i:

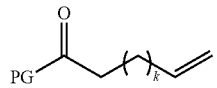

and (b) reacting compound of formula i with an ester of formula ii:

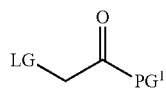

wherein PG$^1$ is a suitable protecting group and LG is a suitable leaving group;
under suitable conditions to yield a compound of formula iii.

Step S-2

At step S-2, compound of formula iii is treated under suitable conditions to remove a protecting group PG$^1$, thereby forming a carboxylic acid of formula iv. It will be appreciated that, depending upon the particular protecting group used, a variety of conditions may be used to remove the PG$^1$ group. Such strategies will be known to one of ordinary skill in the art, and are described by Greene (infra). In some embodiments, the protecting group is removed using an acid. In certain embodiments, the acid is trifluoroacetic acid.

Solvents suitable for use in step S-2 include polar aprotic solvents (i.e., THF, dioxane, acetonitrile, and combinations thereof), halogenated hydrocarbons (e.g., dichloromethane, chloroform, carbon tetrachloride, methyl chloroform, 1,2-dichloroethane, 1,1-dichloroethane), aromatic hydrocarbons (e.g., benzene, toluene, xylenes, ethylbenzene), or halogenated aromatic hydrocarbons (e.g., chlorobenzene, dichlorobenzenes). In certain embodiments, the solvent is THF or a halogenated hydrocarbon. In some embodiments, the solvent is dichloromethane.

In some embodiments, step S-2 is carried out at temperatures of about 20-60° C.

In some embodiments, the present invention provides a method comprising the steps of:
(a) providing a compound of formula iii:

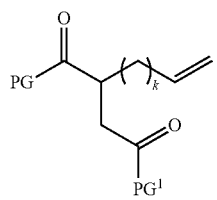

wherein k is an integer from 0 to 4, inclusive; and PG and PG$^1$ are suitable protecting groups;

(b) deprotecting said compound of formula iii under suitable conditions to remove PG$^1$ to form a carboxylic acid of formula iv:

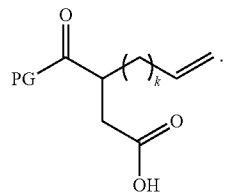

Step S-3

At step S-3, a carboxylic acid of formula iv is then coupled with a nucleophile to form a compound of formula v. As described above for compounds of formula I, Z is —NR$^4$R$^5$, —OR$^5$, or —SR$^5$, and any such —NR$^4$R$^5$, —OR$^5$, or —SR$^5$ group may be coupled with a carboxylic acid of formula iv to form compounds of formula v. Suitable conditions for coupling —NR$^4$R$^5$, —OR$^5$, or —SR$^5$ groups with a carboxylic acid of formula iv are known in the art and include those described in March (supra) and Han, S. Y.; Kim, Y. A. *Tetrahedron*, 60: 2447-2467, 2004. Examples of coupling reagents useful in forming a compound of formula v from the corresponding carboxylic acid include HOBt, HAMDU, HOTT, HODT, TOTT, TODT, DMAP, BOP, NOP, PyAOP, AOP, PyBOP, PyNOP, PyBroP, PyCloP, PyFOP, PyTOP, PyPOP, PyDOP, BOP-Cl, ENDPP, HBTU, TBTU, TSTU, TDBTU, HDTU, TPTU, DEPBT, TOTU, PyClU, TPyClU, HAPyU, HBPyU, HPyOPfp, HPySPfp, HAPipU, TAPipU, HOAt, HATU, HDTU, BMC, BEC, BDDC, N,N-dicyclopentylcarbodiimide, HOSu, PfpOH, BOMI, DCC, EDC, IBCF, DIC, CIC, CDI, CBMIT, BOI, CIP, CIB, CMBI, BEMT, BEP, BEMT, BMTB, DPPA, DECP, DEPB, DEPC, MPTA, MPTO, DPP-Cl, FDPP, ENDPP, BMP-Cl, NDPP, Cpt-Cl, DEBP, BDP, DEPBO, DOPBO, DOPBT, DEPBT, CDMT, BTC, TFFH, BTFFH, DFIH, BMPI, CMPI, BEP, FEP, BEPH, FEPH, DMTMM, HODhbt, HOCt, PTF, or a combination thereof.

In certain embodiments, EDC is used in step S-3, optionally in the presence of one or more other promoters such as those described above. In certain embodiments, step S-3 is carried out using EDC and HOBt.

Step S-3 may optionally employ a suitable base. Suitable bases include amine bases, such as trialkylamines (e.g. triethylamine, DIPEA, N-methyl morpholine, DABCO), dialkylamines (e.g., diisopropylamine) partially unsaturated or aromatic heterocyclic amines (e.g. DBU, DMAP, PPTS, imidazole), to name but a few. In certain embodiments, the base is diisopropylethylamine (DIPEA or DIEA). In certain embodiments, the base is a combination of DIEA and DMAP.

Solvents suitable for use in step S-3 include polar aprotic solvents (e.g., THF, DMF, dioxane, acetonitrile, and combinations thereof), halogenated hydrocarbons (e.g., dichloromethane, chloroform, carbon tetrachloride, methyl chloroform, 1,2-dichloroethane, 1,1-dichloroethane), aromatic hydrocarbons (e.g., benzene, toluene, xylenes, ethylbenzene), or halogenated aromatic hydrocarbons (e.g., chlorobenzene, dichlorobenzenes). In certain embodiments, the solvent is THF or a halogenated hydrocarbon. In some embodiments, the solvent is dichloromethane.

In some embodiments, step S-3 is carried out at temperatures of about 20-60° C. In some embodiments, step S-3 is carried out at temperatures of about 0-25° C.

In some embodiments, the present invention provides a method comprising the steps of:
(a) providing a compound of formula iv:

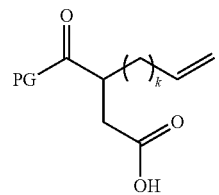

(b) coupling said compound of formula iv under suitable coupling conditions with a nucleophile to form a compound of formula v:

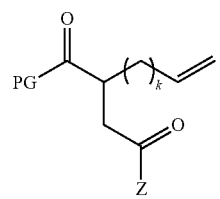

wherein
Z is —NR$^4$R$^5$, —OR$^5$, or —SR$^5$;
R$^4$ is hydrogen, —OR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur;
R$^5$ is hydrogen or —C(R$^6$)$_3$; or, when R$^5$ is —C(R$^6$)$_3$, R$^4$ and R$^5$ may be taken together with their intervening atoms to form a 3-8-membered ring;
each occurrence of R$^6$ is independently hydrogen, halogen, —CN, —SCN, —NO$_2$, —CO$_2$R, —SOR, —SO$_2$R, —NR$_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or
two occurrences of R$^6$ may be taken together with their intervening atoms to form a 3-8-membered ring; and
each R is independently hydrogen, a protecting group, an acyl moiety, arylalkyl moiety, aliphatic moiety, aryl moiety, heteroaryl moiety, or heteroaliphatic moiety; or:
two R on the same nitrogen atom may be taken with the nitrogen to form a 4-7-membered heterocyclic ring having 1-2 heteroatoms independently selected from nitrogen, oxygen, or sulfur.

Step S-4

At step S-4, a compound of formula v is treated under suitable conditions to remove the PG group and form a carboxylic acid of formula vi. It will be appreciated that, depending upon the particular protecting group used, a variety of conditions may be used to remove the PG group. Such strategies will be known to one of ordinary skill in the art, and are described by Greene (infra). In some embodiments, the protecting group is removed using a base. In certain embodiments, the base is lithium hydroxide. In some embodiments, the conditions comprise lithium hydroxide and hydrogen peroxide.

Step S-4 may optionally employ a suitable solvent. Suitable solvents include protic solvents such as $C_1$-$C_4$ alcohols including ethanol, methanol, isopropanol, n-propanol, and n-butanol; water miscible polar aprotic solvents such as tetrahydrofuran, dioxane, acetone, and acetonitrile; water; and combinations thereof. In certain embodiments, the solvent is water and THF.

In some embodiments, step S-4 is carried out at temperatures of about 20-60° C. In some embodiments, step S-4 is carried out at temperatures of about 0-25° C.

In certain embodiments, the present invention provides a method comprising the steps of:
(a) providing a compound of formula v:

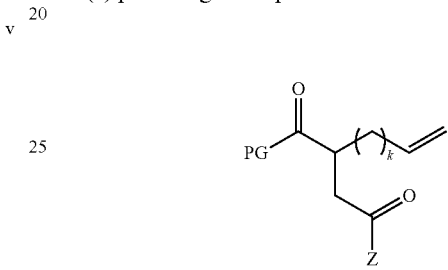

(b) deprotecting said compound of formula v under suitable conditions to remove PG to form a carboxylic acid of formula vi:

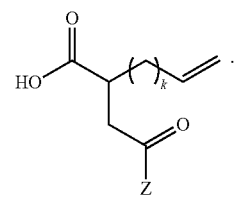

Step S-5

At step S-5, a carboxylic acid of formula vi is treated under suitable conditions with an amino alcohol of formula vii to form an alcohol of formula viii. One of ordinary skill in the art will recognize that the reaction of a carboxylic acid of formula vi with an amine group of formula vii to form an alcohol of formula viii may be carried out using suitable coupling conditions useful in peptide synthesis. Such methods are known in the art and include those described in March (supra) and Han (supra), as well as those described for step S-3. In certain embodiments, EDC is used in step S-5, optionally in the presence of one or more other promoters such as those described above. In certain embodiments, step S-5 is carried out using EDC and HOBt. In certain embodiments, step S-5 is carried out using PyBOP.

Step S-5 may optionally employ a suitable base. Suitable bases include amine bases, such as trialkylamines (e.g. triethylamine, DIPEA, N-methyl morpholine, DABCO), dialkylamines (e.g., diisopropylamine), partially unsaturated or aromatic heterocyclic amines (e.g. DBU, DMAP, PPTS, imidazole), to name but a few. In certain embodiments, the base is diisopropylethylamine (DIPEA or DIEA). In certain embodiments, the base is DIEA. In certain embodiments, the base is a combination of DIEA and DMAP.

Solvents suitable for use in step S-5 include polar aprotic solvents (i.e., THF, DMF, dioxane, acetonitrile, and combinations thereof), halogenated hydrocarbons (e.g., dichloromethane, chloroform, carbon tetrachloride, methyl chloroform, 1,2-dichloroethane, 1,1-dichloroethane), aromatic hydrocarbons (e.g., benzene, toluene, xylenes, ethylbenzene) or halogenated aromatic hydrocarbons (e.g., chlorobenzene, dichlorobenzenes). In certain embodiments, the solvent is THF or a halogenated hydrocarbon. In some embodiments, the solvent is dichloromethane. In some embodiments, the solvent is a mixture of dichloromethane and DMF.

In some embodiments, step S-5 is carried out at temperatures of about 20-60° C. In some embodiments, step S-5 is carried out at temperatures of about 0-25° C.

In certain embodiments the present invention provides a method comprising the steps of:

(a) providing a carboxylic acid of formula vi:

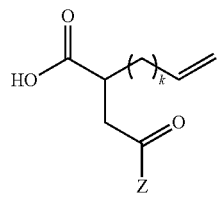

vi (b) reacting carboxylic acid of formula vi under suitable conditions with an amino alcohol of formula vii:

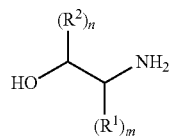

vii wherein
m is an integer from 0 to 2, inclusive;
n is an integer from 0 to 2, inclusive;
each occurrence of $R^1$ is independently hydrogen, halogen, —CN, —SCN, —NO$_2$, —CO$_2$R, —SOR, —SO$_2$R, —NR$_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or
two $R^1$ groups may be taken together with their intervening atoms to form a 3-8-membered ring; or
when $X^2$ is —NR—, $R^1$ and the R of —NR— may be taken together with their intervening atoms to form a 3-8-membered ring;
each occurrence of $R^2$ is independently hydrogen, halogen, —CN, —SCN, —NO$_2$, —CO$_2$R, —SOR, —SO$_2$R, —NR$_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; or two $R^2$ groups may be taken together with their intervening atoms to form a 3-8-membered ring; and each R is independently hydrogen, a protecting group, an acyl moiety, arylalkyl moiety, aliphatic moiety, aryl moiety, heteroaryl moiety, or heteroaliphatic moiety; or:

two R on the same nitrogen atom may be taken with the nitrogen to form a 4-7-membered heterocyclic ring having 1-2 heteroatoms independently selected from nitrogen, oxygen, or sulfur;

to form an alcohol of formula viii:

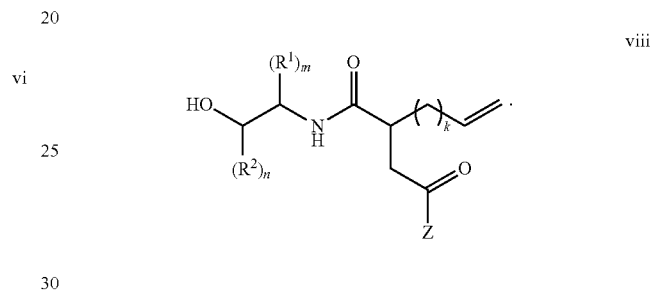

viii

Step S-6

At step S-6, an alcohol of formula viii is coupled to a carboxylic acid of formula ix to form an ester of formula x. Suitable conditions for coupling alcohols with a carboxylic acid of formula ix are known in the art and include those described in March (supra) and Han (supra) as well as those described for step S-3. In certain embodiments, EDC is used in step S-6, optionally in the presence of one or more other promoters such as those described above. In certain embodiments, DIC is used in step S-6, optionally in the presence of one or more other promoters such as those described above.

Step S-6 may optionally employ a suitable base. Suitable bases include amine bases, such as trialkylamines (e.g. triethylamine, DIPEA, N-methyl morpholine, DABCO), dialkylamines (e.g., diisopropylamine), partially unsaturated or aromatic heterocyclic amines (e.g. DBU, DMAP, PPTS, imidazole), to name but a few. In certain embodiments, the base is diisopropylethylamine (DIPEA or DIEA). In certain embodiments, the base is DMAP. In certain embodiments, the base is a combination of DIEA and DMAP.

Solvents suitable for use in step S-6 include polar aprotic solvents (i.e., THF, DMF, dioxane, acetonitrile, and combinations thereof), halogenated hydrocarbons (e.g., dichloromethane, chloroform, carbon tetrachloride, methyl chloroform, 1,2-dichloroethane, 1,1-dichloroethane), aromatic hydrocarbons (e.g., benzene, toluene, xylenes, ethylbenzene) or halogenated aromatic hydrocarbons (e.g., chlorobenzene, dichlorobenzenes). In certain embodiments, the solvent is THF or a halogenated hydrocarbon. In some embodiments, the solvent is DMF. In some embodiments, the solvent is dichloromethane.

In some embodiments, step S-6 is carried out at temperatures of about 20-60° C.

In some embodiments, the present invention provides a method comprising the steps of:
(a) providing an alcohol of formula viii:

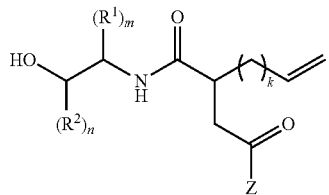

viii and
(b) reacting alcohol of formula viii under suitable conditions with a carboxylic acid of formula ix:

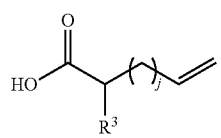

ix wherein,
j is an integer from 0 to 4, inclusive;
$R^3$ is hydrogen, halogen, —CN, —SCN, —NO$_2$, —CO$_2$R, —SOR, —SO$_2$R, —NR$_2$, —OR, —SR, or an optionally substituted group selected from the group consisting of acyl, $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, or sulfur; and 4-7-membered heterocyclyl having 1-2 heteroatoms independently selected from nitrogen, oxygen, or sulfur; and
each R is independently hydrogen, a protecting group, an acyl moiety, arylalkyl moiety, aliphatic moiety, aryl moiety, heteroaryl moiety, or heteroaliphatic moiety; or: two R on the same nitrogen atom may be taken with the nitrogen to form a 4-7-membered heterocyclic ring having 1-2 heteroatoms independently selected from nitrogen, oxygen, or sulfur;
to form an ester of formula x:

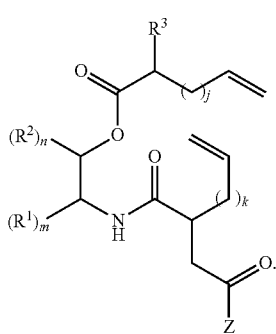

x

Step S-7
At step S-7, an ester of formula x is treated under suitable conditions to form a macrocycle of formula xi. In some embodiments, step S-7 comprises the use of a suitable ring closing metathesis catalyst. Methods of using ring closing metathesis to form macrocycles are known in the art, and include those described by Lee, D.; Sello, J.; Schreiber, S. L. *J. Am. Chem. Soc.,* 1999, 121, 10648-10649. As used herein, the term "suitable ring closing metathesis catalyst" refers to any catalyst known in the art to act as a catalyst for the ring closing metathesis reaction of two olefin moieties. In certain embodiments, the catalyst is a ruthenium alkylidene or ruthenium carbene. In some embodiments, the catalyst is a molybdenum-based species. In some embodiments, the catalyst is Grubbs $1^{st}$ generation. In some embodiments, the catalyst is Grubbs $2^{nd}$ generation. In some embodiments, the catalyst is Hoveyda-Grubbs $1^{st}$ generation. In some embodiments, the catalyst is Hoveyda-Grubbs $2^{nd}$ generation. In some embodiments, the catalyst is dichloro(3-methyl-2-butenylidene)bis (tricyclopentylphosphine) ruthenium(II). In some embodiments, the catalyst is dichloro(3-methyl-2-butenylidene)bis (tricyclohexylphosphine) ruthenium(II). In some embodiments, the catalyst is a chiral ruthenium catalyst. Methods of using and general descriptions of suitable ring closing metathesis catalysts are described in Grubbs, R. H.; *Tetrahedron,* 2004, 7117-7140; the entire contents of which are hereby incorporated by reference.

One of ordinary skill will recognize that the amount of ring closing metathesis catalyst used in step S-7 may vary. In some embodiments, about 1 mol % is used. In some embodiments, about 5 mol % is used. In some embodiments, about 10 mol % is used. In some embodiments, about 10-20 mol % is used. In some embodiments, about 20 mol % is used. In some embodiments, about 50 mol % is used. In some embodiments, about 100 mol % is used. The catalyst may be added in one portion or in multiple portions. In some embodiments, the catalyst is added in two or three portions. The catalyst may be added slowly over time using a syringe pump.

Solvents suitable for use in step S-7 include halogenated hydrocarbons (e.g., dichloromethane, chloroform, carbon tetrachloride, methyl chloroform, 1,2-dichloroethane, 1,1-dichloroethane), aromatic hydrocarbons (e.g., benzene, toluene, xylenes, ethylbenzene), or halogenated aromatic hydrocarbons (e.g., chlorobenzene, dichlorobenzenes). In certain embodiments, the solvent is a halogenated hydrocarbon or aromatic hydrocarbon. In some embodiments, the solvent is dichloromethane. In some embodiments, the solvent is benzene. In some embodiments, the solvent is toluene.

Step S-7 is typically carried out at temperatures of about 20-120° C. In some embodiments, the reaction temperature is the reflux temperature of the solvent or reaction mixture. In some embodiments, the temperature is about 100-110° C. In some embodiments, the temperature is about 75-100° C. In some embodiments, the temperature is about 35-75° C.

In some embodiments, one or more reagents may be added after the completion of step S-7 to facilitate the removal of olefin metathesis catalyst byproducts and contaminants that are not typically removed in their entirety during chromatographic purification. Such methods are known in the art and may require an incubation period that allows the reagent to work properly. In some embodiments, Pb(OAc)$_4$ is added. In some embodiments, DMSO is added. In some embodiments, resin-bound triphenylphosphine oxide is added. In some embodiments, activated carbon is added. In some embodiments, P(CH$_2$OH) is added.

In certain embodiments, the present invention provides a method comprising the steps of:
(a) providing an ester of formula x:

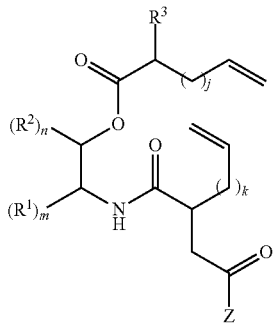

and
(b) reacting ester of formula x under suitable conditions in the presence of a suitable ring closing metathesis catalyst to form a macrocycle of formula xi:

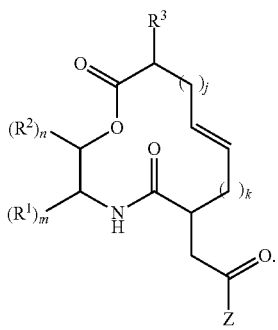

It will be appreciated that compounds of formula xi may be treated under suitable hydrogenation conditions (e.g., Pd/C, H$_2$; Wilkinson's catalyst; etc.) to reduce the double bond of the macrocycle. Suitable hydrogenation conditions are known in the art and include those described by March (supra). Such saturated macrocycles, wherein === is a single bond, are comtemplated by the present invention.

In certain embodiments, each of the aforementioned synthetic steps may be performed sequentially with isolation of each intermediate performed after each step. Alternatively, each of steps S-1, S-2, S-3, S-4, S-5, S-6, and S-7 as depicted in Scheme I above, may be performed in a manner whereby no isolation of one or more intermediates iii, iv, v, vi, viii, x, and xi is performed.

In certain embodiments, all the steps of the aforementioned synthesis may be performed to prepare the desired final product. In other embodiments, two, three, four, five, or more sequential steps may be performed to prepare an intermediate or the desired final product.

In certain embodiments, all the steps of the aforementioned synthesis may be performed using solution phase or solid phase synthetic techniques, or a combination thereof. In some embodiments, robotic techniques may be employed. In certain embodiments, automatic liquid handling reaction stations may be used. In some embodiments, parallel synthesis may be used. In some embodiments, high-throughput synthesis may be used. In some embodiments, one-by-one synthesis may be used.

Inhibition of Sonic Hedgehog Protein-Induced Transcription

The inventive compounds of formula I are thought to bind directly to the active, N-terminal fragment of the Sonic Hedgehog protein (ShhN). This activity has been observed in the Shh-LIGHT2 reporter cell line when stimulated with ShhN-conditioned medium (HCM), but it is not observed under the same conditions when a constitutively active cell line is used that lacks both alleles of the ShhN receptor Patched1 (Ptc1). These findings are consistent with compounds of formula I inhibiting Shh signaling in Shh-LIGHT2 cells by preventing ShhN from forming a functional complex with Ptc1.

None of the previously reported synthetic Shh pathway inhibitors are known to target the Shh protein itself, and none were intended to target any particular constituent of the pathway. To our knowledge, all reported examples of discoveries of small-molecule Shh signaling modulators resulted from the use of cell-based phenotypic assays. Target-based discovery of modulators of Shh signaling was expected to provide a complementary approach. Small-molecule microarray (SMM) technology has enabled the discovery of small molecules that bind target proteins of interest (Macbeath, G., Koehler, A. N., Schreiber, S. L. J. Am. Chem. Soc. 121, 7967-7968, 1999; Barnes-Seeman, D., Park, S. B., Koehler, A. N., Schreiber, S. L. Angew. Chem. Int. Ed. 42, 2376-2379, 2003; Koehler, A. N., Shamji, A. F., Schreiber, S. L. J. Am. Chem. Soc. 125, 8420-8421, 2003). It has been reported that molecules from multiple diversity-oriented synthesis (DOS) pathways, which had been covalently linked to a glass surface, could be screened for binding to a given protein in a tandem high-throughput fashion using SMMs (Burke, M. D., Berger, E. M., Schreiber, S. L. Science 302, 613-618, 2003; Burke, M. D., Berger, E. M., Schreiber, S. L. J. Am. Chem. Soc. 126, 14095-14104, 2004; Chen, C. et al. Angew. Chem. Int. Ed. 44, 2249-2252, 2005; Kumar, N., Kiuchi, M., Tallarico, J. A., Schreiber, S. L. Org. Lett. 7, 2535-2538, 2005; Lo, M. et al. J. Am. Chem. Soc. 126, 16077-16086, 2004; Stavenger, R. A., Schreiber, S. L. Angew. Chem. Int. Ed. 40, 3417-3421, 2001; Wong, J. C. et al. Chem. Biol. 11, 1279-1291, 2004).

Figure 3:
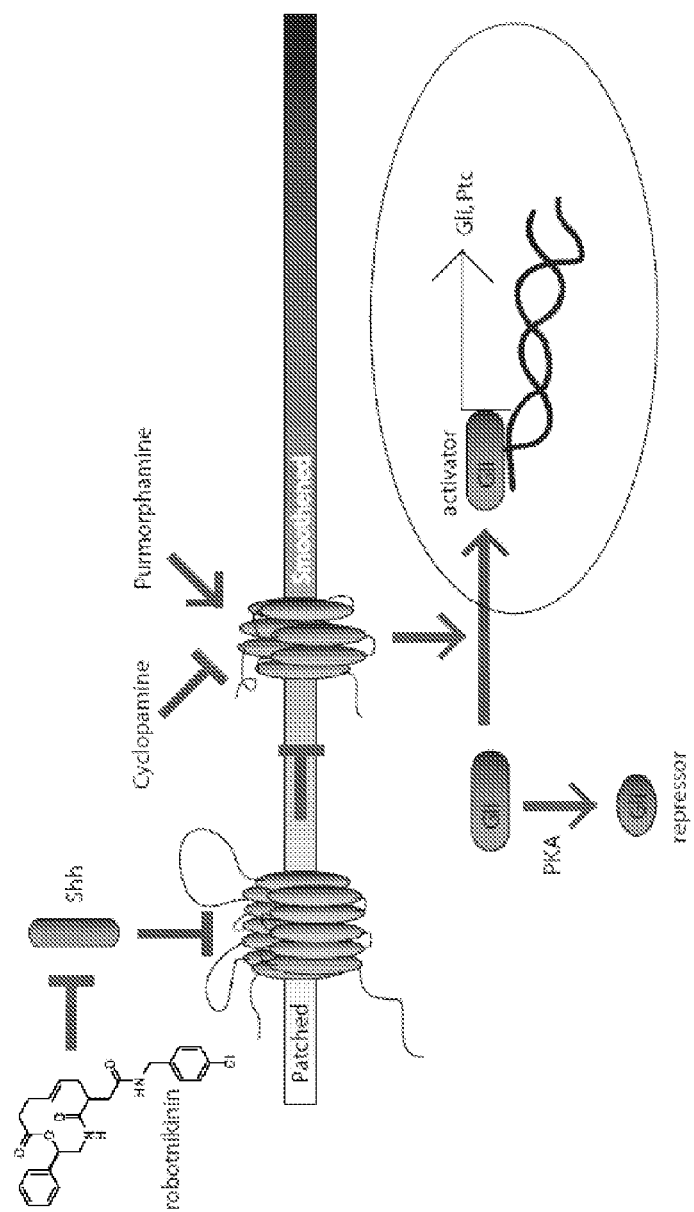
FIG. 3 depicts the Shh pathway initiated with the Hedgehog ligand binding to its receptor Patched (Ptc), which reverses Ptc inhibition of smoothened (Smo) and allows the active form of Gli1 to enter the nucleus and activate target genes which include itself and Ptc.

While not wishing to be bound by any particular theory, it is proposed that compounds of formula I inhibit Shh signaling in a concentration-dependant manner but exhibit no inhibitory activity in a cell line lacking the Ptc1 receptor, and do not exhibit an inhibitory effect in the presence of the well-characterized Smo agonist, purmorphamine. In light of the ShhN-binding properties of such macrocycles and the results of our epistasis analyses (its lack of significant Shh pathway inhibition (using Gli activity as a surrogate for pathway activity) in the Ptc1$^{-/-}$ cell line and the ability of an agonist of the downstream Smoothened to override its effects), we suggest the possibility of a novel mechanism of action involving direct targeting of the ShhN protein complex. Recent evidence has indicated that Hh signaling is facilitated by HhN binding partners Ihog, Boi, and heparin in Drosophila, and Shh binding partners (Ihog orthologs) Cdo and Boc in vertebrates (Zhang, F. et al. J. Biochem. 46, 3933-3941, 2007; Yao, S., Lum., L., Beachy, P. A. Cell 125, 343-357, 2006; Wilson, C. W., Chuang, P.-T. Cell 125, 435-438, 2006; Tenzen, T. et al. Dev. Cell 10, 647-656, 2006; Maity, T., Fuse, N., Beachy, P. A. PNAS 102, 17026-17031, 2005). The data presented herein suggest that compound of formula I interfere with the ability of the ShhN protein complex to relay its signal efficiently to Ptc1 in the Shh-LIGHT2 cell line (FIG. 3). Pathway inhibition at the Shh level illustrates an opportunity for the development of novel probes and therapeutics through which one may gain a better understanding of diseases associated with aberrant Shh-pathway activity.

Uses

Compounds of formula I may be used in vitro or in vivo. The inventive compounds may be particularly useful in the treatment of neoplasms or other proliferative diseases in vivo. The inventive compounds may also be useful in the treatment of developmental and pulmonary diseases in vivo. However, inventive compounds described above may also be used in vitro for research or clinical purposes (e.g., determining the susceptibility of a patient's disease to a compound of formula I, researching the mechanism of action, elucidating a cellular pathway or process).

In some embodiments, compounds of the present invention are used to inhibit the Shh protein or Shh pathway in cells. In some embodiments, the cells are wild type. In some embodiments, the cells are subject to one or more genetic modifications. In some embodiments, the cells are cancer cells.

In some embodiments, compounds of the present invention are provided for use in medicine. In some embodiments, the present invention provides a method of treating a proliferative disease in a subject suffering therefrom, the method comprising administering to the subject a therapeutically effective amount of a compound of formula I. In certain embodiments, the proliferative disease is a benign neoplasm. In certain embodiments, the proliferative disease is cancer. In certain embodiments, the proliferative disease is an inflammatory disease. In certain embodiments, the proliferative disease is an autoimmune disease. In certain embodiments, the proliferative disease is diabetic retinopathy.

Compounds of formula I may be used in the treatment or prevention of neoplasms. In certain embodiments, the neoplasm is a benign neoplasm. In other embodiments, the neoplasm is a malignant neoplasm.

In some embodiments, the cancer is a hematological malignancy. In certain embodiments, the cancer is a solid tumor. Exemplary cancers that may be treated using compounds of formula I include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few. In certain embodiments, compounds of formula I are used to treat pancreatic cancer. In certain embodiments, compounds of formula I are used to treat medulloblastoma. In certain embodiments, compounds of formula I are used to treat Gorlin syndrome. In certain embodiments, compounds of formula I are used to treat basal cell carcinoma.

In certain embodiments, the present disclosure provides a method for the inhibition of Sonic Hedgehog protein-induced transcription in cells, the method comprising contacting said cells with an effective amount of a compound of formula I. In certain embodiments, inventive compounds of formula I inhibit the Sonic Hedgehog pathway upstream of Ptc1. In certain embodiments, inventive compounds of formula I inhibit or repress Gli1 activity. In certain embodiments, inventive compounds of formula I destabilize a dimeric Shh complex.

In some embodiments, compounds of formula I may be used to block hair regrowth. In certain embodiments, a compound of formula I, or composition thereof, may be applied to the skin post-depilation to prevent or slow hair regrowth. In some embodiments, a compound of formula I, or composition thereof, may be applied to the skin post-depilation to prevent or slow hair follicle development.

In some embodiments, compounds of formula I may be used in the treatment of interstitial pneumonitis. In some embodiments, compound of formula I may be used in the treatment of interstitial pulmonary fibrosis. In some embodiments, the pulmonary fibrosis is bleomycin-induced. In some embodiments, the pulmonary fibrosis is not bleomycin-induced.

In certain embodiments, compounds of formula I may be used in the treatment of developmental disorders. In certain embodiments, the present invention provides a method of treating a developmental disorder, the method comprising administering to the subject a therapeutically effective amount of a compound of formula I. In some embodiments, the developmental disorder is phocomelia. In some embodiments, the developmental disorder is cyclopia. In some embodiments, the developmental disorder is treated at a prenatal stage. In some embodiments, the developmental disorder is treated in an intrauterine fashion. In some embodiments, the developmental disorder is treated at a post-natal stage. In some embodiments, the subject is human. In some embodiments, the subject is a human embryo.

In some embodiments, the present invention provides a method of controlling stem cell differentiation, wherein the method comprises contacting one or more stem cells with a compound of formula I. In some embodiments, the resulting differentiation is terminal. In some embodiments, the resulting differentiation is non-terminal. In some embodiments, differentiation is from a stem cell to an intermediate cell stage (such as a progenitor cell). In some embodiments, differentiation is from a progenitor cell to a more specialized cell. In some embodiments, differentiation is from a definitive endoderm cell to a pancreatic precursor cell. In some embodiments, differentiation is from a stem cell to an endoderm cell. In some embodiments, the present invention provides a method of controlling cell dedifferentiation, wherein the method comprises contacting one or more cells with a compound of formula I, thereby resulting in a stem cell.

In certain embodiments, compounds of formula I are used to control cell differentiation. In certain embodiments, the differentiation is related to cellular development. In certain embodiments, the differentiation is related to organ development. In certain embodiments, the differentiation is related to organ system development. In certain embodiments, the differentiation is related to organism development.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999, the entire contents of which are hereby incorporated by reference.

In certain embodiments, inventive compounds are useful in treating a subject in clinical remission. In some embodiments, the subject has been treated by surgery and may have limited unresected disease.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in inhibiting Sonic Hedgehog Protein-induced transcription. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term acyl as used herein refers to a moiety that includes a carbonyl group oro a group having the general formula —C(═O)R, where R is alkyl, alkenyl, alkynyl, aryl, carbocylic, heterocyclic, or aromatic heterocyclic. An example of an acyl group is acetyl.

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-12 carbon atoms. In another embodiment, the alkyl group employed contains 1-8 carbon atoms. In still other embodiments, the alkyl group contains 1-6 carbon atoms. In yet another embodiment, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents.

In general, the terms aryl and heteroaryl, as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term carboxylic acid as used herein refers to a group of formula —CO$_2$H.

The terms halo and halogen as used herein refer to an atom selected from fluorine, chlorine, bromine, and iodine.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2- cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term arylalkyl refers to alkyl groups in which a hydrogen atom has been replaced with an aryl group. Such groups include, without limitation, benzyl, cinnamyl, and dihyrocinnamyl.

The term heteroatom means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term unsaturated, as used herein, means that a moiety has one or more units of unsaturation.

As used herein, the term partially unsaturated refers to a ring moiety that includes at least one double or triple bond. The term "partially unsaturated" is intended to encompass rings having multiple sites of unsaturation, but is not intended to include aryl or heteroaryl moieties, as herein defined.

Additionally, unless otherwise stated, structures depicted herein are also meant to include compounds that differ only in the presence of one or more isotopically enriched positions of the compound. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxy methyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, trip-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)-amine, quaternary ammonium salts, N-benzylamine, N-di(4-methoxyphenyl)methylamine, N-5-dibenzosuberylamine, N-triphenylmethylamine (Tr), N-[(4- methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

In another aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically acceptable organic primary, secondary, tertiary, or quaternary amine. Salts derived from appropriate bases include alkali metal, alkaline earth metal, ammonium and $N^+$ ($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Representative organic amines useful for the formation of base addition salts include ethylamine, diethylamine, ethylenediamine, ethanolamine, diethanolamine, piperazine and the like. (See, for example, Berge et al., supra).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

As used herein and in the claims, the singular forms "a", "an", and "the" include the plural reference unless the context clearly indicates otherwise. Thus, for example, a reference to "a compound" includes a plurality of such compounds.

Formulations

Compounds of the present invention may be combined with a pharmaceutically acceptable carrier to form a pharmaceutical composition. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such carriers as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Drug-eluting forms include coated or medicated stents and implantable devices. Drug-eluting stents and other devices may be coated with a compound or pharmaceutical preparation and may further comprise a polymer designed for time-release.

In certain embodiments, a compound or pharmaceutical preparation is administered orally. In other embodiments, the compound or pharmaceutical preparation is administered intravenously. In certain embodiments, a compound is attached via a cleavable linker to a solid support that is administered with a catheter. Alternative routes of administration include sublingual, intramuscular, and transdermal administrations.

When the compounds of the present invention are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, an aerosol, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits including the combination of a compound of the present invention and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

EXAMPLES

Example 1

A screen of the ShhN protein was performed using small molecule microarrays (SMMs) containing a collection of approximately 10,000 diversity-oriented synthesis (DOS) compounds and natural products that has been reported by Koehler and co-workers, in which the entire library was arrayed on a single microscope slide (Bradner, J. E. et al. Chem. Biol. 13, 493-504, 2006). Three SMM slides were used to screen for small molecules that bind the ShhN protein, while two slides were designated as protein-free negative controls. Binding was detected by the use of a biotinylated anti-ShhN antibody, followed by incubation with streptavidin alexa 647. The treated slides were then scanned with a microarray plate reader. The duplicate negative controls eliminated many false positives, while screening in triplicate increased the accuracy of the results. Microarray image analysis was performed with GenePix Pro software (Molecular Devices, Sunnyvale Calif.). Initially, the software facilitated the elimination of false positives present on the negative control slides. The software was then used to select all remaining possible positives in the ShhN-treated slides that exceeded our criteria for fluorescence intensity threshold. In addition to high relative signal intensity, the presence of a given hit across all replicates was considered for compound selection. In the ShhN SMM screen, two macrocycles, AML1 and AML2, (FIG. 1a,b) emerged as intriguing assay positives, and were retested for binding to ShhN via surface plasmon resonance (SPR) (FIG. 1c,d). The compounds exhibited binding to ShhN in a concentration-dependant fashion, and the $K_D$ values for both compounds were approximately 10 μM (by fitting to kinetic data).

We examined the activity of the new series of AML compounds in Shh-LIGHT2 cells (ATCC, Manassas Va.) (Tapaile, J., et al., 2000 supra), which is an NIH3T3 cell line with a Gli-dependent firefly luciferase reporter. These cells can be used to demonstrate the efficacy of Shh pathway inhibitors (cyclopamine) and activators (purmorphamine and SAG) (Chen et al. and Tapaile et al., supra; Surajit, S., Chen, J. K. Nat. Chem. Biol. 2, 29-30, 2006). Shh pathway activity was inferred by measuring firefly luciferase levels after a 30 h incubation with compound in the presence of HCM. The compounds exhibited moderate Hh pathway inhibition (FIG. 1e,f) and did not demonstrate cytotoxicity at any of the experimental concentrations based on a cell titer viability assay run in parallel. This raised the possibility that the ShhN-binding was related to moderate Shh pathway inhibition.

FIG. 1 depicts the following: characterization of the original SMM hits, AML1 and AML2; structures of the original SMM hits, AML1 and AML2 (a and b); and SPR plots of AML1 and AML2, respectively, binding to purified ShhN (c and d). The plots show normalized response units (RUs) on the y-axis and time (s) on the x-axis. The concentrations plotted are (AML1) 1.56 μM, 3.13 μM, 6.25 μM, 12.5 μM, and 25 μM and (AML2) 0.78 μM, 1.56 μM, 3.13 μM, 6.25 μM, 12.5 μM, and 25 μM, in order of increasing normalized RUs. Luminescence plots for a Gli-dependent firely luciferase reporter gene assay (Wang et al., supra) of compounds AML1 and AML2, respectively, at the indicated concentrations (e and f). HCM represents a positive control for ShhN-conditioned medium, and LCCM, low-calf serum containing medium, represents a negative control. The assays were performed at 0.25% (v/v) DMSO. Each value represents the average of five experiments, with the error bar denoting the standard deviation.

To investigate further the possibility that the ShhN-binding was related to the Shh pathway inhibition, a set of macrocycle analogs of AML1 and AML2 was synthesized (see Example 2). From the set, several compounds were shown to exhibit concentration-dependent and stoichiometric binding to purified ShhN in SPR experiments. In particular, a 12-membered macrocycle from this set, which we have named robotnikinin, showed increased ShhN-binding. Based on SPR experiments, robotnikinin (FIG. 2a) demonstrated ShhN-binding capacity at concentrations between 1.56 μM and 25 μM (FIG. 2b) and displayed a longer dissociation time than AML1 and AML2. When this compound was tested in Shh-LIGHT2 cells (Tapaile, J., et al., 2000 supra), it showed concentration-dependent inhibition of ShhN-induced pathway activation (FIG. 2c). Additionally, at concentrations above 30 μM the macrocycle exhibited comparable inhibition relative to treatment with 6.25 μM cyclopamine in Shh-LIGHT2 cells. No significant cytotoxicity was observed as judged by cell titer measurements using a cell viability assay.

To explore further the potential mechanism of Shh pathway inhibition involving direct perturbation of the ShhN protein complex, the same compounds were tested in a $Ptc1^{-/-}$ cell line derived from mouse embryos lacking Ptc1 function. The cell line had both Ptc1 alleles replaced with a β-galoctosidase (β-gal) reporter (Surajit et al., supra). Because Ptc1 inhibits Hh pathway activation by repressing Smo function, removing both Ptc1 alleles results in constitutive pathway activation. Small-molecule pathway inhibitors that act downstream of Ptc1 remain active in this cell line. In the $Ptc1^{-/-}$ cell line, Shh pathway activity is proportional to the β-gal levels observed after 30 h of incubation with compound. No significant difference was observed when the $Ptc1^{-/-}$ cell line was treated with HCM or low serum-containing culture medium (LCCM), confirming that with the Ptc1 receptor absent, the Shh pathway is constitutively activated and Shh does not increase Shh pathway activation. Previous studies have demonstrated that cyclopamine, whose target (Smo) is downstream of Ptc1 (Chen, J. K., Taipale J., Cooper, M. K.; Beachy, P. A. Genes Dev. 16, 2743-2748, 2002), is effective at ablating β-gal reporter activity in this cell line. In our study, treatment with 6.6 μM cyclopamine resulted in significant pathway inhibition. In contrast, no pathway inhibition was observed using robotnikinin at any of the concentrations tested after normalizing luminescence data for cell titer (FIG. 2c). These results support a model in which this small molecule inhibits the Shh pathway upstream of Ptc1 in Shh-LIGHT2 cells. The model predicts that treatment of Shh-LIGHT2 cells with the Smo agonist purmorphamine would override the inhibitory effect of robotnikinin. When we tested the model by co-administering 3.6 μM purmorphamine in addition to various concentrations of robotnikinin, virtually all of the inhibitory effect was eliminated (FIG. 2c).

Figure 2:
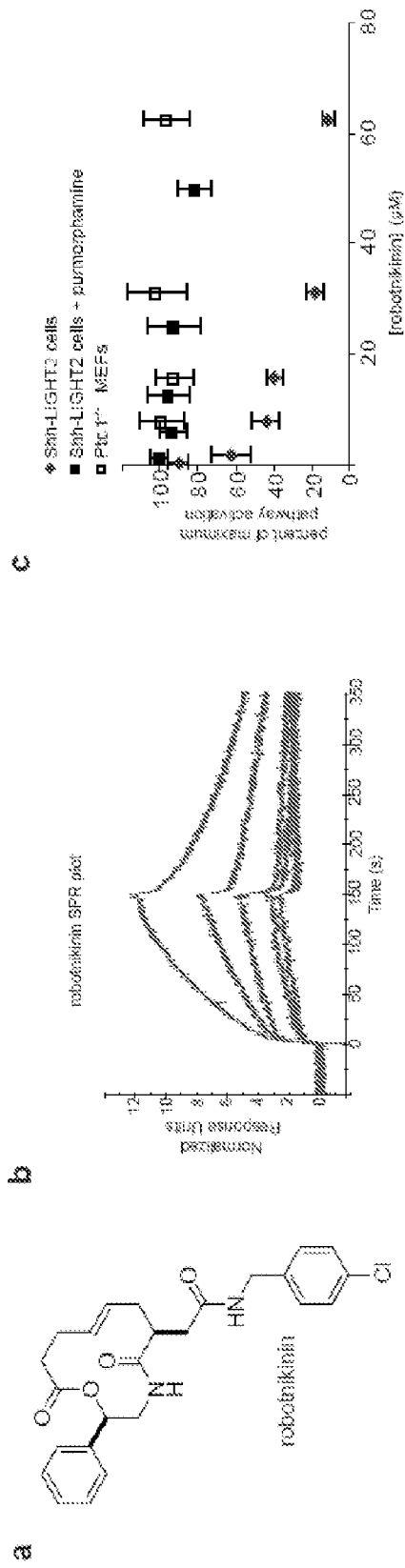
FIG. 2 depicts the structure of robotnikinin (a); SPR curve of robotnikinin showing concentration-dependent binding to purified ShhN (b); and inhibition of Gli signaling by robotnikinin in Shh-LIGHT2 cells stimulated with ShhN-conditioned medium, relative to 6.25 µM cyclopamine (c).

FIG. 2 depicts the following: (a) The structure of robotnikinin. (b) SPR curve of robotnikinin showing concentration-dependent binding to purified ShhN. Normalized RUs are plotted over a time course. The concentrations plotted are 1.56 μM, 3.13 μM, 6.25 μM, 12.5 μM, and 25 μM, in order of increasing RUs. (c) Inhibition of Gli signaling by robotnikinin in Shh-LIGHT2 cells stimulated with ShhN-conditioned medium, relative to 6.25 µM cyclopamine (a small-molecule inhibitor of Smoothened). Shh-LIGHT2 cells stimulated with ShhN-conditioned medium along with 3.6 µM purmorphamine (a small-molecule activator of Smoothened) showed negligible inhibition at the indicated concentrations of inhibitor. When a Ptc1−/− MEF cell line was treated with robotnikinin at the indicated concentrations, pathway inhibition was not observed, in contrast to the results observed in (Ptc1-containing) Shh-LIGHT2 cells. Each data point represents the average of five experiments, and error bars represent standard deviations. All data were normalized for cell titer.

Example 2

We developed a diversity-oriented synthesis pathway, designated the amide-macrolactone library (AML) pathway, that was readily applicable to both solid and solution phase library synthesis of a diverse array of non-natural macrolactones (Scheme 2) (Lee, et al., supra). Starting from commercially available γ-unsaturated pentenoyl chloride, the Evans oxazolidinone (Evans, D. A.; Ellman, J. A. *J. Am. Chem. Soc.* 1989, 111, 1063-1072), and readily available chiral amino alcohols, diverse macrolactone scaffolds can be accessed in just nine steps. Following an asymmetric Evans alkylation with α-bromo-tert-butyl acetate, which proceeded with over 95:5 diastereoselectivity (as determined by $^1$H NMR) the tert-butyl ester was cleaved with TFA. The resulting acid was submitted to standard amine coupling conditions in the presence of a variety of amino alcohols. At this point in the synthesis, the opportunity of loading the resulting alcohol onto polystyrene macrobeads arises (Blackwell, H. E.; Pérez, L., Stavenger, R. A.; Tallarico, J. A.; Eatough, E. C.; Folley, M. A.; Schreiber, S. L. *Chem. and Biol.* 2001, 8, 1167-1182). After cleaving the chiral auxiliary under standard literature conditions, the resulting acid was coupled with a variety of commercially available chiral amino alcohols. The acyclic macrolactone precursors were afforded by coupling reactions with acids of different chain lengths bearing terminal olefin groups. A final RCM (Grubbs, R. H.; Chang, S. *Tetrahedron* 1998, 54, 4413-4450) reaction was employed for ring closure and macrolactone formation. This diversity-synthesis pathway is suited for both solid phase split-pool and solution phase library synthesis. With the one-bead-one stock solution approach (Clemons, P. A.; Koehler, A. K.; Wagner, B.; K.; Springings, T. G.; Spring, D. R.; King, R. W.; Schreiber, S. L. *Chem and Biol.* 2001, 8, 1183-1195) a macrolactone library consisting of 2070 compounds was synthesized, where the 12, 13 and 14-membered macrocycles had >90% purity respectively (See Example 3).

Scheme 2. Amide-macrolactone pathway. A diversity-oriented synthesis pathway yielding an array of macrocyclic compounds. 12-, 13-, and 14-membered macrocycles can be generated starting from simple, commercially available building blocks. Note that both enantiomers of the Evans oxizolidinone were used to construct macrocycles with the R₁ building block in both stereochemical orientations in the solid and solution phase libraries. AML1 and AML2, previously reported to bind purified ShhN based on small molecule microarray (SMM) experiments verified with surface plasmon resonance (SPR).

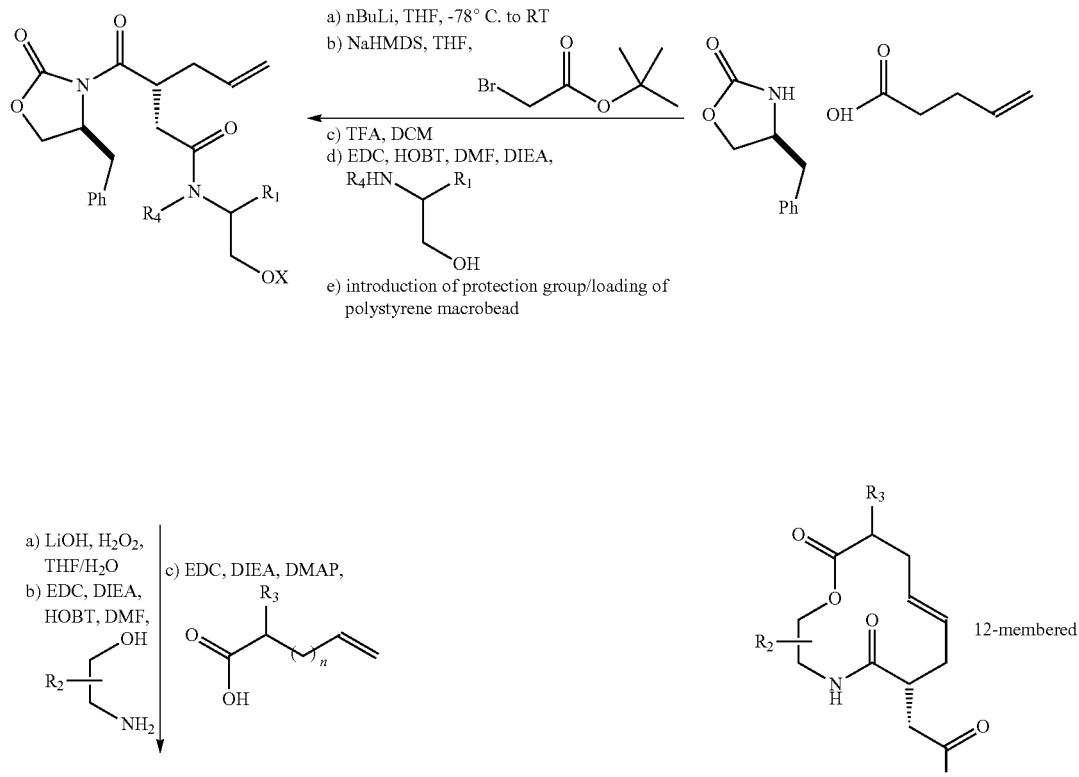

-continued

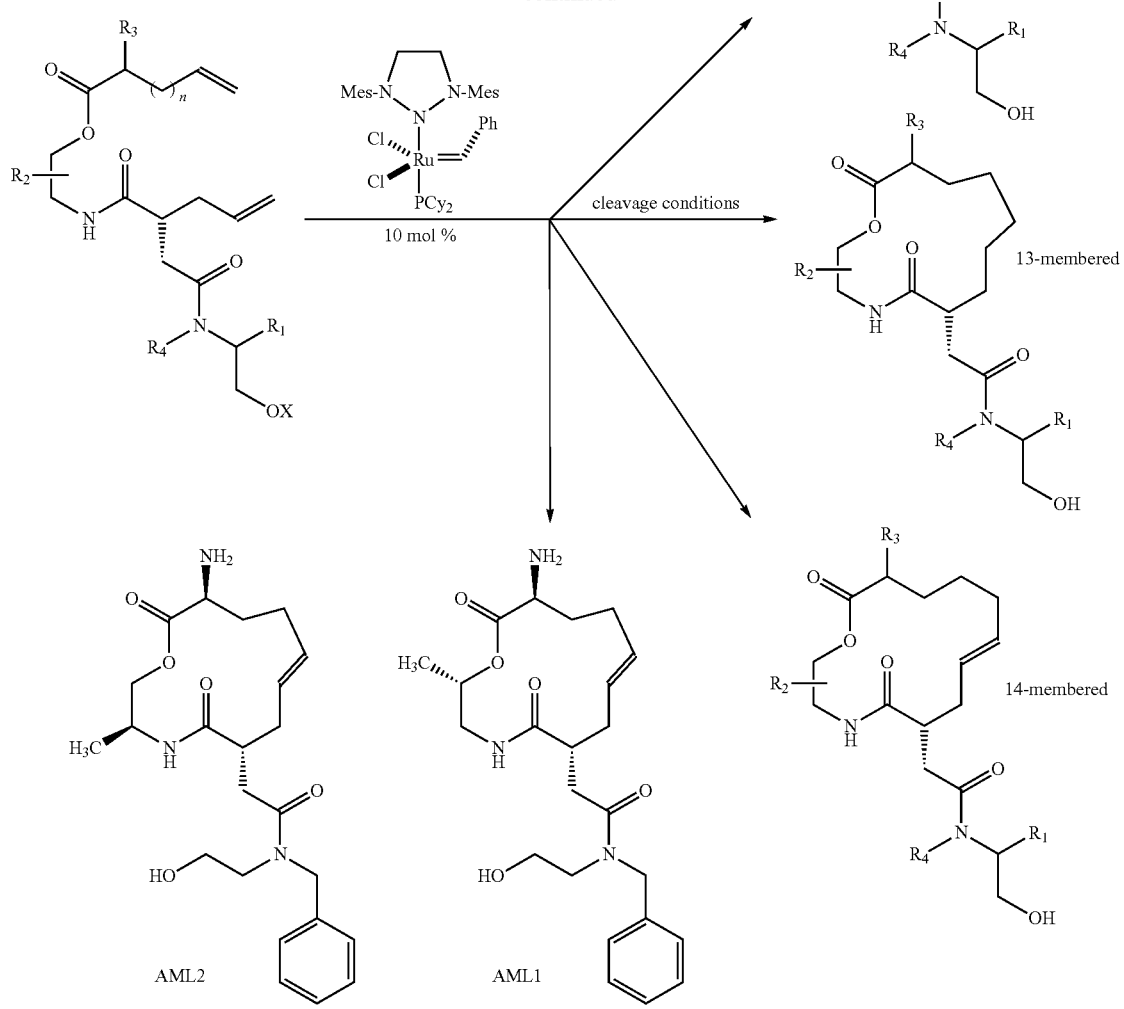

X = polystyrene macrobead or protecting group

Compounds from the 2070-member AML library were arrayed onto small molecule microarrays (SMMs) (Macbeath, G., Koehler, A. N., Schreiber, S. L. *J. Am. Chem. Soc.* 1999, 121, 7967-7968; Barnes-Seeman, D., Park, S. B., Koehler, A. N., Schreiber, S. L. *Angew. Chem. Int. Ed.* 2003, 42, 2376-2379; Koehler, A. N., Shamji, A. F., Schreiber, S. L. *J. Am. Chem. Soc.* 2003, 125, 8420-8421) and screened for binding to purified Sonic Hedgehog N-terminal peptide (ShhN) (Bradner, J. E. et al. *Chem. Biol.* 2006, 13, 493-504). We designed a solution phase ShhN-biased AML library focusing on 12, 13 and 14-membered analogues, from which robotnikinin was discovered (Table 3). All of the Shh-biased AML library compounds bound purified ShhN in a stoichiometric manner, as verified by Surface Plasmon Resonance (SPR) experiments with immobilized ShhN.

The most widely characterized target gene of the Shh pathway is Gli1, which is upregulated in a variety of tissues, and is a robust and reliable marker of pathway activation (Ingham, P. W., McMahon, A. P. *Genes and Dev.* 2001, 15, 3059-3087). Therefore, compounds that repress Gli1 activity would be putative inhibitors of Shh signaling in the cell line in which the experiments were carried out. We examined the activity of the new series of AML compounds in the Shh Light II cell line, or ShhL2 line (ATCC, Manassas Va.) (Tapaile, J., et al., 2000 supra), which is an NIH3T3 line transformed with a Gli-luciferase construct along with zeocin and G418 resistance vectors to select for the transformed strains during normal culturing. From the ShhN-biased AML library, robotnikinin (FIG. 4) showed strong concentration dependent Gli1 suppression, as measured with the Gli1-luciferase construct of the ShhL2 cell line which is characteristic of Shh pathway inhibition (Chen, J. K., Tapaile, J., Young, K. E., Maiti, T., Beachy, P. A. *PNAS* 2002, 99, 14071-14076). However, we hypothesized that if the interaction of robotnikinin was truly specific for ShhN, closely related analogs would have similar activity, while library members having differences in stereochemistry or ring size would have diminished abilities to suppress Gli1 activity.

Figure 4:
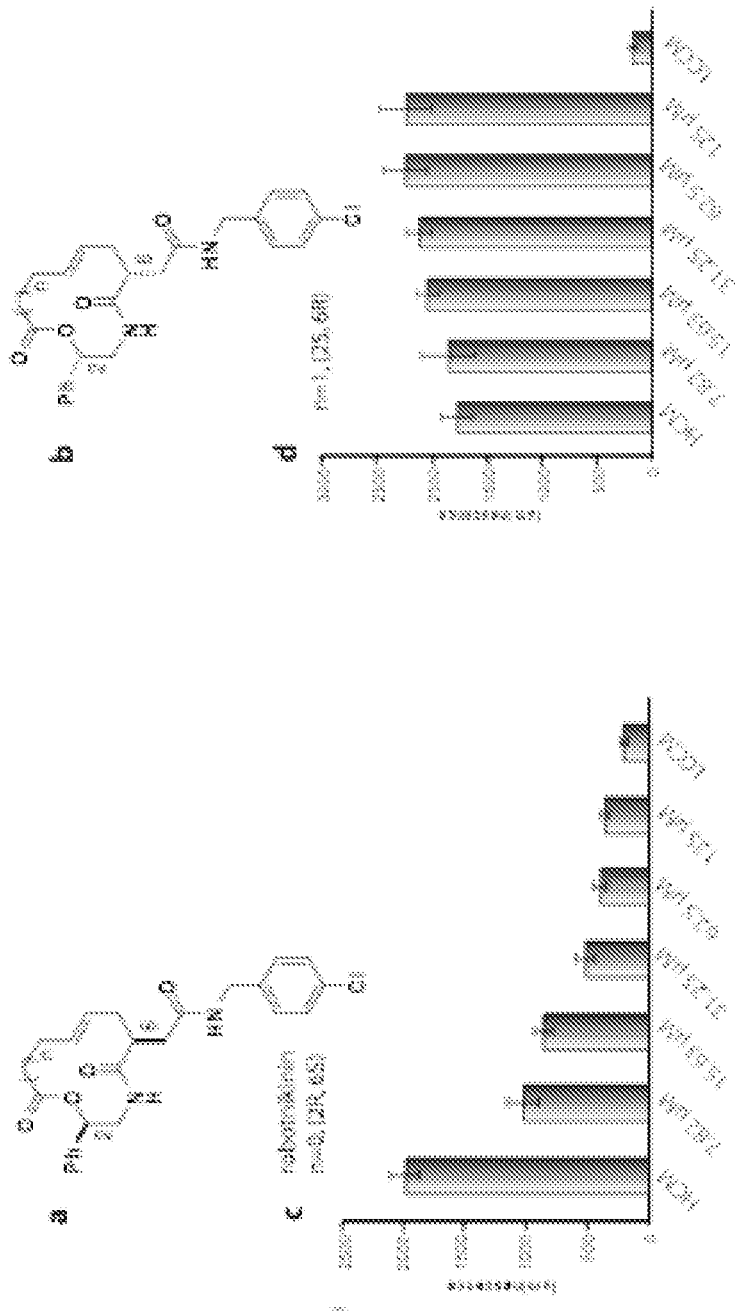
FIG. 4 depicts the structure of robotnikinin (a); the structure of a robotnikinin analog with an extra methylene unit inserted in the macrocycle and stereogenic centers in the opposite configuration of robotnikinin (b); and dose response curves of robotnikinin and a robotnikinin analog, respectively, in an ShhL2 cell line (c and d).
Figure 5:
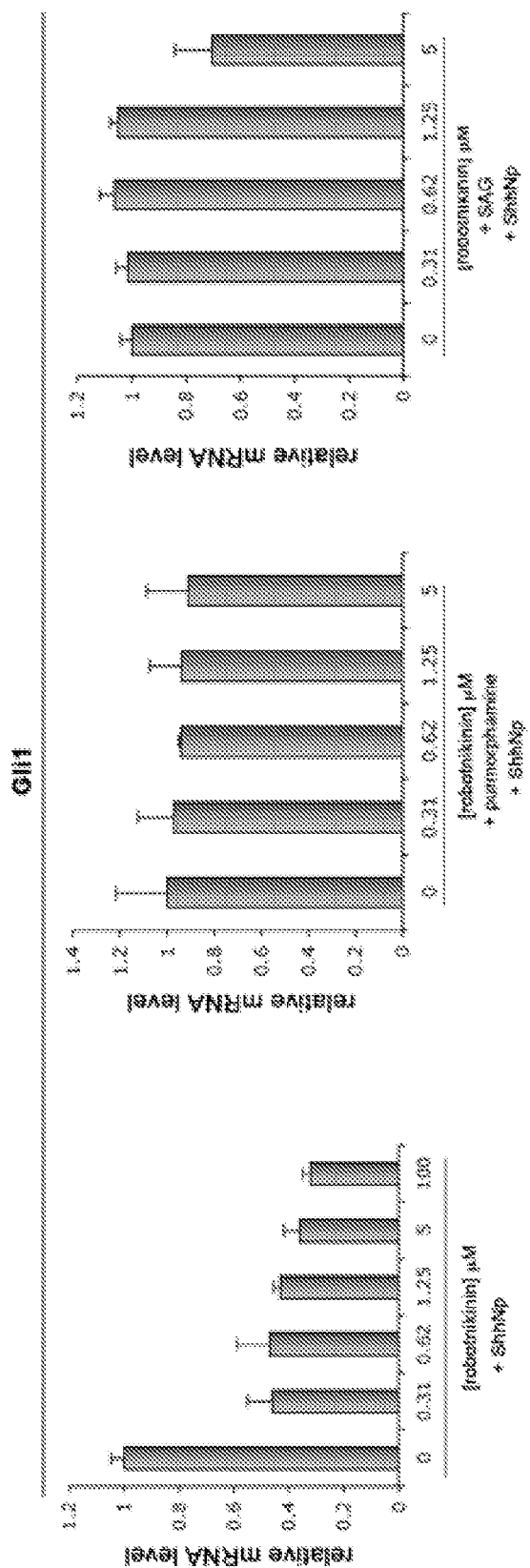
FIGS. 5 and 6 depict the results of experiments with primary human keratinocytes treated with robotnikinin. Each data point represents the average of five experiments, and error bars represent standard deviations. All data were normalized for cell titer. The results indicate that robotnikinin lowers levels of endogenous Gli1 (FIG. 5) or Gli2 (FIG. 6) mRNA (analyzed by qPCR) in primary human keratinocytes in a dose-dependent manner; this effect is blocked by the co-administration of Smo agonists purmorphamine and SAG.
Figure 6:
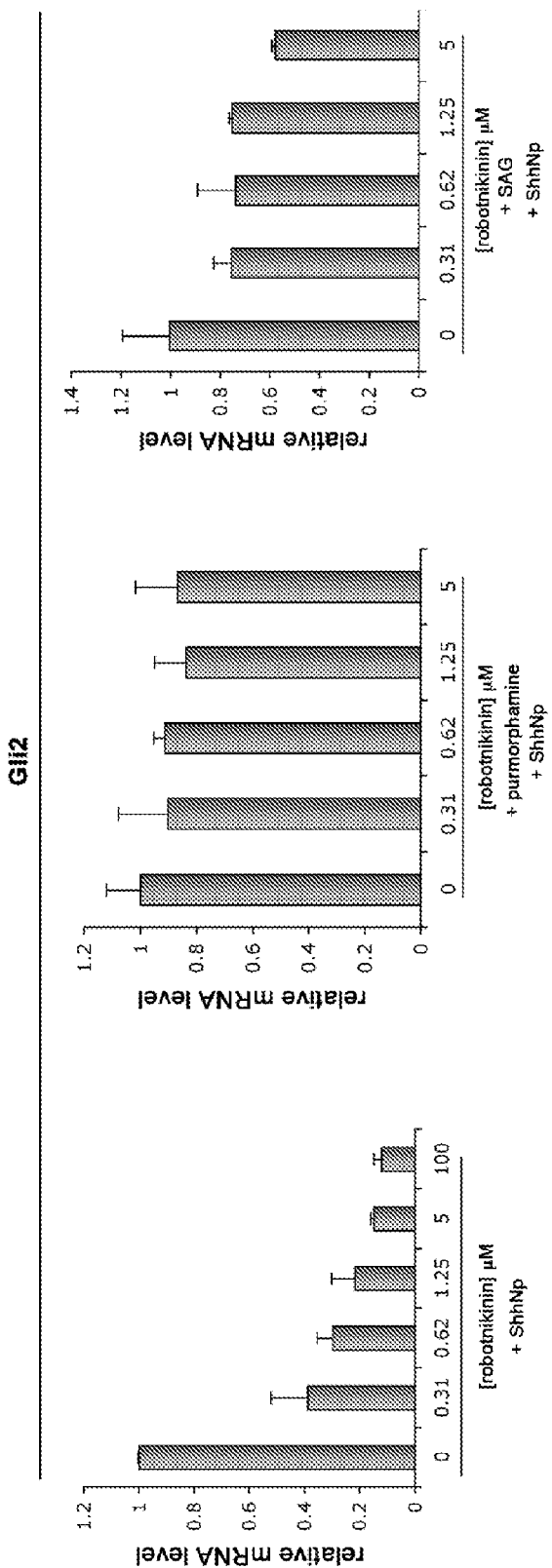
Figure 7:
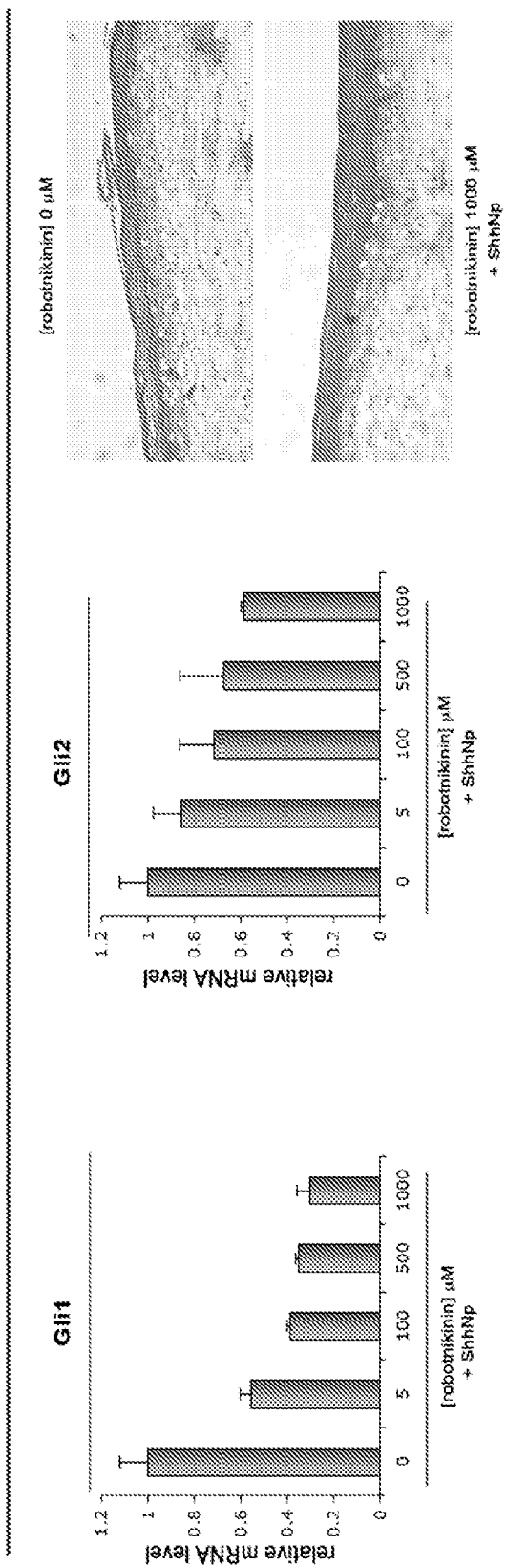
FIG. 7 depicts the results of experiments with synthetic skin prepared by populating dehydrated collagen matrix with primary human keratinocytes. Following incubation with robotnikinin, the primary human synthetic skin tissue was analyzed by qPCR for levels of Gli1 and Gli2 transcripts.

By inserting a single methylene unit into the scaffold of robotnikinin and reversing the orientation of the two stereogenic centers, Gli1 suppression was entirely ablated (FIG. 4). Furthermore, neither compound displayed cytotoxicity at any concentration as measured by Cell Titer Glo (Promega, Madison, Wis.).

We next tested the full stereochemical matrix of related compounds in the ShhL2 Gli1 reporter assay (Table 1). The stereochemical inverse of robotnikinin (n=1, 2S, 6R) had reduced activity with an $EC_{max}$ reaching only 60% of the inhibitory capacity of cyclopamine, and an $EC_{50}$ of approximately 15 μM. The corresponding 13- and 14-membered compounds (n=2 or 3, 2S, 6R) had no detectable activity in the ShhL2 cell line at concentrations ranging from 3.9 μM to 125 μM. While the $EC_{50}$ value of robotnikinin (n=1, 2R, 6S) was approximately 4 μM, and the % $EC_{max}$ of cyclopamine was found to be 91%, increasing the ring size by one methylene unit (n=2, 2R, 6S) raised the $EC_{50}$ value to approximately 15 μM and the $EC_{max}$ value to approximately 125 μM, although both compounds retained similar abilities for maximum repression of Gli1 activity (Table 3). The 14-membered analog to robotnikinin (n=3, 2R, 6S) had no detectable Gli1 suppression. Without wishing to be bound by any particular theory, it is thought that the increased flexibility inherent in the 13- and 14-membered macrolactones, relative to their 12-membered counterpart, may have decreased the specificity of their ShhN binding in the context of cellular physiology of the ShhL2 line.

We also investigated the effect of more subtle stereochemical alterations in the robotnikinin scaffold in the context of Gli1 repression in the ShhL2 line. When the stereochemistry was altered to the (n=1, 2R, 6R) configuration with the identical 12-membered ring size, the % CI dropped to 68% from 91%. Adding another methylene unit to the macrolactone scaffold (n=2, 2R, 6R) reduced the overall potency with a % CI that was 20% lower than the parent compound robotnikinin, but the 14-membered macrolactone analogue (n=3, 2R, 6R) had significantly decreased potency, with a % CI that was only 37% relative to cyclopamine. The robotnikinin diastereomer (n=1, 2S, 6S) displayed cytotoxicity above about 16 μM only and modest inhibitory activity at the highest non-cytotoxic concentration. The related 13-membered macrolactone (n=2, 2S, 6S) resulted in a 5-fold decrease in the $EC_{50}$, from 4 μM to 20 μM, but only a modest 20% drop in the % CI relative to robotnikinin. The 14-membered analogue (n=3, 2S, 6S) was found to be cytotoxic above 31 μM, and had dramatically reduced potency with a % CI only 50% at the highest non-cytotoxic concentration. The related compounds without substituents at the 2-position featured relatively decreased potency, although at extremely high concentrations several of these compounds displayed % CI levels at approximately 70% (Table 3).

TABLE 3

ShhL2 activity of Robotnikinin analogues. Robotnikinin analogues were synthesized in solution phase and tested in the ShhL2 cell line. n = 1 designates 12, 13 and 14-membered macrocycles, respectively. The stereochemical designation of n/a designates the absence of a substituent at that position.

| (n, 2, 6) | Gli1 $EC_{50}{}^a$ | Gli1 $EC_{max}$ | % CI[b] | Cytotoxicity[c] |
|---|---|---|---|---|
| (1, n/a, R) | 15 μM | 125 μM | 50%[d] | none |
| (2, n/a, R) | 31 μM | 125 μM | 66% | none |
| (3, n/a, R) | 30 μM | 125 μM | 53% | none |
| (1, n/a, S) | 60 μM | 125 μM | 55%[d] | none |
| (2, n/a, S) | 70 μM | 125 μM | 74% | none |
| (3, n/a, S) | 60 μM | 125 μM | 70%[d] | none |
| (1, S, R) | 15 μM | 125 μM | 60%[d] | none |
| (2, S, R) | n/a | n/a | n/a | none |
| (3, S, R) | n/a | n/a | n/a[d] | none |
| (1, S, S) | 10 μM | 15.6 μM | 57%[d] | >15.6 μM |
| (2, S, S) | 20 μM | 125 μM | 71%[d] | none |
| (3, S, S) | 15.6 μM | 31 μM | 50%[d] | >31 μM |
| (1, R, S) | 4 μM | 62.5 μM | 91%[d] | none |
| (2, R, S) | 15 μM | 125 μM | 93%[d] | none |
| (3, R, S) | n/a | n/a | n/a | none |
| (1, R, R) | 7 μM | 62.5 μM | 68% | none |
| (2, R, R) | 4 μM | 15.6 μM | 71% | none |
| (3, R, R) | 5 μM | 15.6 μM | 37% | none |

[a]Gli1 activity was determined with Bright Glo luciferase assay system (Promega: Madison, WI). Values represent approximations based on concentration curves (see supporting information)

[b]% CI denotes % cyclopamine inhibition, or the percentage of inhibitory effect relative to the $EC_{max}$ of cyclopamine

[c]Cytotoxicity measurements were made with Cell Titer Glo (Promega: Madison, WI).

[d]These data may be taken relative to mock treatment, which has resulted in luciferase reporter values comparable to 6 μM cyclopamine. For cytotoxic compounds, % $EC_{max}$ was calculated with respect to the highest effective non-cytotoxic concentration.

The ShhN-binding capacities of the robotnikinin analogues present the possibility, that like robotnikinin, other compounds in this class inhibit Shh pathway related Gli1 expression by interfering with the ability of Shh to interact with its receptor. Differences in ring size and stereochemistry may lead to alterations in the nature and possible location of the binding, which may account for differences in the degree of biological activity. Furthermore, it has been recently reported that Shh is presented to its receptor as a 1:1 dimer along with heparin, heparin sulfate and other associated proteins that have equilibrium binding constants to Shh in the low micromolar range.

Without wishing to be bound by any particular theory, we hypothesize that the active compounds perturb the stability of the physiologically relevant Shh protein complex, and may perturb binding interactions between Shh and its associated proteins before it can efficiently interact with the Ptc receptor (FIG. 3). Initial studies in a mouse embryonic fibroblast (MEF)-derived ptc$^{-/-}$ cell line with a Gli1-β-galactosidase reporter indicated that the compounds listed in Table 1 are not effective at Gli1 repression without the intact Ptc receptor (see FIG. 1c). Taken together, the data suggest that the AML compounds that have been shown to be active in the context of Shh pathway inhibition may exert their influence upstream of Ptc, at the Shh level.

Example 3

Solid-Phase Synthesis of Certain Compounds of Formula I

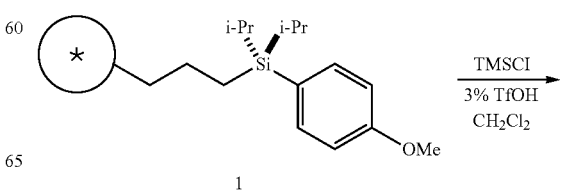

1

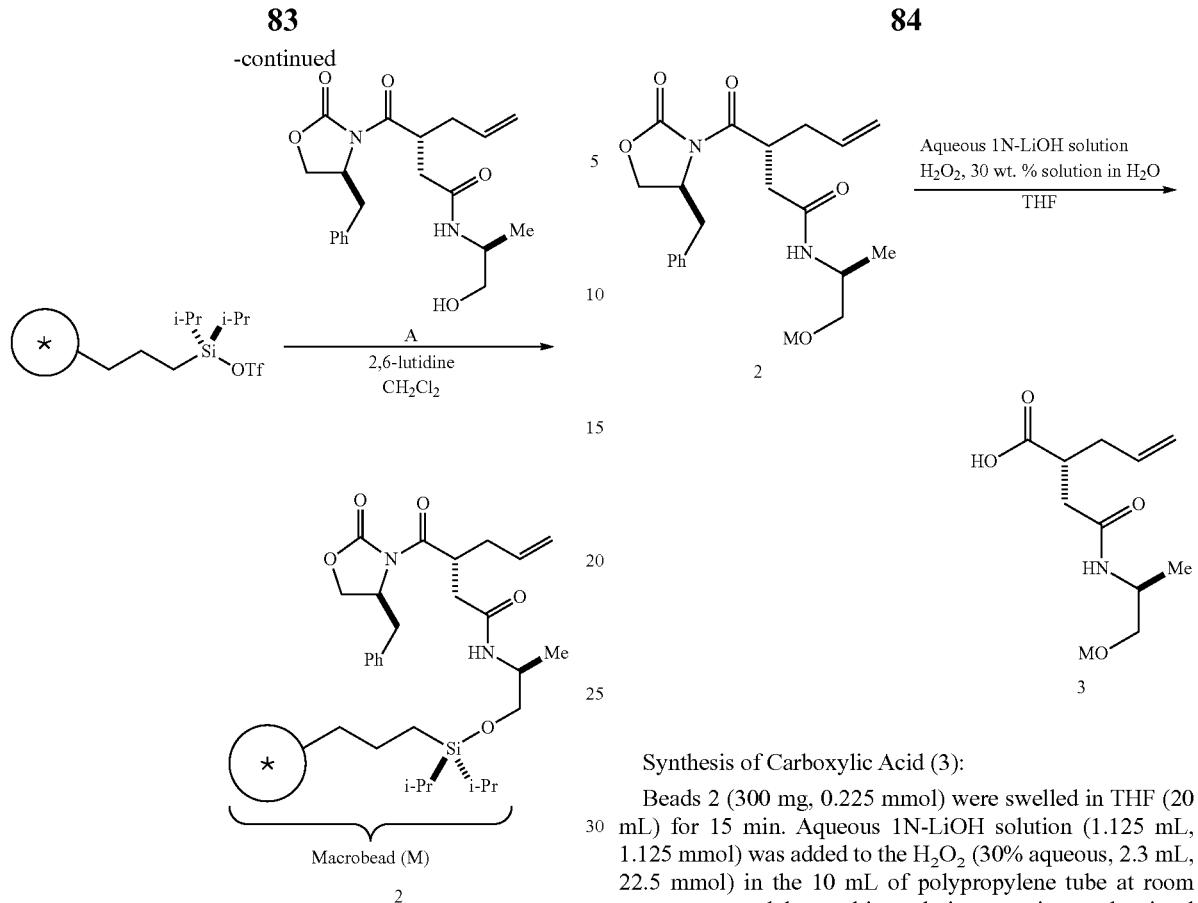

Loading Primary Alcohol A.

3-[Diisopropyl(p-methoxyphenyl)silyl]propyl functionalized macrobeads 1 (300 mg, 1.4 mmol/g, 0.42 mmol) in a 20 mL polypropylene tube was flushed with argon for a few minutes and allowed to swell in $CH_2Cl_2$ (5 mL) for 15 min. The solvent was then removed from the tube via argon push. The colorless beads were resuspended in a 2.5% (v/v) solution of TMSCl in $CH_2Cl_2$ (7.5 mL) for 30 min. The beads were filtered and washed thrice with $CH_2Cl_2$ (5 min each time) and suspended in a 3% (v/v) solution of trifluoromethanesulfonic acid (7.32 mL, 2.52 mmol) in $CH_2Cl_2$ for 30 min during which the reaction vial was shaken periodically. The beads were filtered and washed thrice with $CH_2Cl_2$ (2 min. each time) and then resuspended in a minimum volume of $CH_2Cl_2$ (1.5 mL). Freshly distilled 2,6-lutidine (576 μL, 5.04 mmol) was added followed by primary alcohol A (768 mg, 2.1 mmol). The polypropylene tube was then shaken for 12 h. The beads were then filtered, suspended and rinsed with $CH_2Cl_2$ (4×5 min each time), and dried under high vacuum overnight. The loaded resin 2 weighed 347 mg. The beads (25.6 mg) were subjected to the cleavage conditions, which yielded 7.2 mg (0.0192 mmol) of the crude product (0.75 mmol/g of loading, >90% pure by $^1$H NMR and LCMS). HRMS (TOF ES) 375.1920 calcd for $C_{20}H_{26}N_2O_5$, m/z (M+H); observed 375.1910 (2.7 ppm error).

Synthesis of Carboxylic Acid (3):

Beads 2 (300 mg, 0.225 mmol) were swelled in THF (20 mL) for 15 min. Aqueous 1N-LiOH solution (1.125 mL, 1.125 mmol) was added to the $H_2O_2$ (30% aqueous, 2.3 mL, 22.5 mmol) in the 10 mL of polypropylene tube at room temperature and the resulting solution was vigorously stirred at room temperature for 30 min. The pre-made lithium hydroperoxide solution was added to the column containing the beads by syringe, and the polypropylene tube washed 2× with 2 mL THF and the washings added to the resin. (The final ratio of $THF/H_2O$ (7/1) and the final concentration of lithium hydroperoxide solution in the reaction vessel were essential to push the reactions to completion.) The reaction vessel was tumbled for 15 h. Resin was then isolated by filtration and washed as follows: 5×THF, 5× EtOH, 5×$H_2O$, 5×EtOH, 5×$H_2O$, EtOH×20 min, THF×20 min, $CH_2Cl_2$×20 min, 5×$CH_2Cl_2$. Solvent was then removed in vacuo to yield resin 3 (270.6 mg) as light yellow beads. The beads (10 mg) were subjected to the cleavage conditions, which yielded 1.5 mg of the crude product (>90% pure by $^1$H NMR). HRMS (TOF ES) 216.1236 calcd for $C_{10}H_{17}NO_4$, m/z (M+H); observed 216.1234.

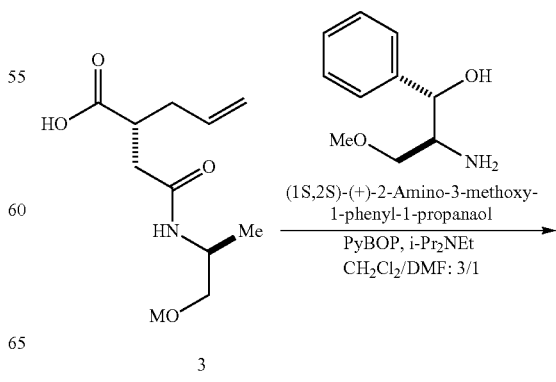

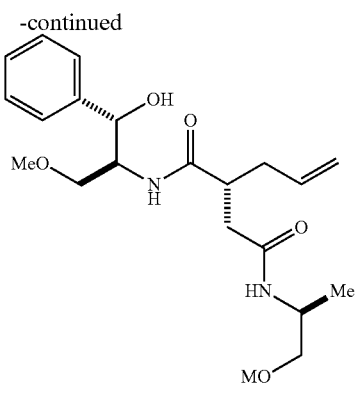

Synthesis of Amide (4):

Beads 3 (66.8 mg, 0.0435 mmol) were swelled in a mixed solvent of CH$_2$Cl$_2$ (1.3 mL) and DMF (0.43 mL) for 15 min. PyBOP (226 mg, 0.435 mmol), (1S,2S)-(+)-2-amino-3-methoxy-1-phenyl-1-propanaol (Aldrich, 78.9 mg, 0.435 mmol), and diisopropylethylamine (0.076 mL, 0.435 mmol) were added to the reaction column, which was shaken at room temperature for 14 h. Resin was then isolated by filtration and washed as follows: 5×CH$_2$Cl$_2$, 5×THF, 5×DMF, CH$_2$Cl$_2$×20 min, THF×20 min, DMF×20 min, THF×20 min, CH$_2$Cl$_2$×20 min, 5×CH$_2$Cl$_2$. Solvent was then removed in vacuo to yield resin 4 (77.7 mg) as light yellow beads. The beads (9.6 mg) were subjected to the cleavage conditions, which yielded 2.1 mg of the crude product (>90% pure by $^1$H NMR and LCMS). HRMS (TOF ES) 379.2233 calcd for C$_{20}$H$_{30}$N$_2$O$_5$, m/z (M+H); observed 379.2220.

Synthesis of Ester (5) Via 4.

Beads 4 (30 mg, 0.0195 mmol) were swelled in CH$_2$Cl$_2$ (1.2 mL) for 15 min. (R)-2-benzyl-5-pentenoic acid (CAS 93780-04-2) (37.2 mg, 0.195 mmol), diisopropycarbodiimide (0.031 mL, 0.195 mmol), and DMAP (2.37 mg, 0.195 mmol) were added to the reaction column, which was shaken at room temperature for 14 h. Resin was then isolated by filtration and washed as follows: 5×CH$_2$Cl$_2$, 5×THF, 5×DMF, CH$_2$Cl$_2$×20 min, THF×20 min, DMF×20 min, THF×20 min, CH$_2$Cl$_2$×20 min, 5×CH$_2$Cl$_2$. Solvent was then removed in vacuo to yield resin 5 (32.7 mg) as light yellow beads. The beads (10 mg) were subjected to the cleavage conditions, which yielded 2.0 mg of the crude product (>90% pure by $^1$H NMR and LCMS). HRMS (TOF ES) 551.3121 calcd for C$_{32}$H$_{42}$N$_2$O$_6$, m/z (M+H); observed 551.3107 (2.5 ppm error).

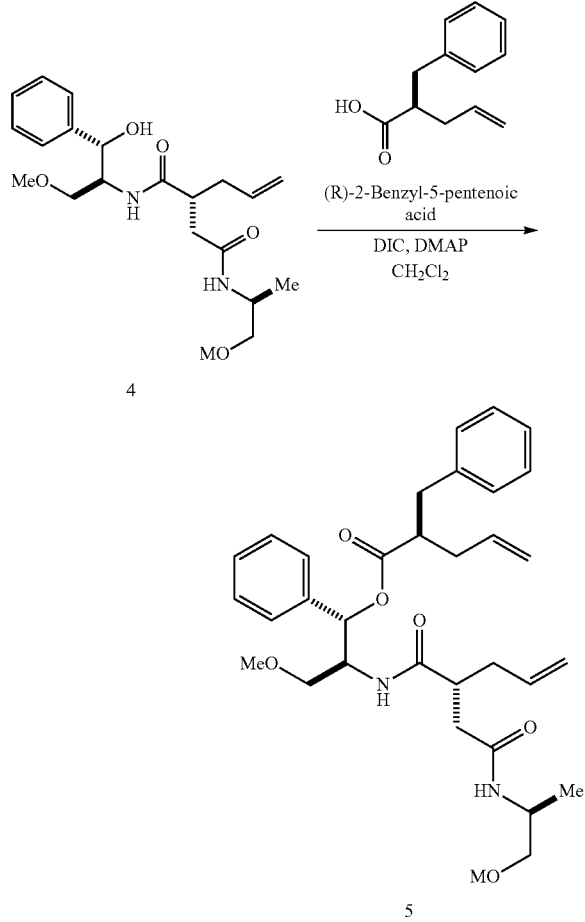

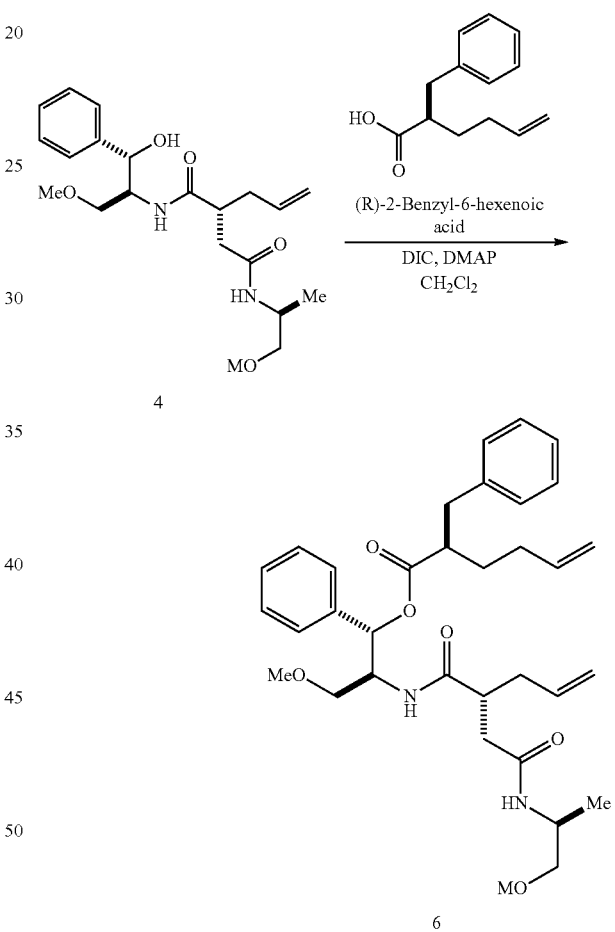

Synthesis of Ester (6) Via 4.

Beads 4 (30 mg, 0.0195 mmol) were swelled in CH$_2$Cl$_2$ (1.2 mL) for 15 min. (R)-2-Benzyl-6-hexenoic acid (39.8 mg, 0.195 mmol), diisopropycarbodiimide (0.031 mL, 0.195 mmol), and DMAP (2.37 mg, 0.195 mmol) were added to the reaction column, which was shaken at room temperature for 14 h. Resin was then isolated by filtration and washed as follows: 5×CH$_2$Cl$_2$, 5×THF, 5×DMF, CH$_2$Cl$_2$×20 min, THF×20 min, DMF×20 min, THF×20 min, CH$_2$Cl$_2$×20 min, 5×CH$_2$Cl$_2$. Solvent was then removed in vacuo to yield resin 6 (31.9 mg) as light yellow beads. The beads (10 mg) were subjected to the cleavage conditions, which yielded 1.9 mg of

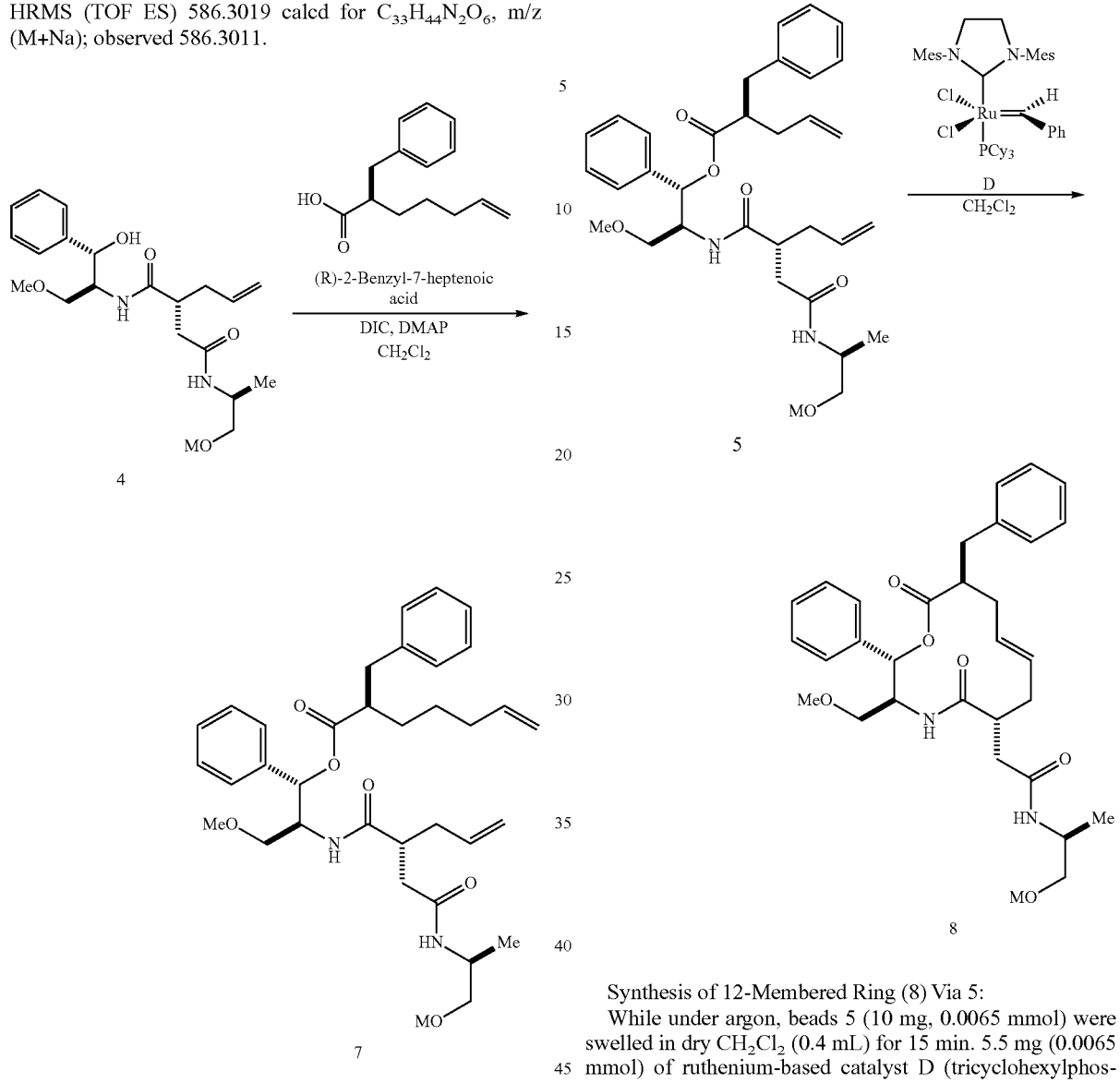

Synthesis of Ester (7) Via 4.

Beads 4 (30 mg, 0.0195 mmol) were swelled in $CH_2Cl_2$ (1.2 mL) for 15 min. (R)-2-Benzyl-7-heptenoic acid (42.6 mg, 0.195 mmol), diisopropycarbodiimide (0.031 mL, 0.195 mmol), and DMAP (2.37 mg, 0.195 mmol) were added to the reaction column, which was shaken at room temperature for 14 h. Resin was then isolated by filtration and washed as follows: 5×$CH_2Cl_2$, 5×THF, 5×DMF, $CH_2Cl_2$×20 min, THF× 20 min, DMF×20 min, THF×20 min, $CH_2Cl_2$×20 min, 5×$CH_2Cl_2$. Solvent was then removed in vacuo to yield resin 5 (33.4 mg) as light yellow beads. The beads (10 mg) were subjected to the cleavage conditions, which yielded 2.1 mg of the crude product (>90% pure by $^1H$ NMR and LCMS). HRMS (TOF ES) 579.3434 calcd for $C_{34}H_{46}N_2O_6$, m/z (M+Na); observed 579.3431.

the crude product (>90% pure by $^1H$ NMR and LCMS). HRMS (TOF ES) 586.3019 calcd for $C_{33}H_{44}N_2O_6$, m/z (M+Na); observed 586.3011.

Synthesis of 12-Membered Ring (8) Via 5:

While under argon, beads 5 (10 mg, 0.0065 mmol) were swelled in dry $CH_2Cl_2$ (0.4 mL) for 15 min. 5.5 mg (0.0065 mmol) of ruthenium-based catalyst D (tricyclohexylphosphine[1,3-bis(2,4,6-trimethylphenyl)-4,5-dihydroimidazol-2-ylidene][benzylidene]ruthenium(IV)dichloride) was weighted out into an oven-dried vial with a septum. Under argon, dry $CH_2Cl_2$ (1.0 mL) was added to the vial containing the catalyst by syringe and the vial was swirled lightly to dissolve the catalyst. 0.1 mL of the catalyst solution (0.00065 mmol, 10 mol % relative to bead-bound substrate) was immediately added to the reaction vial containing the pre-swelled beads by syringe under argon. Final concentration of the catalyst was 0.0013M in $CH_2Cl_2$. The reaction vial was heated in an oil bath at 45° C. for 24 h under a cloud of argon. (Final concentration of the catalyst was essential to push the reactions to completion.) The beads were then isolated by filtration and washed as follows: 5×$CH_2Cl_2$, 5×THF, 5×DMF, $CH_2Cl_2$×20 min. Metal contamination to the beads was dramatically reduced further by treating the beads with $P(CH_2OH)_3$ in $CH_2Cl_2/H_2O$ in accordance with the solution-phase purification procedure described by Maynard and Grubbs (Maynard, H. D.; Grubbs, R. H. Tetrahedron Lett. 1999, 40, 4137-4140). $P(CH_2OH)_3$ (8.1 mg, 0.065 mmol, 100 equivalents to the catalyst) was added to the column containing the beads in a mixed solvent of $CH_2Cl_2$ (0.5 mL) and $H_2O$ (0.5 mL) and then the reaction column was tumbled for 24 h. Resin was then isolated by filtration and washed as follows: 5×CH$_2$Cl$_2$, 5×H2O, 5×CH$_2$Cl$_2$, 5×H$_2$O, 5×THF, CH$_2$Cl$_2$×20 min, THF×20 min, CH$_2$Cl$_2$×20 min, THF×20 min, CH$_2$Cl$_2$×20 min, 5×CH$_2$Cl$_2$. Solvent was then removed in vacuo to yield resin 8 (9.6 mg) as light yellow beads. The beads were subjected to the cleavage conditions, which yielded 1.7 mg of the crude product (>90% pure by $^1$H NMR and LCMS). HRMS (TOF ES) 523.2808 calcd for C$_{30}$H$_{38}$N$_2$O$_6$, m/z (M+H); observed 523.2802 (1.1 ppm error).

as follows: 5×CH$_2$Cl$_2$, 5×THF, 5×DMF, CH$_2$Cl$_2$×20 min. P(CH$_2$OH)$_3$ (12.15 mg, 0.0975 mmol, 100 equivalents to the catalyst) was added to the column containing the beads in a mixed solvent of CH$_2$Cl$_2$ (0.5 mL) and H$_2$O (0.5 mL) and then the reaction column was tumbled for 24 h. Resin was then isolated by filtration and washed as follows: 5×CH$_2$Cl$_2$, 5×H$_2$O, 5×CH$_2$Cl$_2$, 5×H$_2$O, 5×THF, CH$_2$Cl$_2$×20 min, THF×20 min, CH$_2$Cl$_2$×20 min, THF×20 min, CH$_2$Cl$_2$×20 min, 5×CH$_2$Cl$_2$. Solvent was then removed in vacuo to yield resin 9 (9.8 mg) as light yellow beads. The beads were subjected to the cleavage conditions, which yielded 2.0 mg of the crude product (>85% pure by $^1$H NMR and LCMS). HRMS (TOF ES) 537.2964 calcd for C$_{31}$H$_{40}$N$_2$O$_6$, m/z (M+H); observed 537.2961.

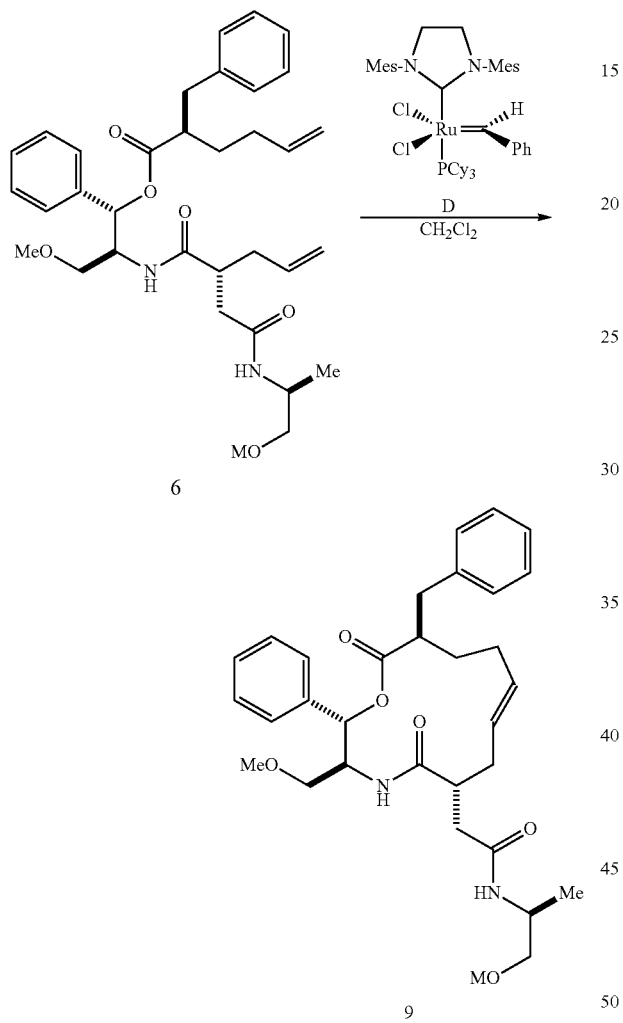

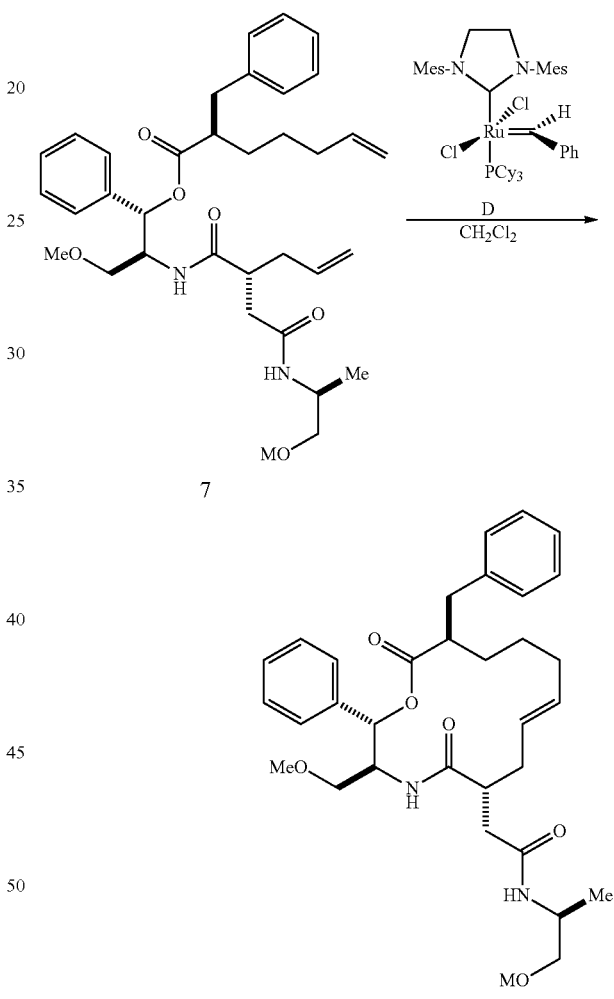

Synthesis of 13-Membered Ring (9) Via 6:

While under argon, beads 6 (10 mg, 0.0065 mmol) were swelled in dry CH$_2$Cl$_2$ (0.4 mL) for 15 min. 8.25 mg (0.00975 mmol) of ruthenium-based catalyst D (tricyclohexylphosphine[1,3-bis(2,4,6-trimethylphenyl)-4,5-dihydroimidazol-2-ylidene][benzylidene]ruthenium(IV)dichloride) was weighted out into an oven-dried vial with a septum. Under argon, dry CH$_2$Cl$_2$ (1.0 mL) was added to the vial containing the catalyst by syringe and the vial was swirled lightly to dissolve the catalyst. 0.1 mL of the catalyst solution (0.000975 mmol, 15 mol % relative to bead-bound substrate) was immediately added to the reaction vial containing the pre-swelled beads by syringe under argon. The reaction vial was heated in an oil bath at 45° C. for 24 h under a cloud of argon. The beads were then isolated by filtration and washed Synthesis of 14-Membered Ring (10) Via 7:

While under argon, beads 7 (10 mg, 0.0065 mmol) were swelled in dry CH$_2$Cl$_2$ (0.4 mL) for 15 min. 16.5 mg (0.0195 mmol) of ruthenium-based catalyst D (tricyclohexylphosphine[1,3-bis(2,4,6-trimethylphenyl)-4,5-dihydroimidazol-2-ylidene][benzylidene]ruthenium(IV)dichloride) was weighted out into an oven-dried vial with a septum. Under argon, dry CH$_2$Cl$_2$ (1.0 mL) was added to the vial containing the catalyst by syringe and the vial was swirled lightly to dissolve the catalyst. 0.1 mL of the catalyst solution (0.00195 mmol, 30 mol % relative to bead-bound substrate) was immediately added to the reaction vial containing the pre-swelled beads by syringe under argon. The reaction vial was heated in an oil bath at 45° C. for 24 h under a cloud of argon. The beads were then isolated by filtration and washed as follows: 5×CH$_2$Cl$_2$, 5×THF, 5×DMF, CH$_2$Cl$_2$×20 min. P(CH$_2$OH)$_3$ (24.3 mg, 0.195 mmol, 100 equivalents to the catalyst) was added to the column containing the beads in a mixed solvent of CH$_2$Cl$_2$ (0.5 mL) and H$_2$O (0.5 mL) and then the reaction column was tumbled for 24 h. Resin was then isolated by filtration and washed as follows: 5×CH$_2$Cl$_2$, 5×H$_2$O, 5×CH$_2$Cl$_2$, 5×H$_2$O, 5×THF, CH$_2$Cl$_2$×20 min, THF×20 min, CH$_2$Cl$_2$×20 min, THF×20 min, CH$_2$Cl$_2$×20 min, 5×CH$_2$Cl$_2$. Solvent was then removed in vacuo to yield resin 10 (9.7 mg) as light brown beads. The beads were subjected to the cleavage conditions, which yielded 2.4 mg of the crude product (>90% pure by $^1$H NMR and LCMS). HRMS (TOF ES) 551.3121 calcd for C$_{32}$H$_{42}$N$_2$O$_6$, m/z (M+H); observed 551.3124.

Using the reaction schemes set forth above and in the other Examples, the following building blocks were used in all combinations to generate a library of compounds of formula I:

Set 1

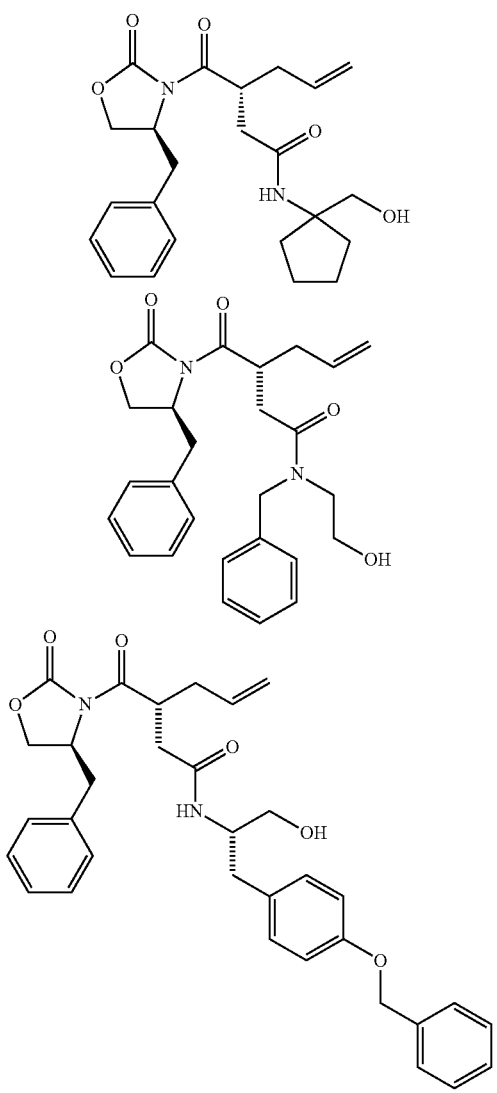

Set 2

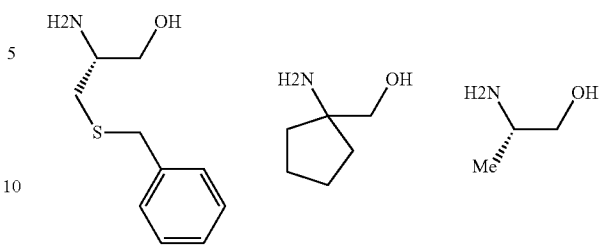

Set 3

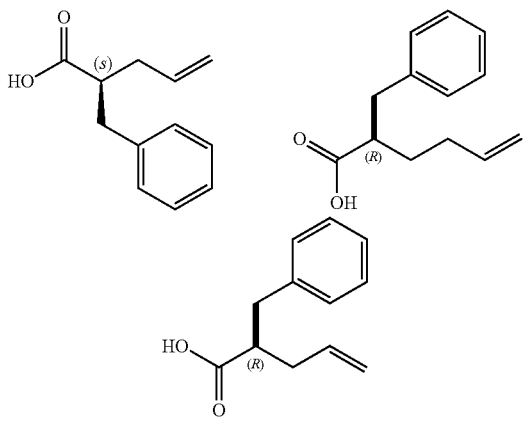

Example 4

Solution Phase Synthesis of Certain Compounds of Formula I

Materials

Commercially available reagents were obtained from Aldrich Chemical Co. (Milwaukee, Wis.), Fluka Chemical Corp. (Milwaukee, Wis.), TCI America (Portland, Oreg.), and Toronto Research Chemicals Inc. (ON, Canada) and used as received unless otherwise noted. All solvents for reactions, were dispensed from a solvent purification system that passes solvents through packed columns (THF, CH$_3$CN, and CH$_2$Cl$_2$: dry neutral alumina; DMF: activated molecular sieves). Water was double distilled. Reactions were monitored by analytical thin-layer chromatography using Merck silica gel 60 F254 plates. Compounds were visualized with a UV lamp (λ 254) and staining with I$_2$/SiO$_2$.

Purification and Analysis

Flash chromatography was performed using a CombiFlash Companion system (Teledyne, ISCO, Inc.) with prepacked FLASH silica columns (Biotage, Inc.). $^1$H NMR spectra were recorded at 23° C. on a Varian Mercury400 (400 MHz), and Varian Unity/Inova500 (500 MHz) Chemical shifts (δ) are reported in parts per million (ppm) downfield from tetramethylsilane and referenced to residual protium in the NMR solvent (CDCl$_3$, δ=7.26). Data are reported as follows: chemical shift, multiplicity (s=singlet, d=doublet, t=triplet, m=multiplet), coupling constant (J) in Hertz (Hz), and integration. $^{13}$C NMR spectra were recorded at 23° C. on a Varian Mercury400 (400 MHz) and a Varian Unity/Inova500 (500 MHz) spectrometer. Chemical shifts (δ) are reported in parts per million (ppm) downfield from tetramethylsilane and referenced to carbon resonances in the NMR solvent (CDCl3, δ=77.23, center line). High-resolution mass spectra (HRMS) were obtained at the mass spectrometry facility at Harvard University using a mass resolution of 10.000.
Synthesis of Robotnikinin
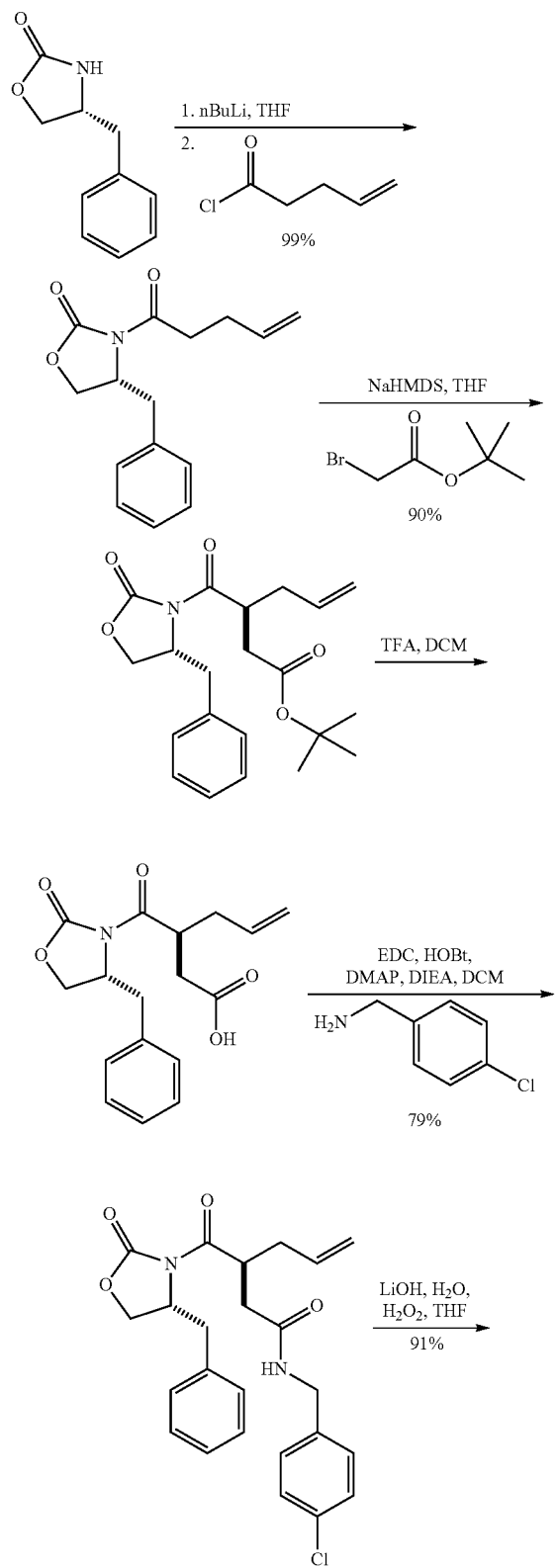
-continued
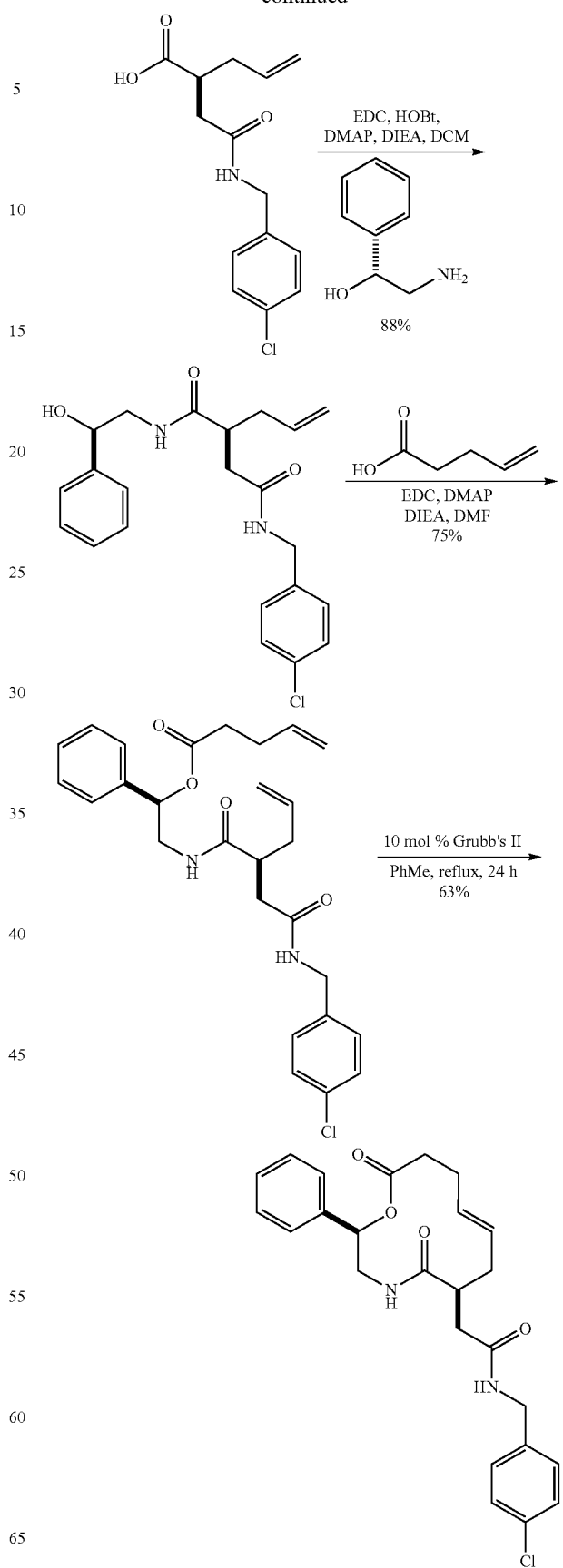

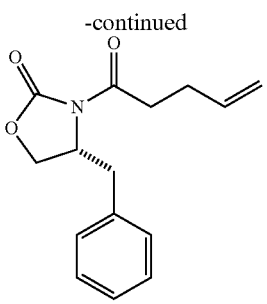

(R)-4-benzyl-3-pent-4-enoyloxazolidin-2-one (1a)

A solution of (R)-4-benzyl-2-oxazolidinone (2 g, 0.011 mmol) in dry THF (33 mL) was cooled to −78° C. To this solution n-butyllithium (1.6 M in hexanes, 6.87 mL, 0.011 mmol) was added over a ten-minute period. Following this addition, 4-pentenoyl chloride (1.32 mL, 0.012 mmol) was added in a single portion. The reaction mixture was stirred under argon at −78° C. for 30 minutes and then warmed to room temperature. The reaction progress was monitored by TLC (~1 h). The reaction mixture was quenched with saturated aqueous ammonium chloride (60 mL) and the product was extracted with dichloromethane (2×80 mL). The combined organic layers were washed successively with 1 N sodium hydroxide and brine, dried over $Na_2SO_4$, and filtered. The solution was concentrated in vacuo and the residue was cooled at 4° C. overnight. The resulting solid was triturated using cold hexanes and dried to give a white solid, 1a (2.838 g, 99%). $^1$H NMR (CDCl$_3$, 500 MHz): δ 7.33-7.37 (m, 1H), 7.28-7.32 (m, 1H), 7.20-7.24 (m, 1H), 5.84-5.96 (m, 1H), 5.13 (dd, J=17.1, 1.5 Hz, 1H), 5.05 (dd, J=10.3, 1.0 Hz, 1H), 4.69 (ddd, 1H), 4.15-4.25 (m, 1H), 3.31 (dd, J=13.2, 3.4 Hz, 1H), 2.99-3.16 (m, 1H), 2.77 (dd, J=13.2, 9.8 Hz, 1H), 2.44-2.51 ppm (m, 1H). $^{13}$C NMR (126 MHz, CDCl$_3$): δ 172.8, 136.9, 135.5, 129.6, 129.2, 127.6, 116.0, 110.0, 66.4, 55.4, 38.2, 35.0, 28.4. HRMS calcd for $C_{15}H_{17}NO_3$ (M+H) m/z 260.1286, found 260.1277.

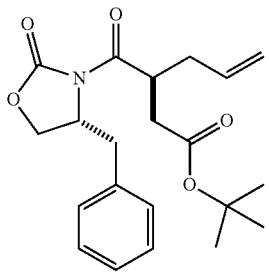 [SMILES: C=CC[C@@H](CC(=O)OC(C)(C)C)C(=O)N1C(=O)OC[C@H]1Cc1ccccc1]

(S)-tert-butyl 3-((R)-4-benzyl-2-oxooxazolidine-3-carbonyl)hex-5-enoate (2a)

A dry round bottom flask was charged with 1a (3.2 g, 12.34 mmol) and dry THF (123 mL) and then cooled to −78° C. To this solution NaHMDS (1M in THF, 13.57 mL, 13.57 mmol) was added over a period of 10 minutes. To ensure complete enolization, the reaction mixture was stirred for an additional 20 minutes at −78° C. A solution of tert-butyl bromoacetate (2.74 mL, 18.51 mmol) in THF (6 mL) was then introduced to the reaction flask. The solution was stirred for 1 hour at −78° C. and then warmed to −48° C. while still stirring. The reaction was monitored by TLC (~3 h) and quenched with saturated aqueous NH$_4$Cl. The reaction mixture was concentrated by the removing the THF under reduced pressure. The residue was then diluted with dichloromethane. This solution was washed successively with water and brine, dried over $Na_2SO_4$, and concentrated under reduced pressure to give white crystals of 2a (4.27 g, 93%). $^1$H NMR (500 MHz, CDCl$_3$): δ ppm 7.32-7.37 (m, 2H) 7.27-7.30 (m, 3H) 5.74-5.85 (m, 1H) 5.05-5.13 (m, 2H) 4.63-4.70 (m, 1H) 4.25-4.32 (m, 1H) 4.16 (d, J=4.9 Hz, 2H) 3.34 (dd, J=13.4, 2.7 Hz, 1H) 2.74-2.87 (m, 2H) 2.39-2.52 (m, 2H) 2.19-2.26 (m, 1H) 1.44 (s, 9H); $^{13}$C NMR (126 MHz, CDCl$_3$): δ 175.0, 171.1, 153.0, 135.6, 134.4, 129.4, 128.8, 127.1, 117.7, 80.6, 65.8, 55.4, 39.0, 37.5, 36.6, 36.1, 28.0. HRMS calcd for $C_{21}H_{27}NO_5$ (M+H) m/z 374.1967, found 374.1971.

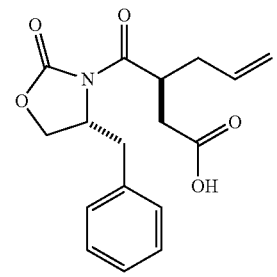 [SMILES: C=CC[C@@H](CC(=O)O)C(=O)N1C(=O)OC[C@H]1Cc1ccccc1]

(S)-3-((R)-4-benzyl-2-oxooxazolidine-3-carbonyl)hex-5-enoic acid (3a)

A round bottom flask was charged with a solution of compound 2 (4.27 g, 11.44 mmol) in dichloromethane (9 mL). TFA (9 mL, 51.42 mmol) was added to this solution at room temperature in one portion. The reaction progress was monitored by TLC (~1 h). The dichloromethane and excess TFA were removed under reduced pressure. To ensure the removal of all remaining TFA, the residue was azeotroped with benzene 3 times to yield a colorless oil 3a. The reaction succeeding was taken on crude. $^1$H NMR (500 MHz, CDCl$_3$): δ ppm 11.19 (br. s, 1H) 7.31-7.37 (m, 2H) 7.27-7.31 (m, 1H) 7.22-7.26 (m, 2H) 5.71-5.82 (m, 1H) 5.07-5.14 (m, 2H) 4.25-4.33 (m, 1H) 4.17 (d, J=4.9 Hz, 2H) 3.25 (dd, J=13.7, 3.4 Hz, 1H) 2.96 (dd, J=17.6, 10.7 Hz, 1H) 2.78 (dd, J=13.7, 9.3 Hz, 1H) 2.59 (dd, J=17.6, 3.9 Hz, 1H) 2.39-2.47 (m, 1H) 2.18-2.26 (m, 1H); $^{13}$C NMR (126 MHz, CDCl$_3$): δ 178.2, 174.6, 153.0, 135.2, 133.9, 129.4, 128.8, 127.1, 118.12, 65.9, 55.3, 38.6, 37.2, 36.0, 34.86. HRMS calcd for $C_{17}H_{19}NO_5$ (M+H) m/z 318.1341, found 318.1339.

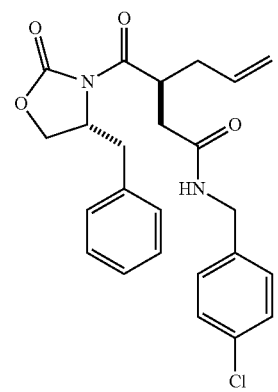 [SMILES: C=CC[C@@H](CC(=O)NCc1ccc(Cl)cc1)C(=O)N1C(=O)OC[C@H]1Cc1ccccc1]

(S)-3-((R)-4-benzyl-2-oxooxazolidine-3-carbonyl)-N-(4-chlorobenzyl)hex-5-enamide (4a)

A solution of compound 3a (0.402 g, 1.3 mmol), EDC (0.364 g, 1.9 mmol), HOBT (0.256 g, 1.9 mmol), and Hunig's base (0.662 mL, 3.8 mmol) in dichloromethane (17 mL) was cooled to 0° C. and stirred for half an hour. To this solution 4-chlorobenzylamine (0.174 mL, 1.43 mmol) and a catalytic amount of DMAP were added. The reaction was stirred overnight and the reaction progress was monitored by TLC. The dichloromethane was removed in vacuo and the reaction mixture quenched with aqueous $NH_4Cl$. The solution was washed with water and brine, dried over $Na_2SO_4$, and concentrated under reduced pressure to give well formed white crystals of 4a (0.443 g, 79%). $^1$H NMR (500 MHz, $CDCl_3$): δ ppm 7.31-7.36 (m, 2H) 7.21-7.29 (m, 5H) 7.17-7.21 (m, 2H) 6.09 (t, J=5.6 Hz, 1H) 5.73-5.82 (m, 1H) 5.04-5.10 (m, 2H) 4.65 (ddd, J=13.3, 6.7, 3.4 Hz 1H) 4.41 (dd, J=15.2, 5.9 Hz, 1H) 4.34 (dd, J=14.9, 5.9 Hz, 1H) 4.23-4.30 (m, 1H) 4.23-4.30 (m, 1H) 4.14-4.18 (m, 2H) 3.28 (dd, J=13.7, 2.9 Hz, 1H) 2.66-2.80 (m, 2H) 2.41-2.51 (m, 2H) 2.22-2.29 (m, 1H); $^{13}$C NMR (126 MHz, $CDCl_3$): δ 175.1, 171.0, 153.4, 137.1, 135.7, 134.8, 133.4, 129.7, 129.3, 129.1, 129.0, 127.5, 118.1, 66.3, 55.7, 43.1, 40.1, 38.0, 37.8, 36.3. HRMS calcd. for $C_{24}H_{25}ClN_2O_4$ (M+H) m/z 441.1581, found 441.1581.

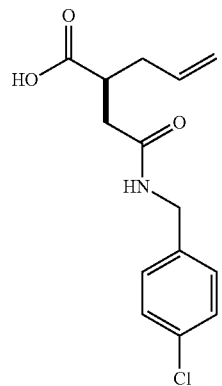 [SMILES: C=CC[C@@H](CC(=O)NCc1ccc(Cl)cc1)C(=O)O]

(S)-2-(2-(4-chlorobenzylamino)-2-oxoethyl)pent-4-enoic acid (5a)

A round bottom flask was charged with a solution of 4 (0.443 g, 1 mmol) in $THF/H_2O$ (4:1, 10 mL) and cooled to 0° C. To this solution $H_2O_2$ (0.45 mL, 4 mmol) was added, followed by aqueous LiOH (0.05 g, 2 mmol/2.5 mL $H_2O$). The reaction mixture was stirred for 1 hour, followed by an addition of saturated aqueous $Na_2SO_3$ (4 mL). The reaction mixture was then stirred for an additional 20 minutes. The THF was removed under reduced pressure and the remaining residue was diluted with dichloromethane and water. The organic layer was set aside to recover the hydrolyzed chiral auxiliary within. The aqueous layer was acidified with 3 M aqueous HCl followed by extraction with dichloromethane (3×60 mL). The combined organic layers were washed with water and brine, dried over $Na_2SO_4$, and concentrated to give 5a (0.26 g, 91%). HRMS calcd for $C_{14}H_{16}ClNO_3$ (M+H) m/z 282.0897, found 282.0897.

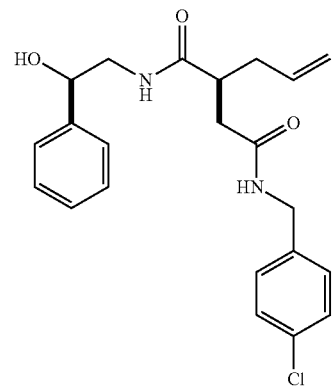 [SMILES: C=CC[C@@H](CC(=O)NCc1ccc(Cl)cc1)C(=O)NC[C@H](O)c1ccccc1]

(S)-2-allyl-N4-(4-chlorobenzyl)-N-1-((R)-2-hydroxy-2-phenylethyl)succinamide (8a)

A solution of 5a (0.375 g, 1.33 mmol), EDC (0.382 g, 1.995 mmol), HOBT (0.27 g, 1.995 mmol), and Hunig's base (0.695 mL, 3.99 mmol) in DMF (8.87 mL) was cooled to 0° C. and stirred for 30 min. To this solution, (R)-2-amino-1-phenylethanol (0.200 g, 1.46 mmol) and catalytic amount of DMAP were added. Subsequently, the cooling bath was removed, and the reaction mixture was allowed to warm to room temperature overnight. The DMF was removed under reduced pressure. The residue was then quenched with aqueous $NH_4Cl$, diluted with ethyl acetate, and washed successively with water and brine. This solution was dried over $Na_2SO_4$, filtered, and concentrated to afford 8a (0.384 g, 72%). HRMS calcd. for $C_{22}H_{25}ClN_2O_3$ (M+H) m/z 401.1632, found 401.1651.

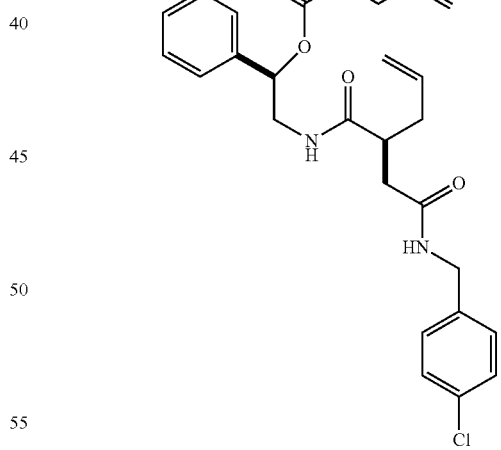

(R)-2-((S)-2-(2-(4-chlorobenzylamino)-2-oxoethyl) pent-4-enamido)-1-phenylethyl pent-4-enoate (15a)

A flask was charged with a solution of 8a (0.128 g, 0.319 mmol), EDC (0.092 g, 0.479 mmol), Hunig's base (0.124 g, 0.957 mmol) in DMF (5 mL) and stirred for half an hour. To the reaction mixture, 4-pentenoic acid (0.035 g, 0.351 mmol) and catalytic amount of DMAP were added and allowed to stir overnight. The reaction progress was monitored by LCMS. The reaction mixture was quenched with aqueous NH₄Cl and then washed with water and brine. The solution was dried over Na₂SO₄, filtered, and concentrated under reduced pressure. The residue was purified by silica gel chromatography and concentrated to afford 15a (0.115 g, 75%). ¹H NMR (400 MHz, CDCl₃): asterisks denote rotamers δ ppm 7.23-7.37 (m, 7H) 7.14-7.18 (m, 2H) 6.71 (t, J=5.9 Hz, 1H), 6.54* (t, J=5.9 Hz, 1H) 6.41 (t, J=5.8 Hz, 1H) 6.17* (t, J=5.8 Hz, 1H) 5.58-5.84 (m, 3H) 4.96-5.09 (m, 4H) 4.36 (dd, J=11.3, 6.2 Hz, 1H) 4.22-4.30 (m, 1H) 3.55-3.64 (m, 1H) 3.46-3.53 (m, 1H) 2.70-2.84 (m, 1H) 2.44-2.53 (m, 3H) 2.27-2.40 (m, 4H) 2.10-2.21 (m, 1H); ¹³C NMR (101 MHz, CDCl₃): δ=174.4, 174.1,* 172.2, 172.2,* 171.5, 171.3,* 137.6, 137.5,* 136.9, 136.8,* 136.49, 136.48,* 135.0, 134.9,* 133.1, 133.0,* 128.9, 128.7,* 128.62, 128.61,* 128.45, 128.38,* 126.4, 126.3,* 117.63, 117.55,* 115.61, 115.59,* 74.2, 44.2, 44.1,* 42.8, 42.7,* 42.6, 38.2, 38.1,* 36.6, 36.5,* 33.5, 28.7 ppm. HRMS calcd. for $C_{27}H_{31}ClN_2O_4$ (M+H) m/z 483.2050, found 483.2052.

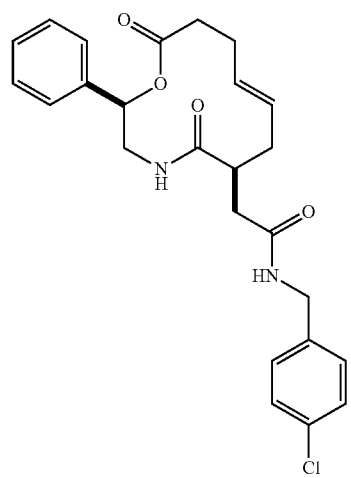

N-(4-chlorobenzyl)-2-((2R,6S,E)-5,12-dioxo-2-phenyl-1-oxa-4-azacyclododec-8-en-6-yl)acetamide (24a)

To a solution of 15a (0.057 g, 0.119 mmol) in toluene (11 mL) was added Grubbs II catalyst (0.011 g, 0.0129 mmol). The reaction mixture was heated to 65° C. and stirred overnight. The reaction progress was monitored by TLC. The reaction mixture was allowed to cool, diluted with dichloromethane to make a 0.1 M solution, and stirred with Pb(OAc)₄ (0.029 g, 0.065 mmol) overnight. The Pb(OAc)₄ was removed by directly subjecting the mixture to silica gel chromatography to afford 24a (0.034 g, 63%). ¹H NMR (500 MHz, DMSO-d₆): asterisks denote rotamers and E/Z isomers δ ppm 8.54 (t, J=5.9 Hz, 1H) 8.41* (t, J=5.9 Hz, 1H) 7.94 (d, J=9.8 Hz, 1H) 7.31-7.42 (m, 7H) 7.21-7.28 (m, 2H) 5.83-5.91 (m, 1H) 5.37-5.42 (m, 1H) 5.25-5.37 (m, 1H) 4.18-4.27 (m, 2H) 4.00-4.12 (m, 1H) 2.76 (d, J=14.2 Hz, 1H) 2.58-2.66 (m, 1H) 2.32-2.44 (m, 2H) 2.12-2.32 (m, 4H) 1.97-2.11 (m, 2H); ¹³C NMR (DMSO-d₆, 126 MHz): δ=174.8, 172.8, 172.3,* 171.7,* 170.43, 170.35,* 138.8, 138.7,* 138.2, 138.1,* 131.2, 130.2,* 129.7, 128.9, 128.9, 128.7, 128.2, 128.1, 126.23, 126.20,* 73.3, 43.1, 42.7, 41.3, 38.3, 35.7, 34.4, 29.2 ppm. HRMS calcd. for $C_{25}H_{27}ClN_2O_4$ (M+H) m/z 455.1737, found 455.1741.

Synthesis of Additional Analogs

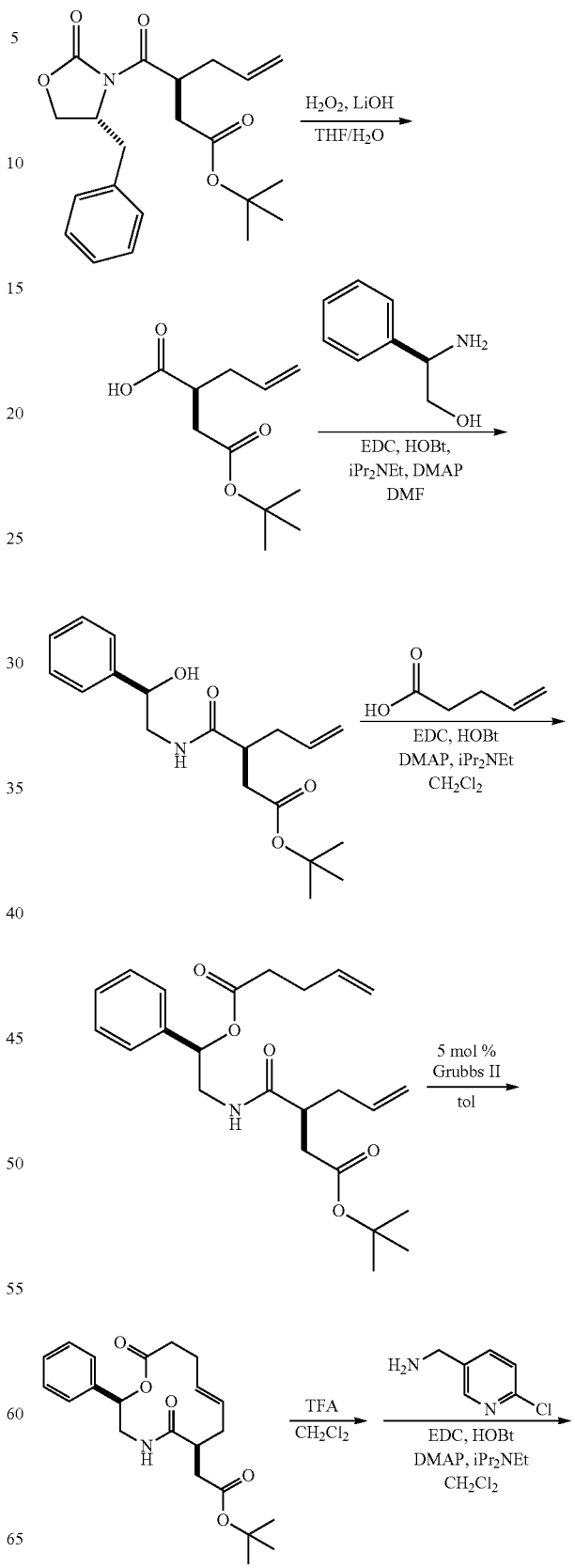

-continued

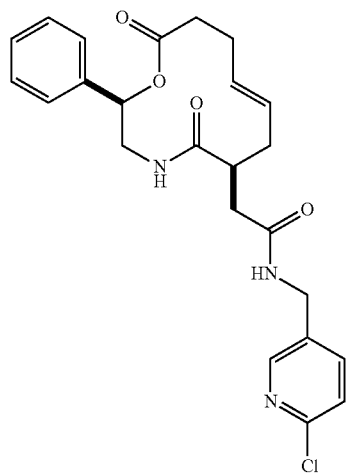

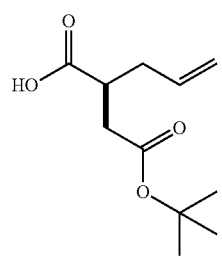

S)-2-(2-tert-butoxy-2-oxoethyl)pent-4-enoic acid

To a solution of (S)-tert-butyl 3-((R)-4-benzyl-2-oxoox-azolidine-3-carbonyl)hex-5-enoate (22.0 g, 58.9 mmol) in THF (491 mL) and water (123 mL) cooled in an ice/water bath was added $H_2O_2$ (24.3 mL, 236 mmol) followed by dropwise addition of a solution of LiOH (2.82 g, 118 mmol) in water (123 mL). The reaction mixture was stirred 1 h at which point TLC analysis indicated complete consumption of starting material. The reaction mixture was diluted with 250 mL sat. $Na_2SO_3$ and stirred 1 h. The THF was subsequently removed by rotary evaporation and the remaining aqueous fraction was extracted 3× with $CH_2Cl_2$. The aqueous layer was acidified with 2 N HCl and extracted 3× with $CH_2Cl_2$. The combined organic extracts were washed with brine, dried over $Na_2SO_4$, filtered, and concentrated to yield 7.7 g of product as a light yellow oil in 61% yield. LRMS $(M+HCO_2H)^-$: 259.5.

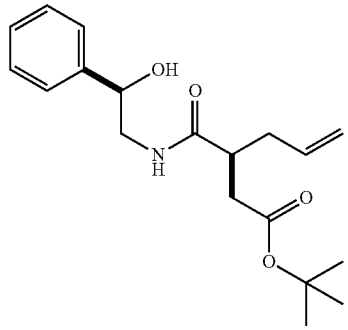

(S)-tert-butyl 3-((R)-2-hydroxy-2-phenylethylcarbamoyl)hex-5-enoate

To a solution of (S)-2-(2-tert-butoxy-2-oxoethyl)pent-4-enoic acid (0.947 g, 4.42 mmol) (described by Stanton, B. Z. et al. *Nat. Chem. Biol.* 2009, 5, 154-156) in DMF (31.6 mL) cooled in an ice/water bath was added EDC (1.27 g, 6.63 mmol) and HOBt (0.896 g, 6.63 mmol) and the resulting solution was stirred 30 min. (R)-2-amino-phenylethanol (0.667 g, 4.86 mmol), $iPr_2NEt$ (2.31 mL, 13.3 mmol) and DMAP (0.108 g, 0.884 mmol) were subsequently added and the reaction mixture was slowly warmed to rt and stirred for 16 h at which point LC-MS analysis indicated complete consumption of starting material. The reaction mixture was diluted with saturated $NH_4Cl$ and EtOAc and the layers separated. The aqueous was extracted 2× with EtOAc and the combined organic extracts were washed with 1 N HCl and brine, dried over $Na_2SO_4$, filtered, and concentrated. The crude product was purified using silica gel chromatography (MeOH/$CH_2Cl_2$ gradient) to yield 1.25 g of desired product as a light yellow oil in 85% yield. LRMS $(M+Na)^+$: 356.2.

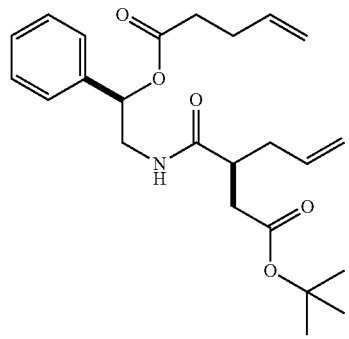

(S)-tert-butyl 3-((R)-2-(pent-4-enoyloxy)-2-phenylethylcarbamoyl)hex-5-enoate

To a solution of 4-pentenoic acid (0.335 mL, 3.28 mmol) in DMF (31.6 mL) cooled in an ice/water bath was added EDC (630 mg, 3.28 mmol) and the resulting solution was stirred 30 min. (S)-tert-butyl 3-((R)-2-hydroxy-2-phenylethylcarbamoyl)hex-5-enoate (730 mg, 2.19 mmol), $iPr_2NEt$ (1.14 mL, 6.57 mmol) and DMAP (26.7 mg, 0.219 mmol) were subsequently added and the reaction mixture was slowly warmed to rt and stirred for 16 h at which point LC-MS analysis indicated complete consumption of starting material. The reaction mixture was diluted with saturated $NH_4Cl$ and EtOAc and the layers separated. The aqueous was extracted 2× with EtOAc and the combined organic extracts were washed with 1N HCl and brine, dried over $Na_2SO_4$, filtered, and concentrated. The crude product was purified using silica gel chromatography (MeOH/$CH_2Cl_2$ gradient) to yield 670 mg of desired product as a colorless oil in 74% yield. LRMS $(M+Na)^+$: 430.0.

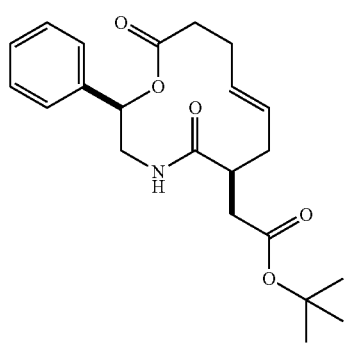

tert-butyl 2-((2R,6S,E)-5,12-dioxo-2-phenyl-1-oxa-4-azacyclododec-8-en-6-yl)acetate To a solution of (S)-tert-butyl 3-((R)-2-(pent-4-enoyloxy)-2-phenylethylcarbamoyl)hex-5-enoate (470 mg, 1.13 mmol) in toluene (113 mL) was added Grubbs 2nd Generation catalyst (96 mg, 0.113 mmol) and the reaction mixture was heated to 65° C. Upon stirring 7 h with continued heating, TLC analysis indicated complete consumption of starting material. The reaction mixture was cooled to rt, diluted with degassed $CH_2Cl_2$ (11 ml) and $Pb(OAc)_4$ (251 mg, 0.566 mmol) was added. The resulting mixture was stirred for 12 h at which point the mixture was passed through a short plug of silica then concentrated using rotary evaporation. The resulting purple solid was triturated with methanol to further remove ruthenium complexes. The off white solid that remained was purified using silica gel chromatography (MeOH/$CH_2Cl_2$ gradient) to yield 320 mg of desired product as a white solid in 73% yield. LRMS (M+Na)$^+$: 410.4.

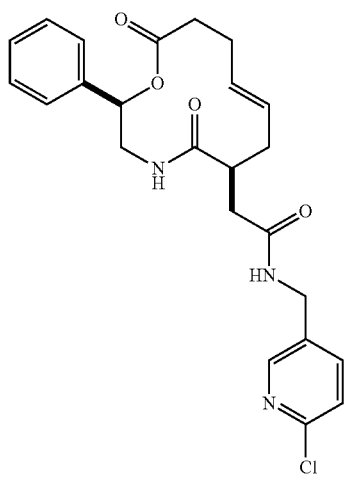

N-((6-chloropyridin-3-yl)methyl)-2-((2R,6S,E)-5,12-dioxo-2-phenyl-1-oxa-4-azacyclododec-8-en-6-yl)acetamide To a solution of tert-butyl 2R,6S,E)-5,12-dioxo-2-phenyl-1-oxa-4-azacyclododec-8-en-6-yl)acetate (200 mg, 0.516 mmol) in $CH_2Cl_2$ (397 mL) cooled in an ice/water bath was added trifluoroacetic acid (179 µL, 2.32 mmol) and the reaction mixture was stirred 1 h at which point LC-MS analysis indicated complete consumption of starting material. The reaction mixture was concentrated and a portion of the crude carboxylic acid was utilized immediately. To a solution of crude 2-((2R,6S,E)-5,12-dioxo-2-phenyl-1-oxa-4-azacyclododec-8-en-6-yl)acetic acid (86 mg, 0.260 mmol) in $CH_2Cl_2$ (3.2 mL) cooled in an ice/water bath was added EDC (74.6 mg, 0.389 mmol) and HOBt (52.6 mg, 0.389 mmol) and the resulting solution was stirred 30 min 2-chloro-5-aminomethylpyridine (40.7 mg, 0.285 mmol), iPr$_2$NEt (139 µL, 0.779 mmol) and DMAP (3.2 mg, 0.026 mmol) were subsequently added and the reaction mixture was slowly warmed to rt and stirred for 16 h at which point LC-MS analysis indicated complete consumption of starting material. The reaction mixture was diluted with saturated NH$_4$Cl and EtOAc and the layers separated. The aqueous was extracted 2× with EtOAc and the combined organic extracts were washed with 1 N HCl and brine, dried over Na$_2$SO$_4$, filtered, and concentrated. The crude product was purified using silica gel chromatography (MeOH/$CH_2Cl_2$ gradient) to yield the desired product as a colorless oil. LRMS (M+H)$^+$: 456.1.

Using the procedure described above, similar analogs were prepared by varying the amine reagent in the final step:

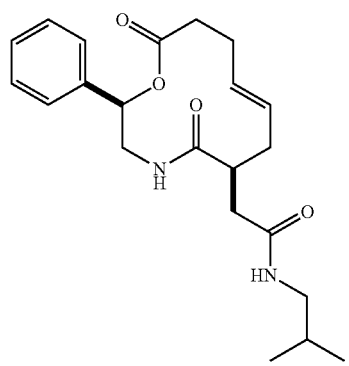

2-((2R,6S,E)-5,12-dioxo-2-phenyl-1-oxa-4-azacyclododec-8-en-6-yl)-N-isobutylacetamide

LRMS (M+H)$^+$: 387.1.

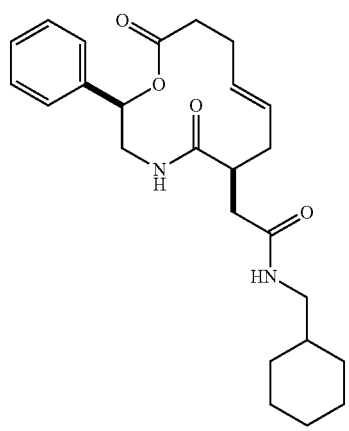

105

N-(cyclohexylmethyl)-2-((2R,6S,E)-5,12-dioxo-2-phenyl-1-oxa-4-azacyclododec-8-en-6-yl)acetamide

LRMS (M+H)+: 427.4.

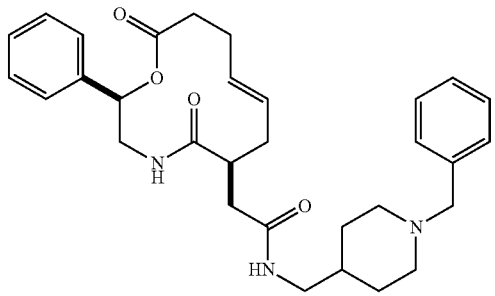

N-((1-benzylpiperidin-4-yl)methyl)-2-((2R,6S,E)-5,12-dioxo-2-phenyl-1-oxa-4-azacyclododec-8-en-6-yl)acetamide

LRMS (M+H)+: 518.5.

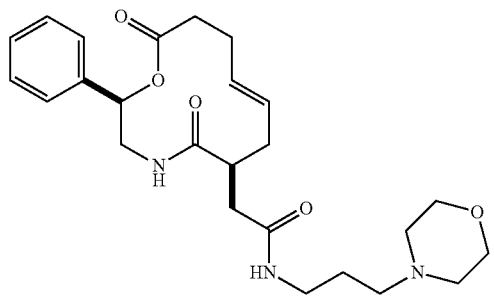

2-((2R,6S,E)-5,12-dioxo-2-phenyl-1-oxa-4-azacyclododec-8-en-6-yl)-N-(3-morpholinopropyl)acetamide

LRMS (M+H)+: 458.4.

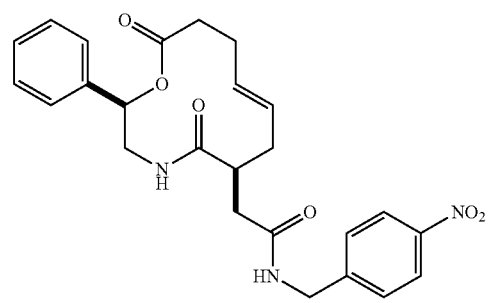

106

2-((2R,6S,E)-5,12-dioxo-2-phenyl-1-oxa-4-azacyclododec-8-en-6-yl)-N-(4-nitrobenzyl)acetamide

LRMS (M+H)+: 466.3.

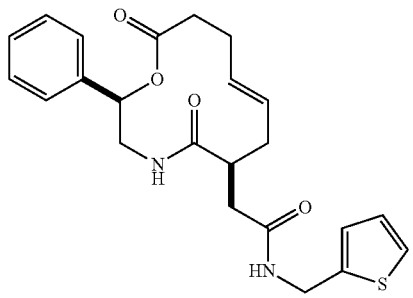

2-((2R,6S,E)-5,12-dioxo-2-phenyl-1-oxa-4-azacyclododec-8-en-6-yl)-N-(thiophen-2-ylmethyl)acetamide

LRMS (M+H)+: 427.2.

Synthesis of Methyl Amide Analog

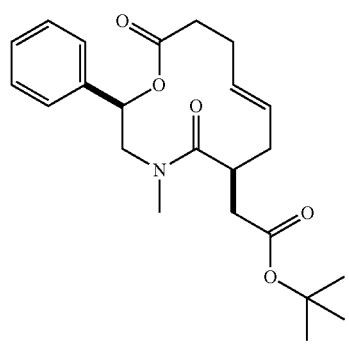

tert-butyl 2-((2R,6S,E)-4-methyl-5,12-dioxo-2-phenyl-1-oxa-4-azacyclododec-8-en-6-yl)acetate To a solution of tert-butyl 2-(2R,6S,E)-5,12-dioxo-2-phenyl-1-oxa-4-azacyclododec-8-en-6-yl)acetate (200 mg, 0.516 mmol) (see above) and iodomethane (96 µL, 1.55 mmol) in DMF (2.58 mL) cooled in an ice/water bath was added sodium hydride (20.6 mg, 0.516 mmol). The reaction mixture was slowly warmed to rt. Upon stirring 4 h, TLC analysis indicated complete consumption of starting material. The reaction was diluted with H₂O and EtOAC and the layers separated. The aqueous was extracted 2× with EtOAc then the combined organic extracts were washed with brine, dried over Na₂SO₄, filtered, and concentrated. The crude product was purified using silica gel chromatography (MeOH/CH₂Cl₂ gradient) to yield 207 mg of desired product as a colorless oil in quantitative yield. LRMS (M+H)+: 402.1.

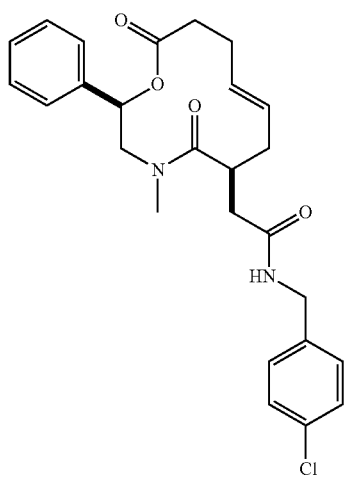

N-(4-chlorobenzyl)-2-((2R,6S,E)-4-methyl-5,12-dioxo-2-phenyl-1-oxa-4-azacyclododec-8-en-6-yl)acetamide To a solution of tert-butyl 2-(2R,6S,E)-4-methyl-5,12-dioxo-2-phenyl-1-oxa-4-azacyclododec-8-en-6-yl)acetate (130 mg, 0.336 mmol) in CH$_2$Cl$_2$ (258 µL) cooled in an ice/water bath was added trifluoroacetic acid (116 µL, 1.51 mmol) and the reaction mixture was stirred 1 h at which point LC-MS analysis indicated complete consumption of starting material. The reaction mixture was concentrated and the crude carboxylic acid was utilized immediately. To a solution of crude 2-(2R,6S,E)-4-methyl-5,12-dioxo-2-phenyl-1-oxa-4-azacyclododec-8-en-6-yl)acetic acid (111 mg, 0.335 mmol) in CH$_2$Cl$_2$ (4.2 mL) cooled in an ice/water bath was added EDC (64.2 mg, 0.335 mmol) and HOBt (45.3 mg, 0.335 mmol) and the resulting solution was stirred 30 min 4-chlorobenzylamine (41.0 µL, 0.335 mmol), iPr$_2$NEt (176 µL, 1.01 mmol) and DMAP (4 mg, 0.033 mmol) were subsequently added and the reaction mixture was slowly warmed to rt and stirred for 16 h at which point LC-MS analysis indicated complete consumption of starting material. The reaction mixture was diluted with saturated NH$_4$Cl and EtOAc and the layers separated. The aqueous was extracted 2× with EtOAc and the combined organic extracts were washed with 1 N HCl and brine, dried over Na$_2$SO$_4$, filtered, and concentrated. The crude product was purified using silica gel chromatography (MeOH/CH$_2$Cl$_2$ gradient) to yield the desired product as a colorless oil. $^1$H NMR (300 MHz, CD$_3$OD): δ 2.36-2.63 (m, 8H), 2.83 (dd, 1H, J=10.1, 14.4), 3.31 (s, 3H), 3.57-3.67 (m, 1H), 4.46 (dd, 1H, J=5.8, 15.0), 4.54 (dd, 1H, J=6.2, 14.9), 5.04 (dd, 1H, J=11.8, 14.2), 5.56-5.68 (m, 2H), 6.36 (dd, 1H, J=2.3, 11.7), 6.46 (bs, 1H), 7.31-7.41 (m, 5H), 7.53-7.58 (m, 4H); LRMS (M+H)$^+$: 469.10.

Synthesis of Certain Compounds of Formula II-b

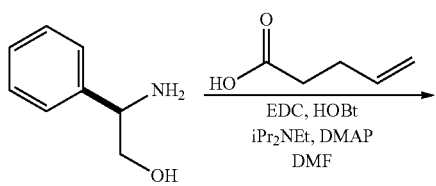

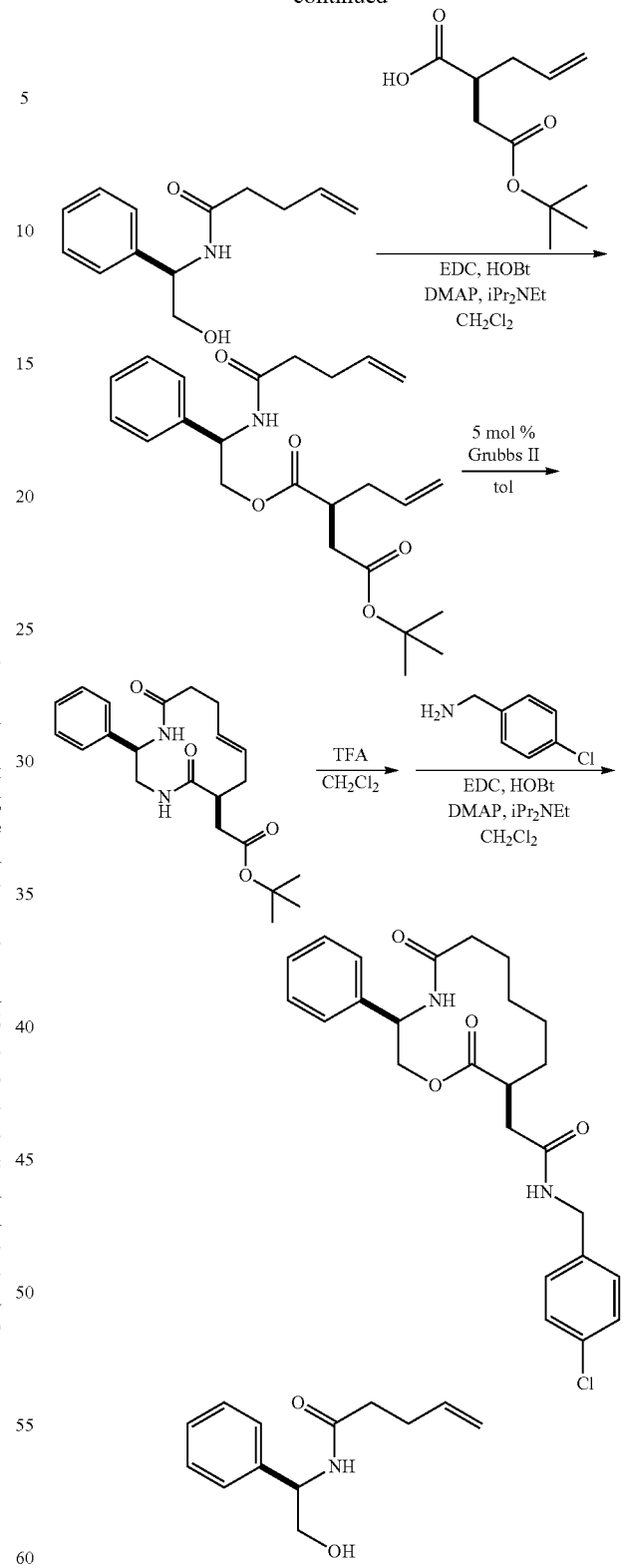

(R)-N-(2-hydroxy-1-phenylethyl)pent-4-enamide

To a solution of 4-pentenoic acid (2.55 mL, 25.0 mmol) in DMF (312 mL) cooled in an ice/water bath was added HOBt (3.37 g, 25.0 mmol) and EDC (4.79 g, 25.0 mmol) and the resulting solution was stirred for 30 min (R)-(−)-2-phenylglycinol (3.43 g, 25.0 mmol), iPr₂NEt (17.8 mL, 100 mmol), and DMAP (0.305 g, 2.50 mmol) were subsequently added and the reaction mixture was stirred 16 h at which point LC-MS analysis indicated complete consumption of starting material. The reaction mixture was diluted with saturated NH₄Cl and EtOAc and the layers separated. The aqueous layer was extracted 2× with EtOAc and the combined organic extracts were washed with 1 N HCl and brine, dried over Na₂SO₄, filtered, and concentrated. The crude product was purified using silica gel chromatography (MeOH/CH₂Cl₂ gradient) to yield 3.5 g of product as a colorless oil in 64% yield. LRMS (M+H)⁺: 220.1.

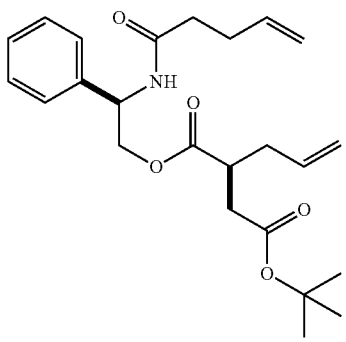

(S)-4-tert-butyl 1-((R)-2-pent-4-enamido-2-phenylethyl) 2-allylsuccinate

To a solution of (S)-2-(2-tert-butoxy-2-oxoethyl)pent-4-enoic acid (684 mg, 3.19 mmol) in DMF (25 mL) cooled in an ice/water bath was added EDC (612 mg, 3.19 mmol) and the resulting solution was stirred for 30 min. (R)-N-(2-hydroxy-1-phenylethyl)pent-4-enamide (700 mg, 3.19 mmol), iPr₂NEt (1.77 mL, 9.58 mmol), and DMAP (39.0 mg, 0.319 mmol) were subsequently added and the reaction mixture was stirred 16 h at which point LC-MS analysis indicated the presence of both starting material and desired product. The reaction mixture was diluted with saturated NH₄Cl and EtOAc and the layers separated. The aqueous layer was extracted 2× with EtOAc and the combined organic extracts were washed with 1 N HCl and brine, dried over Na₂SO₄, filtered, and concentrated. The crude product was purified using silica gel chromatography (MeOH/CH₂Cl₂ gradient) to yield 340 mg of product as a colorless oil in 26% yield. LRMS (M+Na)⁺: 438.4.

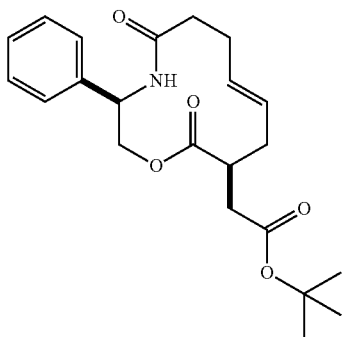

tert-butyl 2-((3R,11S,E)-5,12-dioxo-3-phenyl-1-oxa-4-azacyclododec-8-en-11-yl)acetate To a solution of (S)-4-tert-butyl 1-((R)-2-pent-4-enamido-2-phenylethyl) 2-allylsuccinate (340 mg, 0.818 mmol) in toluene (82 mL) was added Grubbs 2nd Generation catalyst (34.7 mg, 0.041 mmol) and the reaction mixture was heated to 65° C. Upon stirring 7 h with continued heating, TLC analysis indicated complete consumption of starting material. The reaction mixture was cooled to rt, diluted with degassed CH₂Cl₂ (8.2 mL) and Pb(OAc)₄ (181 mg, 0.409 mmol) was added. The resultant mixture was stirred for 12 h at which point the mixture was passed through a short plug of silica then concentrated using rotary evaporation. The resulting purple solid was triturated with methanol to further remove ruthenium complexes. The off white solid that remained was purified using silica gel chromatography (MeOH/CH₂Cl₂ gradient) to yield 130 mg of desired product as a white solid in 41% yield. LRMS (M+Na)⁺: 410.4.

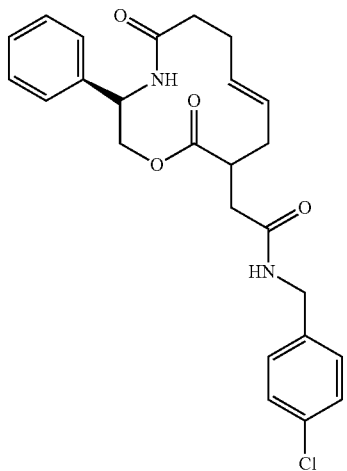

N-(4-chlorobenzyl)-2-((3R,11S,E)-5,12-dioxo-3-phenyl-1-oxa-4-azacyclododec-8-en-11-yl)acetamide To a solution of tert-butyl 2-((3R,11S,E)-5,12-dioxo-3-phenyl-1-oxa-4-azacyclododec-8-en-11-yl)acetate (130 mg, 0.336 mmol) in CH₂Cl₂ (258 µL) cooled in an ice/water bath was added trifluoroacetic acid (116 µL, 1.510 mmol) and the reaction mixture was stirred 1 h at which point LC-MS analysis indicated complete consumption of starting material. The reaction mixture was concentrated and the crude carboxylic acid was utilized immediately. To a solution of crude 2-((3R,11S,E)-5,12-dioxo-3-phenyl-1-oxa-4-azacyclododec-8-en-11-yl)acetic acid (111 mg, 0.335 mmol) in CH₂Cl₂ (4.2 mL) cooled in an ice/water bath was added EDC (64.2 mg, 0.335 mmol) and HOBt (45.3 mg, 0.335 mmol) and the resulting solution was stirred 30 min 4-chlorobenzylamine (41.0 µL, 0.335 mmol), iPr₂NEt (176 µL, 1.005 mmol) and DMAP (4.09 mg, 0.033 mmol) were subsequently added and the reaction mixture was slowly warmed to rt and stirred for 16 h at which point LC-MS analysis indicated complete consumption of starting material. The reaction mixture was diluted with saturated NH₄Cl and EtOAc and the layers separated. The aqueous was extracted 2× with EtOAc and the combined organic extracts were washed with 1 N HCl and brine, dried over Na₂SO₄, filtered, and concentrated. The crude product was purified using silica gel chromatography (MeOH/

$CH_2Cl_2$ gradient) to yield the desired product as a white solid. $^1H$ NMR (300 MHz, $(CD_3)_2SO$): δ 1.95-2.57 (m, 7H), 2.73-2.80 (m, 1H), 3.65 (dd, 1H, J=3.6, 11.3), 4.20 (s, 1H), 4.22 (s, 1H), 4.61 (apparent triplet, 1H, J=11.3), 5.23-5.34 (m, 3H), 7.22-7.24 (m, 9H), 8.25 (d, 1H, J=9.5), 8.41-8.46 (m, 1H); LRMS $(M+H)^+$: 455.1.

Example 5

Cell-Based Shh Pathway Assays and Recombinant Shh Proteins

ShhL2 cells are NIHT3 cells that have been transfected with a Gli-luciferase construct, as previously reported (Tapaile, et al. 2000; Surajit, et al., supra). ShhL2 cells (ATCC, Manassas, Va.) were cultured with DMEM (GIBCO, Carlsbad, Calif.), 10% Calf Bovine Serum (ATCC Manassas, Va.), 0.4 mg/ml G-418 (ATCC, Manassas, Va.), 0.15 mg/ml Zeocin (Invitrogen, Carlsbad Calif., Cat. No. R25001) at 37° C. When confluent, the cells were plated 1:5 into white 96-well optical-bottom plates and allowed to reach confluence over approximately 5-7 days. When confluent, the medium was removed and the ShhL2 cells were treated with test compound (for example, robotnikinin or cyclopamine) (EMD Biosciences, San Diego, Calif.) in DMEM with 0.5% Calf Bovine Serum. After incubation for 30 hours, each well was treated with 100 µL of Bright-Glo luciferase assay reagent (Promega, Madison, Wis.) and the plate was read with an Envision Multi-Label Reader 2102 luminometer (Perkin Elmer, Waltham, Mass.). Wells treated in identical fashion were then treated with Cell Titer-Glo reagent (Promega, Madison, Wis.) and read with an Envision Multi-Label Reader 2102 luminometer after being allowed to stand 10 minutes at room temperature.

The ptc−/− cell line was derived from an embryonic mouse fibroblast cell line transfected with a β-galactosidase construct. The cell line was cultured in DMEM with 10% FBS until confluent, and then cells were plated 1:5 into white 96-well optical-bottom plates and allowed to reach a confluent state over 3-4 days while incubating at 37° C. After reaching confluency, the medium was removed from each well, and the cells were treated with test compound (for example, robotnikinin or cyclopamine) (EMD Biosciences, San Diego, Calif.) in DMEM with 0.5% FBS. After a 30 hour incubation, the wells were treated with Beta-Glo assay reagent (Promega, Madison, Wis.) and allowed to be gently agitated for 30 minutes at room temperature. After the agitation was complete, plates were read with an Envision Multi-Label Reader 2102 luminometer.

Recombinant human sonic hedgehog 1845-CF, N-terminal peptide (rhShh) was obtained from R & D Systems (Minneapolis, Minn.) in lyophilized form. Purity was >95% based on SDS Page electrophoresis visualized with silver stain. Recombinant mouse amino-terminal peptide 461-CF (rmShh) was also obtained from R & D Systems in lyophilized form, and purity was >97% based on SDS Page electrophoresis visualized with silver stain.

Example 6

Surface Plasmon Resonance (SPR) Protein Binding Assays

Biacore™ T100 (GE Healthcare, Uppsala, Sweden) was used to perform the experiments reported herein. Sensor surface preparation and interaction analyses experiments were performed at 25° C. Prior to surface preparation, lyophilized ShhN protein (R&D Systems) was dissolved in either water or PBS buffer, at pH 7.4 and protein purity determined by Nu-Page 4-12% Bis-Tris gel in MOPS buffer with a silver stain sensor preparation.

ShhN was immobilized onto series S sensor chip CM4 via a standard N-ethyl-N'-(dimethylaminopropyl)carbodiimide/N-hydroxysuccinimide (EDC/NHS) amine coupling procedures (Biacore Sensor Surface Handbook, 2003, version AA, Biacore, Uppsala, Sweden). Shh was diluted to 10 µg/mL in 10 mM sodium acetate pH 5.5 for these procedures and resultant immobilization levels were 1000-1200 R.U.s. Control surfaces were prepared similarly without protein derivatization and utilized as a reference surfaces for compound binding experiments.

For compound interaction analyses, 0.01 M Hepes, pH 7.4, 0.15 M NaCl, 0.05% Surfactant P20 and 5% DMSO was used for both running and sample buffers. Compound samples were prepared by serial dilution in the range 0.78 uM-25 uM and flowed over control and derivatized surfaces for two minutes at a flow-rate of 80 µL/min. Zero concentration blank buffer cycles were included as negative control samples. Solvent correction procedures were included to compensate for any DMSO related bulk refractive index variations and performed as described previously (Karlsson, R. et al. *Anal. Biochem.* 278, 1-13, 2000). Non-specific binding effects to sensor surface CM4 were absent for all analyses reported.

Data analysis was carried out using Biacore T100 evaluation software v1.1.1. Data were prepared by subtraction of reference surface data and blank buffer sample data, a procedure commonly referred to as 'double referencing' (Myszka, D. G. *J. Mol. Recognit.* 12, 1-6, 1999). Solvent correction was then applied as described previously.

Certain compounds of formula I were found to bind ShhN with $K_D$ values less than or equal to 20 µM.

Example 7

Small Molecule Microarray (SMM) Screening

The three experimental SMM slides were incubated on parafilm (Alcon, Menasha Wis.) with 300 µL of a 25 µg/mL rmShh solution in a 0.1% BSA in PBS buffer. The negative control slides were incubated with 300 µL of 0.1% BSA in PBS buffer alone. All slides were allowed to incubate for one hour at room temperature followed by washing each slide with PBS buffer three times. Each slide was then incubated with 300 µL of a 5 µg/mL biotin-labeled Shh antibody (R & D Systems, Minneapolis Minn.) solution in TBS with 0.1% BSA. After one hour of incubation, all five slides were washed with TBS buffer three times. Each slide was then incubated at room temperature for one hour with 300 µL of a 20 pg/mL solution of streptavidin Alexa 647 (Invitrogen, Carlsbad Calif.) in TBST with 0.1% BSA followed by three washes with PBST. Slides were dried by centrifugation and scanned with a GenePix 4000B microarray plate reader (Axon Instruments, Sunnyvale Calif.). Data analysis was performed with GenePix Pro software (Axon Instruments, Sunnyvale Calif.).

Example 8

Primary Keratinocyte Cell Culture and Artificial Skin Equivalents

Culturing of primary human keratinocytes was previously described (Nguyen, B. C., et al., *Genes & Dev.* 20:1028-1042 (2006)). The full thickness skin model, EpiDermFT System (MatTek, Ashland), consists of normal, human-derived epidermal keratinocytes and normal, human-derived dermal fibroblasts which have been cultured to form a multilayered, highly differentiated model of the human dermis and epidermis.

Example 9

Analysis of Gene Expression by Real Time RT-PCR

Gene expression was compared by quantifying mRNA levels by real time RT-PCR. For this, total RNA preparations (1 μg) were used in a reverse transcriptase reaction with a mix of oligonucleotide dT and random hexamer primers, followed by real time PCR with gene-specific primers (Gli1: Qiagen Quantitect PrimerAssay QT00060501; Gli2: Qiagen Quantitect PrimerAssay QT00018648), using an Icycler IQTM real time detection system (Bio-Rad) according to the manufacturer's recommendation, with SYBR Green (Bio-Rad) for detection. Each sample was tested in triplicate, and the results were normalized by real time PCR of the same cDNA with 36B4 primers (36B4 forward primer: 5'-GCA ATG TTG CCA GTG TCT GT 3; reverse primer, 5'-GCC TTG ACC TTT TCA GCA AG-3').

For Gli2 transcription, certain compounds of formula I were found to possess $IC_{50}$ values less than to 2 μM.

Example 10

Topical Application

Eight-week-old C57BL/6J female mice were purchased from Charles River (Boston, Mass.). Mice were housed in community cages at the animal facilities of the Massachusetts General Hospital. All mice were fed water and murine chow ad libitum and kept under 12 h light/dark cycles. Active hair growth (anagen) was induced in the back skin during the telogen phase of the hair cycle by application of the wax-rosin mixture with subsequent depilation, as described before (Paus, R., Stenn, K. S., Link, R. E. (1990). *Br. J. Dermatol.* 122, 777-784).

Figure 8A:
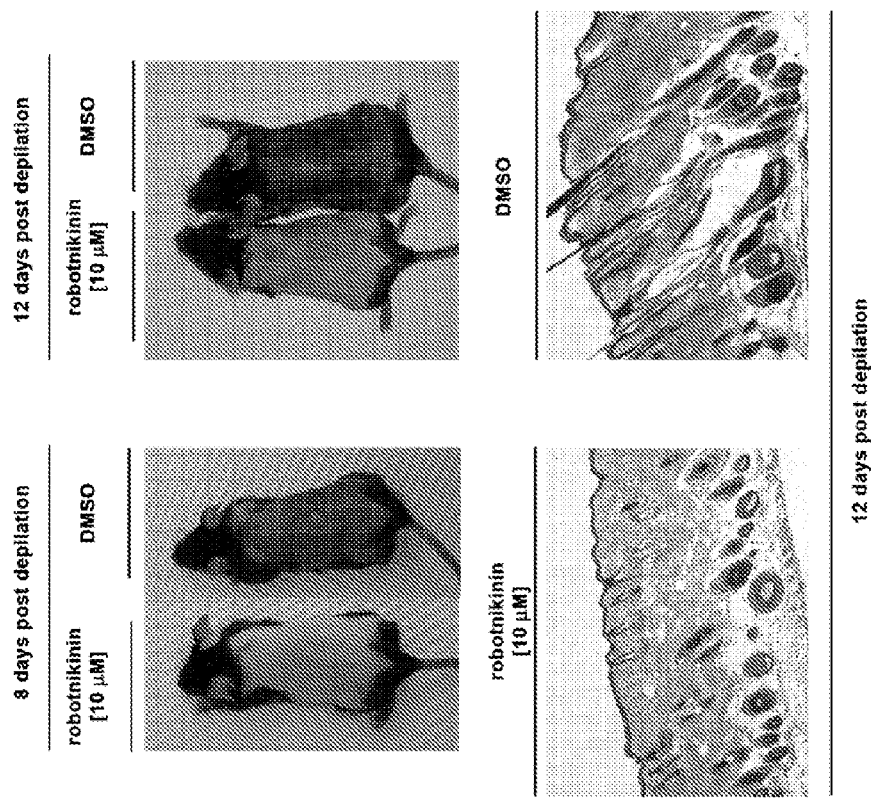
FIGS. 8a-b depicts the results of topical robotnikinin application experiments in mice. Topical application of robotnikinin or DMSO control following depilation shows that robotnikinin blocked hair regrowth 8 and 12 days post depilation (FIG. 8a, top panels). Harvested skin cross sections indicate a lack of hair follicles 12 days post depilation in robotnikinin-treated mouse (FIG. 8a, bottom panels).
Figure 8B:
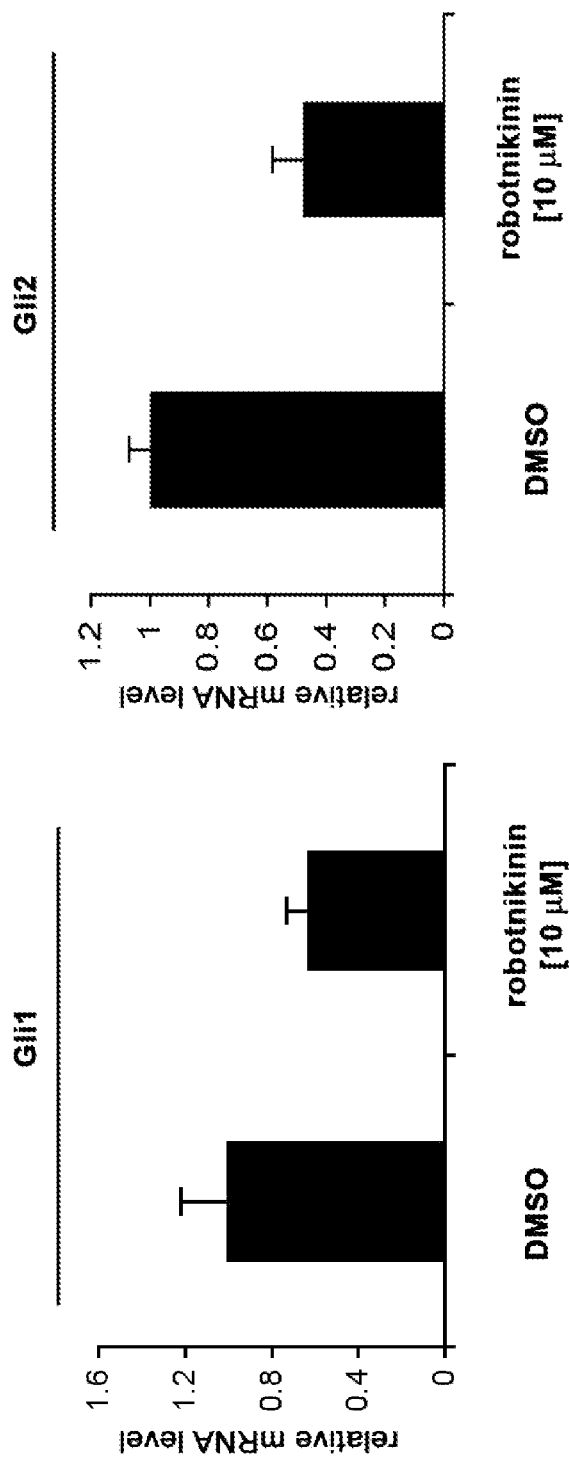
Figure 9:
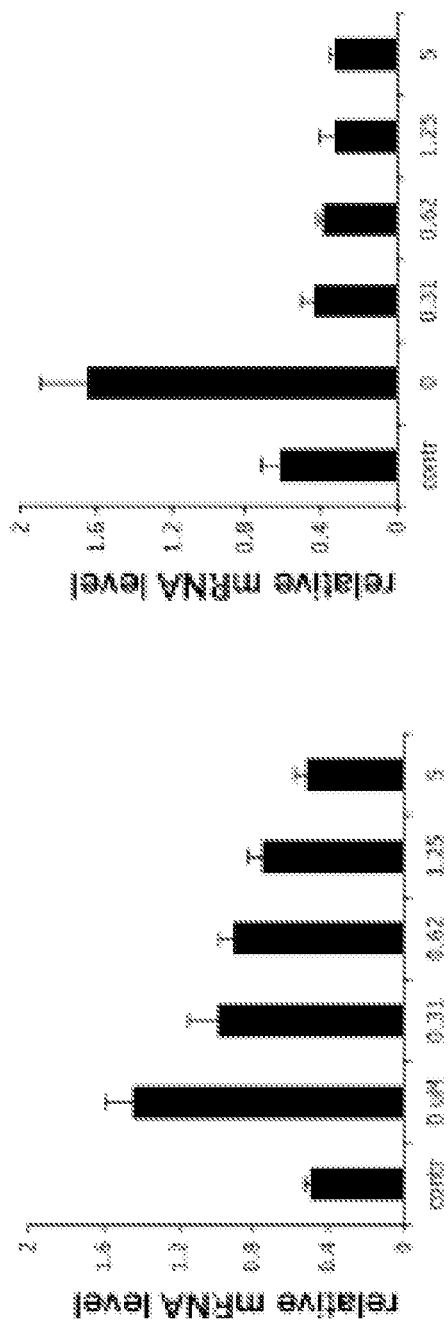
FIG. 9 depicts the results of experiments with primary human keratinocytes treated with robotnikinin and a compound of formula I. The results indicate that robotnikinin (left panel) and a compound of formula I (right panel) lower levels of endogenous Gli2 mRNA (analyzed by qPCR) in primary human keratinocytes in a dose-dependent manner

Robotnokinin was dissolved in 10% DMSO and applied every day topically on the depilated skin surface. Mice were kept in individual cages to avoid scratching. Telogen-anagen transformation was studied at the following time points: telogen (unmanipulated skin), anagen (day 8 postdepilation) and very late anagen (day 12 postdepilation) (see FIG. 8a, top panels). In all experiments, the neck region of back skin was harvested parallel to the vertebral line for either heat-mediated epidermal separation and subsequent real time RT-PCR analysis for Gli1 and Gli2 expression levels or embedded for histology on frozen sections (see FIG. 8a, bottom panel, and FIG. 8b).

Michelle K. Lee
*Deputy Director of the United States Patent and Trademark Office* changed to the formula: 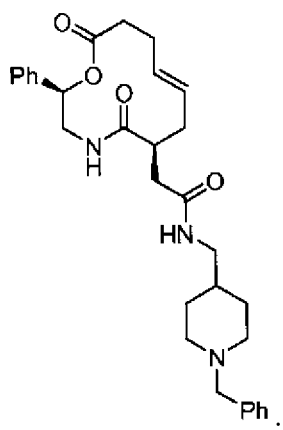

What is claimed is:
1. A compound of formula I:

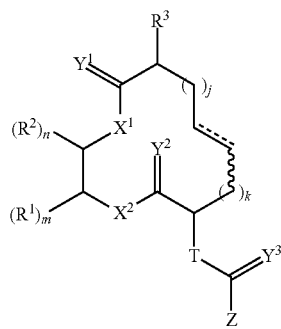

I or a pharmaceutically acceptable salt thereof, wherein:
= = = designates a single or double bond;
$X^1$ is —O—;
$X^2$ is —NR—;
$Y^1$, $Y^2$, and $Y^3$ are each =O;
Z is —$NR^4R^5$ or —$OR^5$;
T is a covalent bond or a bivalent $C_{1-12}$ saturated or unsaturated, straight or branched, aliphatic chain;
j is 1;
k is 1;
m is an integer from 0 to 2, inclusive;
n is an integer from 0 to 2, inclusive;
each occurrence of $R^1$ is independently hydrogen, halogen, —CN, —SCN, —$NO_2$, —$CO_2R$, —SOR, —$SO_2R$, —$NR_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur; or
two $R^1$ groups may be taken together with their intervening atoms to form a 3-8-membered ring; or
when $X^2$ is —NR—, $R^1$ and the R of —NR— may be taken together with their intervening atoms to form a 3-8-membered ring;
each occurrence of $R^2$ is independently hydrogen, halogen, —CN, —SCN, —$NO_2$, —$CO_2R$, —SOR, —$SO_2R$, —$NR_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur; or
two $R^2$ groups may be taken together with their intervening atoms to form a 3-8-membered ring;
$R^3$ is hydrogen, halogen, —CN, —SCN, —$NO_2$, —$CO_2R$, —SOR, —$SO_2R$, —$NR_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur;
$R^4$ is hydrogen;
$R^5$ is hydrogen or —$C(R^6)_3$;
each occurrence of $R^6$ is independently hydrogen, halogen, —CN, —SCN, —$NO_2$, —$CO_2R$, —SOR, —$SO_2R$, —$NR_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur; or two occurrences of $R^6$ may be taken together with their intervening atoms to form a 3-8-membered ring; and each R is independently hydrogen, a protecting group, —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{7-15}$ arylalkyl moiety, $C_{1-12}$ aliphatic moiety, 6-10-membered aryl moiety, 5-10-membered heteroaryl moiety having 1-4 heteroatoms independently selected from nitrogen, oxygen, and sulfur, or $C_{1-12}$ heteroaliphatic moiety; or:

two R on the same nitrogen atom may be taken with the nitrogen to form a 4-7-membered heterocyclic ring having 1-2 heteroatoms independently selected from nitrogen, oxygen, and sulfur;

wherein when a group is substituted, the group is substituted with one or more substituents independently selected from the group consisting of aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$—CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_{x1}$, —CO$_2$(R$_{x1}$), —CON(R$_{x1}$)$_2$, —OC(O)R$_{x1}$, —OCO$_2$R$_{x1}$, —OCON(R$_{x1}$)$_2$, —N(R$_{x1}$)$_2$, —S(O)$_2$R$_{x1}$, and —NR$_{x1}$(CO)R$_{x1}$, wherein each occurrence of R$_{x1}$ is independently selected from the group consisting of aliphatic, heteroaliphatic, aryl, heteroaryl, arylalkyl, and heteroarylalkyl;

with the proviso that $R^6$ is not —CH$_2$OH or —CH$_2$OCH$_2$CH$_2$OH.

2. The compound according to claim 1, wherein T is —CH$_2$—.

3. The compound according to claim 1, wherein $R^1$ is hydrogen.

4. The compound according to claim 1, wherein $R^2$ is optionally substituted 6-10-membered aryl.

5. The compound according to claim 4, wherein $R^2$ is phenyl.

6. The compound according to claim 1, wherein $R^3$ is hydrogen.

7. The compound according to claim 1, wherein Z is —NR$^4$R$^5$.

8. The compound according to claim 1, wherein $R^5$ is —C(R$^6$)$_3$.

9. The compound according to claim 8, wherein:

each occurrence of $R^6$ is independently hydrogen or an optionally substituted group selected from the group consisting of $C_{1-12}$ aliphatic, $C_{1-12}$ heteroaliphatic, $C_{7-15}$ arylalkyl, 6-10-membered aryl; or two occurrences of $R^6$ may be taken together with their intervening atoms to form a 3-8-membered ring.

10. The compound according to claim 9, wherein each occurrence of $R^6$ is independently hydrogen or an optionally substituted group selected from $C_{1-6}$ aliphatic and 6-10-membered aryl.

11. The compound according to claim 10, wherein one occurrence of $R^6$ is optionally substituted 6-membered aryl.

12. The compound according to claim 11, wherein one occurrence of $R^6$ is 4-chlorophenyl.

13. The compound according to claim 1, wherein --- designates a double bond.

14. The compound according to claim 13, wherein --- designates a trans double bond.

15. The compound according to claim 1, wherein the compound is of the formula:

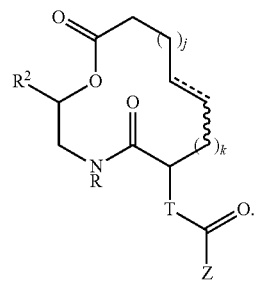

16. The compound according to claim 15, wherein the compound is of the formula:

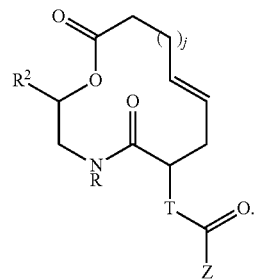

17. The compound according to claim 16, wherein the compound is of the formula:

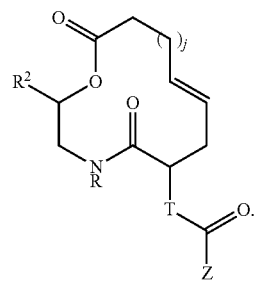

18. The compound according to claim 15, wherein the compound is selected from:

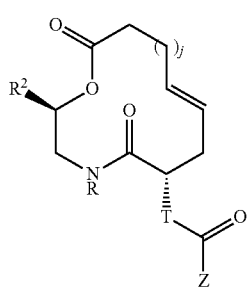 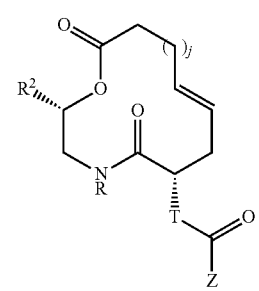

-continued

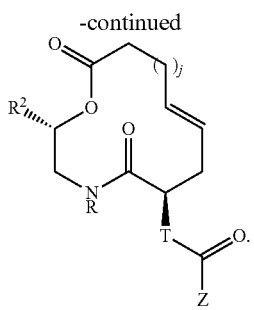

19. The compound according to claim 15, wherein the compound is of the formula:

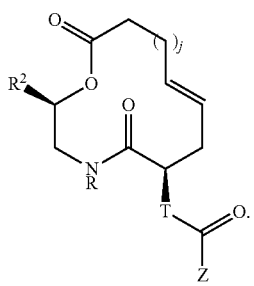

20. The compound according to claim 16, wherein the compound is of the formula:

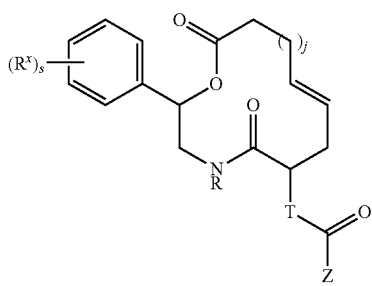

wherein,
s is an integer from 1 to 5, inclusive; and
each $R^x$ is independently selected from hydrogen, halogen, —CN, —SCN, —NO$_2$, —CO$_2$R, —SOR, —SO$_2$R, —NR$_2$, —OR, —SR, and an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur.

21. The compound according to claim 20, wherein the compound is of the formula:

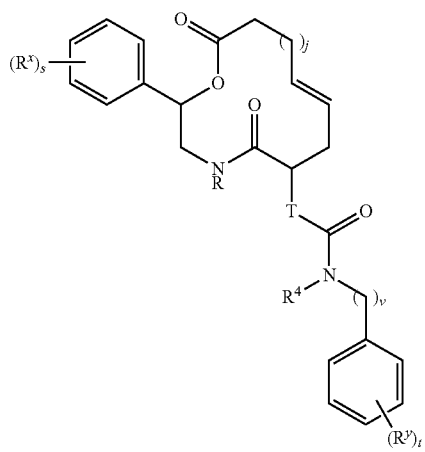

v is an integer from 1 to 10, inclusive;
t is an integer from 1 to 5, inclusive; and
each $R^y$ is independently selected from hydrogen, halogen, —CN, —SCN, —NO$_2$, —CO$_2$R, —SOR, —SO$_2$R, —NR$_2$, —OR, —SR, and an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur.

22. The compound according to claim 1, wherein the compound is selected from:

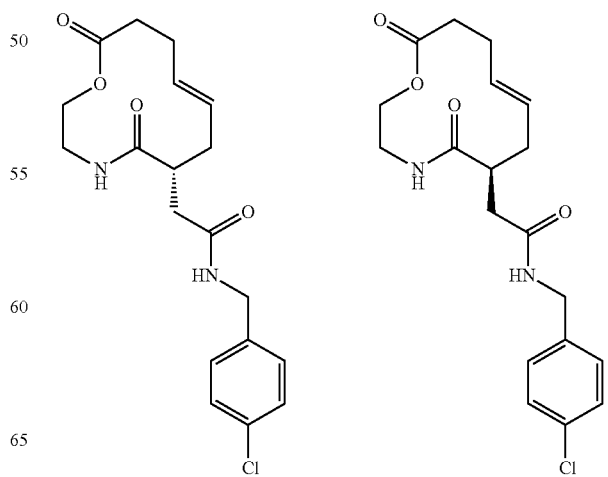

-continued
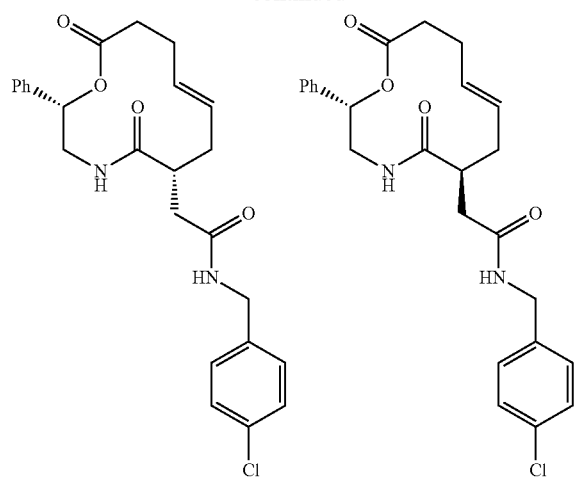
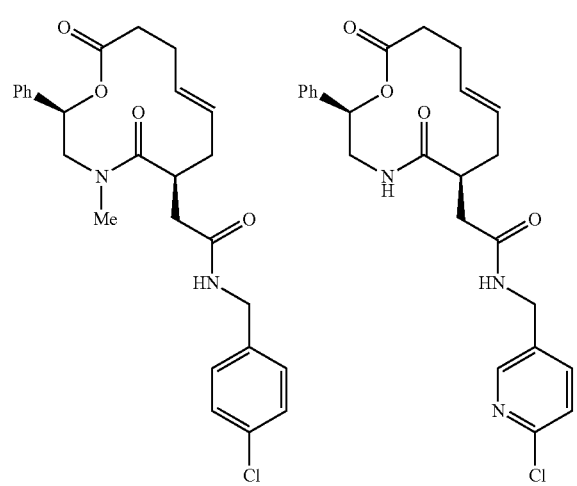
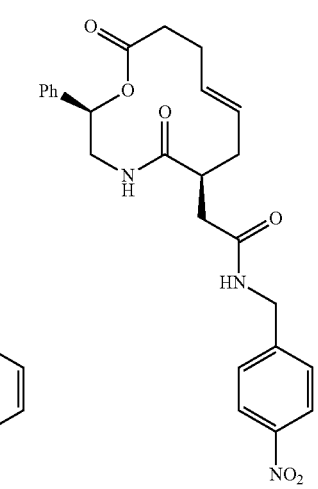
-continued
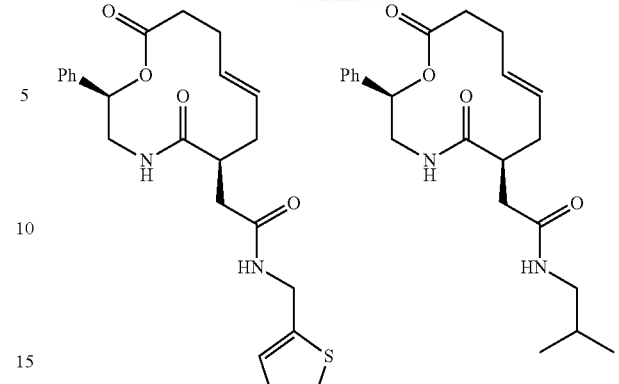
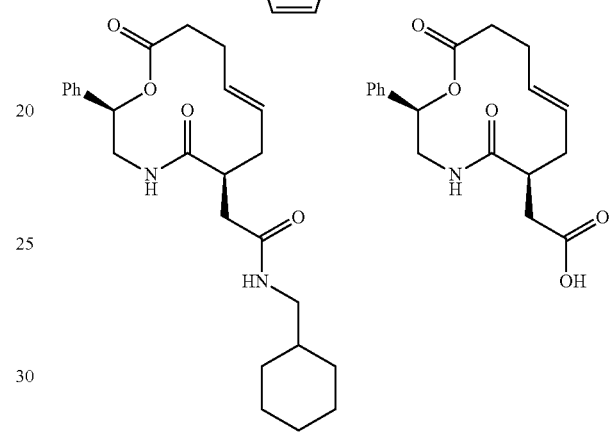
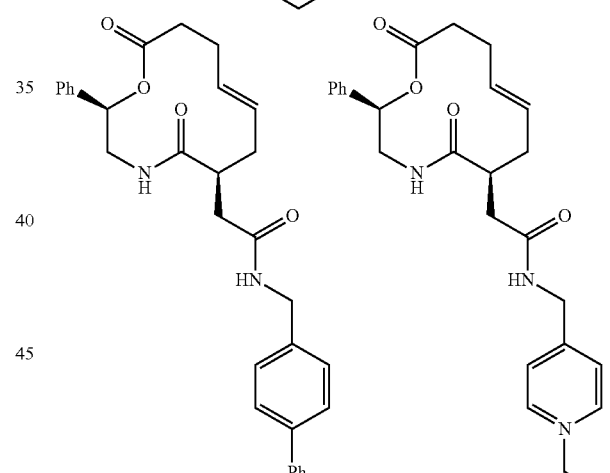
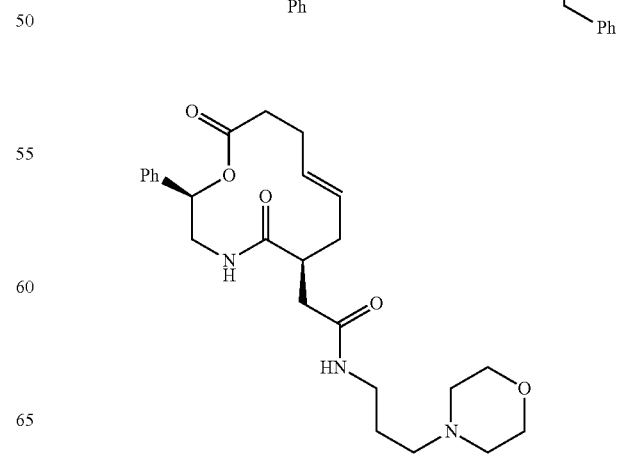

-continued

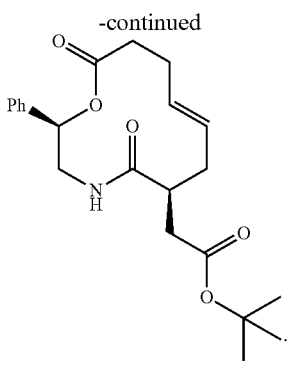

23. The compound according to claim 1, wherein the compound is:

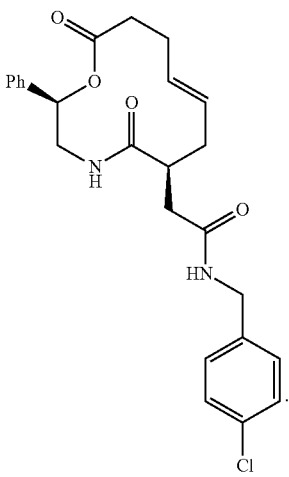

24. A pharmaceutical composition comprising a compound according to claim 1 and a pharmaceutically acceptable carrier.

25. A method of treating Gorlin syndrome, medulloblastoma, basal cell carcinoma, or pancreatic cancer in a subject suffering therefrom, the method comprising administering to the subject a therapeutically effective amount of a compound of formula I:

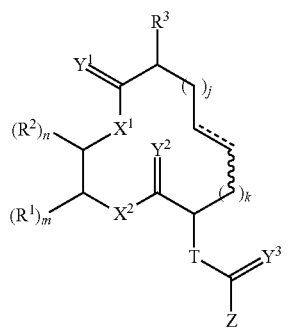

or a pharmaceutically acceptable salt thereof, wherein:
  - - - designates a single or double bond;
$X^1$ is —O—;
$X^2$ is —NR—;
$Y^1$, $Y^2$, and $Y^3$ are each =O;
Z is —NR$^4$R$^5$ or —OR$^5$;
T is a covalent bond or a bivalent $C_{1-12}$ saturated or unsaturated, straight or branched, aliphatic chain;
j is 1;
k is 1;
m is an integer from 0 to 2, inclusive;
n is an integer from 0 to 2, inclusive;
each occurrence of $R^1$ is independently hydrogen, halogen, —CN, —SCN, —NO$_2$, —CO$_2$R, —SOR, —SO$_2$R, —NR$_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur; or
two $R^1$ groups may be taken together with their intervening atoms to form a 3-8-membered ring; or
when $X^2$ is —NR—, $R^1$ and the R of —NR— may be taken together with their intervening atoms to form a 3-8-membered ring;
each occurrence of $R^2$ is independently hydrogen, halogen, —CN, —SCN, —NO$_2$, —CO$_2$R, —SOR, —SO$_2$R, —NR$_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur; or
two $R^2$ groups may be taken together with their intervening atoms to form a 3-8-membered ring;
$R^3$ is hydrogen, halogen, —CN, —SCN, —NO$_2$, —CO$_2$R, —SOR, —SO$_2$R, —NR$_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur;
$R^4$ is hydrogen;
$R^5$ is hydrogen or —C(R$^6$)$_3$;
each occurrence of $R^6$ is independently hydrogen, halogen, —CN, —SCN, —NO$_2$, —CO$_2$R, —SOR, —SO$_2$R, —NR$_2$, —OR, —SR, or an optionally substituted group selected from the group consisting of —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{1-12}$ aliphatic, $C_{1-12}$ heteroaliphatic, $C_{7-15}$ arylalkyl, $C_{3-15}$ heteroarylalkyl, 6-10-membered aryl, 5-10-membered heteroaryl having 1-4 heteroatoms independently selected from nitrogen, oxygen, and sulfur; and 4-7-membered heterocyclyl having 1-2 heteroatoms independently selected from nitrogen, oxygen, and sulfur; or two occurrences of $R^6$ may be taken together with their intervening atoms to form a 3-8-membered ring; and each R is independently hydrogen, a protecting group, —C(=O)-alkyl, —C(=O)-alkenyl, —C(=O)-alkynyl, —C(=O)-aryl, —C(=O)-carbocyclic, —C(=O)-heterocyclic, —C(=O)-(aromatic heterocyclic), $C_{7-15}$ arylalkyl moiety, $C_{1-12}$ aliphatic moiety, 6-10-membered aryl moiety, 5-10-membered heteroaryl moiety having 1-4 heteroatoms independently selected from nitrogen, oxygen, and sulfur, or $C_{1-12}$ heteroaliphatic moiety; or:

two R on the same nitrogen atom may be taken with the nitrogen to form a 4-7-membered heterocyclic ring having 1-2 heteroatoms independently selected from nitrogen, oxygen, and sulfur;

wherein when a group is substituted, the group is substituted with one or more substituents independently selected from the group consisting of aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_{x1}$, —CO$_2$(R$_{x1}$), —CON(R$_{x1}$)$_2$, —OC(O)R$_{x1}$, —OCO$_2$R$_{x1}$, —OCON (R$_{x1}$)$_2$, —N(R$_{x1}$)$_2$, —S(O)$_2$R$_{x1}$, and —NR$_{x1}$(CO)R$_{x1}$, wherein each occurrence of R$_{x1}$ is independently selected from the group consisting of aliphatic, heteroaliphatic, aryl, heteroaryl, arylalkyl, and heteroarylalkyl.

26. The compound according to claim 1, wherein $R^2$ is hydrogen.

27. The compound according to claim 1, wherein Z is —OR$^5$.

28. The compound according to claim 1, wherein $R^5$ is hydrogen.

29. The compound according to claim 8, wherein two occurrences of $R^6$ are hydrogen.

30. The compound according to claim 8, wherein one occurrence of $R^6$ is an optionally substituted group selected from the group consisting of $C_{1-6}$ aliphatic group, 5-10-membered heteroaryl having 1-4 heteroatoms independently selected from nitrogen, oxygen, and sulfur, and 4-7-membered heterocyclyl having 1-2 heteroatoms independently selected from nitrogen, oxygen, and sulfur.

* * * * *

UNITED STATES PATENT AND TRADEMARK OFFICE
CERTIFICATE OF CORRECTION

PATENT NO. : 8,530,456 B2  Page 1 of 2
APPLICATION NO. : 12/988755
DATED : September 10, 2013
INVENTOR(S) : Lee F. Peng et al.

It is certified that error appears in the above-identified patent and that said Letters Patent is hereby corrected as shown below:

In the Claims:

In claim 17, at column 116, lines 40-50, the formula: 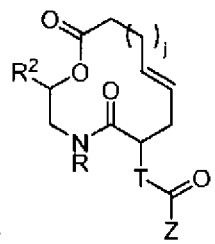 should be changed to the formula: 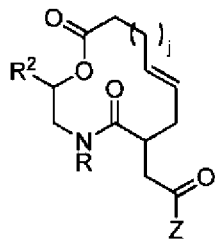 .

In claim 22, at column 120, lines 33-50, the formula: 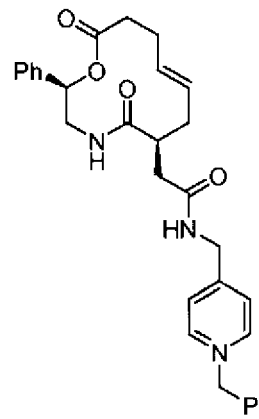 should be

Signed and Sealed this
Twenty-ninth Day of April, 2014